US012667621B2

(12) United States Patent
Haas et al.

(10) Patent No.: US 12,667,621 B2
(45) Date of Patent: Jun. 30, 2026

(54) RNA FORMULATIONS SUITABLE FOR THERAPY

(71) Applicant: BIONTECH SE, Mainz (DE)

(72) Inventors: Heinrich Haas, Mainz (DE); Jorge Moreno Herrero, Mainz (DE); Anne Marion Genevieve Schlegel, Mainz (DE); Stephanie Erbar, Mainz (DE)

(73) Assignee: BioNTech SE, Mainz (DE)

( * ) Notice: Subject to any disclaimer, the term of this patent is extended or adjusted under 35 U.S.C. 154(b) by 849 days.

(21) Appl. No.: 17/621,136

(22) PCT Filed: Jul. 1, 2020

(86) PCT No.: PCT/EP2020/068502
    § 371 (c)(1),
    (2) Date: Dec. 20, 2021

(87) PCT Pub. No.: WO2021/001417
    PCT Pub. Date: Jan. 7, 2021

(65) Prior Publication Data
    US 2022/0362388 A1    Nov. 17, 2022

(51) Int. Cl.
    *A61K 47/56*    (2017.01)
    *A61K 9/00*    (2006.01)
    (Continued)

(52) U.S. Cl.
    CPC ............ *A61K 47/56* (2017.08); *A61K 9/0019* (2013.01); *A61K 47/549* (2017.08);
    (Continued)

(58) Field of Classification Search
    None
    See application file for complete search history.

(56) References Cited

FOREIGN PATENT DOCUMENTS

| KR | 20180047442 A | 5/2018 |
| WO | WO-2007/133812 A2 | 11/2007 |

(Continued)

OTHER PUBLICATIONS

Tan, PH., Yang, LC., Shih, HC. et al. Gene knockdown with intrathecal siRNA of NMDA receptor NR2B subunit reduces formalin-induced nociception in the rat. Gene Ther 12, 59-66 (2005). https://doi.org/10.1038/sj.gt.3302376 (Year: 2005).*

(Continued)

*Primary Examiner* — Evelyn Y Pyla
*Assistant Examiner* — Jagamya Vijayaraghavan
(74) *Attorney, Agent, or Firm* — Choate, Hall & Stewart LLP; Brenda Herschbach Jarrell; Michael A. Shinall

(57) ABSTRACT

The present invention relates to compositions comprising RNA, preferably messenger RNA (mRNA), more preferably self-amplifying RNA (saRNA), and polymers, in particular cationic polymers, such as polyethylenimine (PEI), poly-L-Lysin (PEL), polyvinylamine (PVA) or polyallylamine (PAA), where individual RNA molecules are present in solution. In the formulations, the RNA is preferentially present in the form of monomers, dimers, timers or oligomers, but not as aggregates comprising a large number of RNA molecules per aggregate, in particular large polyplex nanoparticles. The formulations display improved transfection efficacy and they can be used for delivery of RNA to a subject, where they have an improved dose response relationship in comparison to formulations where large aggregates in the form of polyplex nanoparticles are present.

17 Claims, 34 Drawing Sheets

Specification includes a Sequence Listing.

A

B

(51) Int. Cl.
    *A61K 47/54*     (2017.01)
    *A61K 48/00*     (2006.01)
(52) U.S. Cl.
    CPC ........ *A61K 48/0041* (2013.01); *A61K 48/005*
        (2013.01); *A61K 48/0075* (2013.01)

(56) References Cited

FOREIGN PATENT DOCUMENTS

| | | |
|---|---|---|
| WO | WO-2015/173824 A1 | 11/2015 |
| WO | WO-2016/063225 A1 | 4/2016 |
| WO | WO-2017/068013 A1 | 4/2017 |
| WO | WO-2017/068016 A1 | 4/2017 |
| WO | WO-2019/137999 A1 | 7/2019 |

OTHER PUBLICATIONS

Evers, Martijn & Kulkarni, Jayesh & van der Meel, Roy & Cullis, Pieter & Vader, Pieter & Schiffelers, Raymond. (2017). State-of-the-Art Design and Rapid-Mixing Production Techniques of Lipid Nanoparticles for Nucleic Acid Delivery. Small Methods. 2. 10.1002/smtd.201700375. (Year: 2017).*

Rezaee, M., Gholami, L., Gildeh, M.S. et al. Charge reduction: an efficient strategy to reduce toxicity and increase the transfection efficiency of high molecular weight polyethylenimine. J. Pharm. Investig. 49, 105-114 (2019). (Year: 2018).*

Wang C, Yuan W, Xiao F, Gan Y, Zhao X, Zhai Z, Zhao X, Zhao C, Cui P, Jin T, Chen X, Zhang X. Biscarbamate Cross-Linked Low-Molecular-Weight Polyethylenimine for Delivering Anti-chordin siRNA into Human Mesenchymal Stem Cells for Improving Bone Regeneration. Front Pharmacol. Aug. 28, 2017;8:572. (Year: 2017).*

Zhao Y, Zheng C, Zhang L, Chen Y, Ye Y, Zhao M. Knockdown of STAT3 expression in SKOV3 cells by biodegradable siRNA-PLGA/CSO conjugate micelles. Colloids Surf B Biointerfaces. Mar. 1, 2015;127:155-63. doi: 10.1016/j.colsurfb.2015.01.034. Epub Jan. 28, 2015. PMID: 25677339. (Year: 2015).*

Lu ZX, Liu LT, Qi XR. Development of small interfering RNA delivery system using PEI-PEG-APRPG polymer for antiangiogenic vascular endothelial growth factor tumor-targeted therapy. Int J Nanomedicine. 2011;6:1661-73. doi: 10.2147/IJN.S22293. Epub Aug. 11, 2011. PMID: 21904456; PMCID: PMC3160952. (Year: 2011).*

Kauffman KJ, Dorkin JR, Yang JH, Heartlein MW, DeRosa F, Mir FF, Fenton OS, Anderson DG. Optimization of Lipid Nanoparticle Formulations for mRNA Delivery in Vivo with Fractional Factorial and Definitive Screening Designs. Nano Lett. Nov. 11, 2015;15(11):7300-6. doi: 10.1021/acs.nanolett.5b02497. (Year: 2015).*

Lechanteur A, Sanna V, Duchemin A, Evrard B, Mottet D, Piel G. Cationic Liposomes Carrying siRNA: Impact of Lipid Composition on Physicochemical Properties, Cytotoxicity and Endosomal Escape. Nanomaterials (Basel). Apr. 24, 2018;8(5):270. doi: 10.3390/nano8050270. PMID: 29695068; PMCID: PMC5977284. (Year: 2018).*

Aigner, A. et al., Delivery of unmodified bioactive ribozymes by an RNA-stabilizing polyethylenimine (LMW-PEI) efficiently downregulates gene expression, Gene Therapy, 9:1700-1707 (2002).

Derouchey, J. et al., Decorated Rods: A "Bottom-Up" Self-Assembly of Monomolecular DNA Complexes, J. Phys. Chem. B., 110:4548-4554 (2006).

Mann, A. et al., DNA condensation by poly-L-lysine at the single molecule level: Role of DNA concentration and polymer length, Journal of Controlled Release, 125:252-262 (2008).

Perevyazko, I. et al., Polyelectrolyte Complexes of DNA and Linear PEI: Formation, Composition and Properties, Langmuir, 28:16167-16176 (2012).

Blakney, A. et al., Effects of cationic adjuvant formulation particle type, fluidity and immunomodulators on delivery and immunogenicity of saRNA, J. Control. Release, 304:65-74 (2019).

Boeckle, S. et al., Purification of polyethylenimine polyplexes highlights the role of free polycations in gene transfer, The Journal of Gene Medicine, 6:1102-1111 (2004).

Cai, J. et al., Quantitative study of effects of free cationic chains on gene transfection in different intracellular stages, Journal of Controlled Release, 238:71-79 (2016).

Florea, B. et al., Transfection Efficiency and Toxicity of Polyethylenimine in Differentiated Calu-3 and Nondifferentiated COS-1 Cell Cultures, AAPS PharmSci, 4(3) Article 12: 11 pages (2002).

International Search Report for PCT/EP2020/068502, 8 pages (Oct. 26, 2020).

Neuberg, P. and Kichler, A., Recent Developments in Nucleic Acid Delivery with Polyethylenimines, Advances in Genetics, 88:263-288 (2014).

Sahin, U. et al., mRNA-based therapeutics—developing a new class of drugs, Nature Reviews/Drug Discovery, 13:759-780 (2014).

Vogel, A. et al., Self-Amplifying RNA Vaccines Give Equivalent Protection against Influenza to mRNA Vaccines but at Much Lower Doses, Mol. Ther., 26(2):446-455 (2018).

Written Opinion for PCT/EP2020/068502, 15 pages (Oct. 26, 2020).

Forrest, M. et al., A Degradable Polyethylenimine Derivative with Low Toxicity for Highly Efficient Gene Delivery, Bioconjugate Chem., 14:934-940 (2003).

* cited by examiner

Figure 1
A
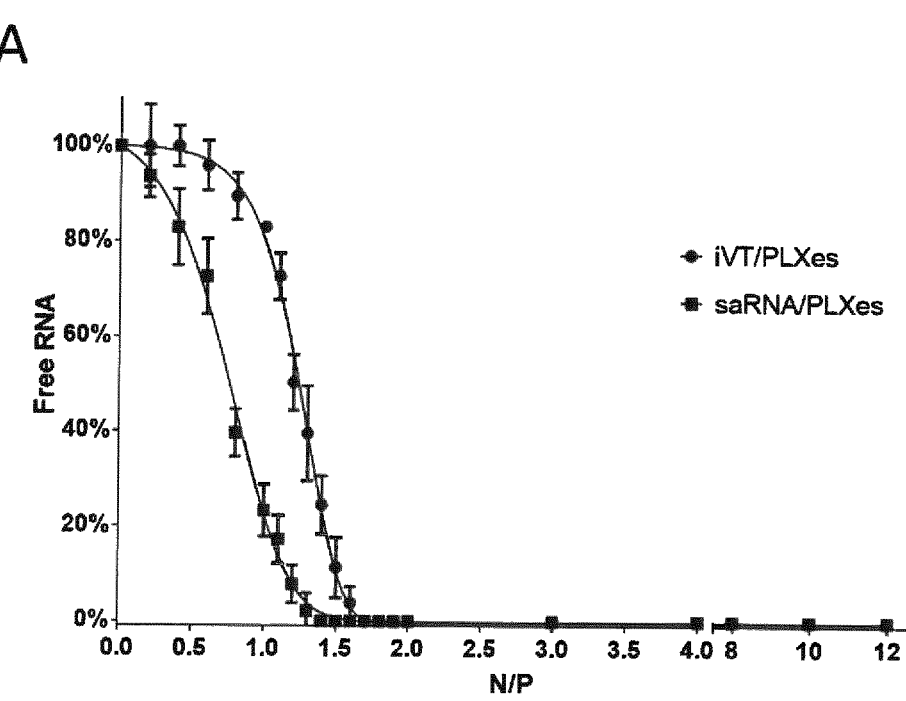
B
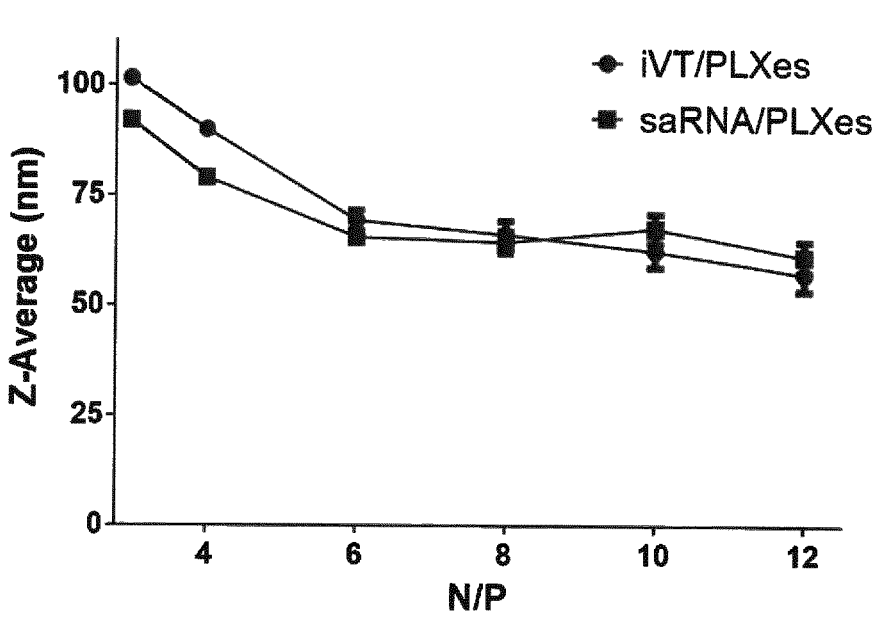

Figure 2
A
iVT:PLXes Fractions/ UV-Quantification
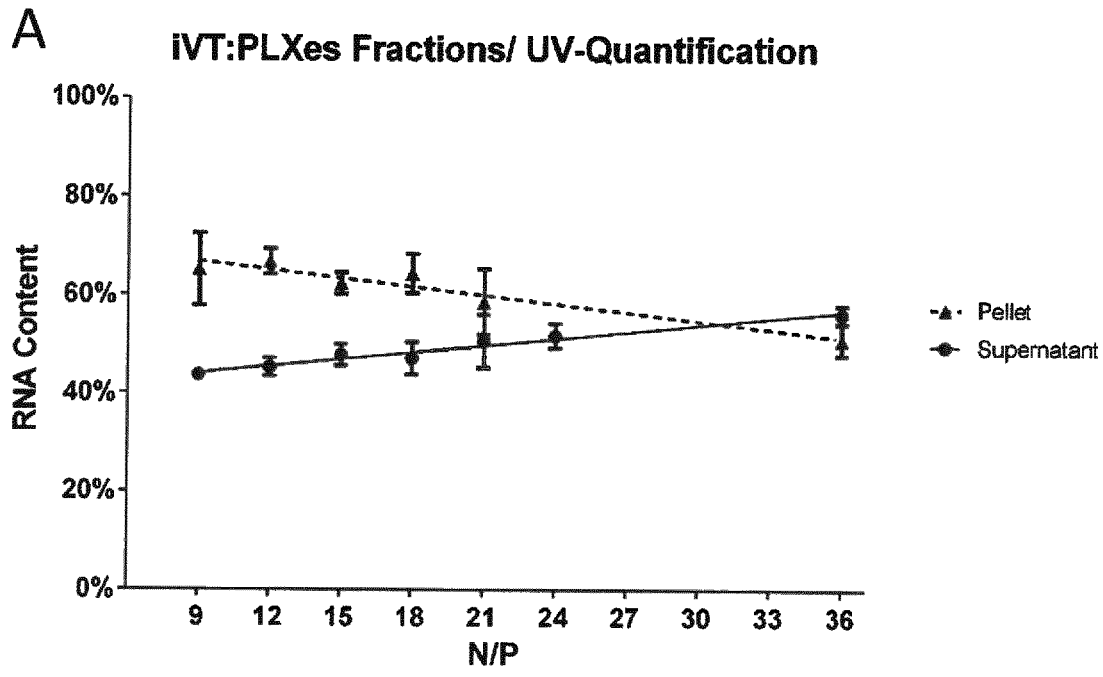
B
saRNA:PLXes Fractions/ UV-Quantification
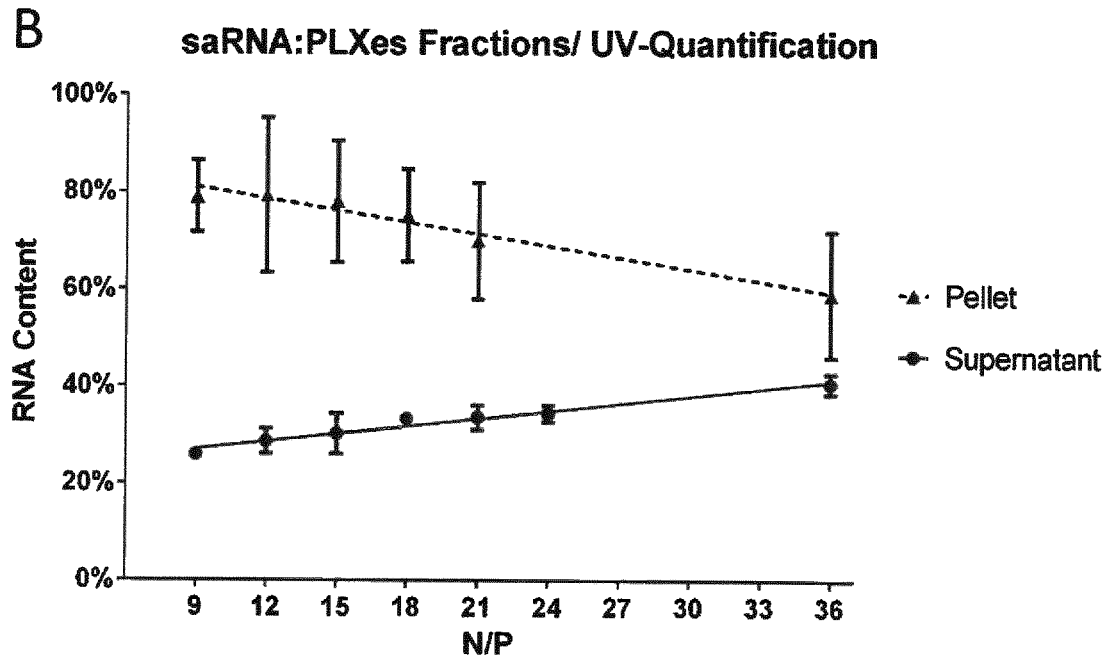

Figure 7
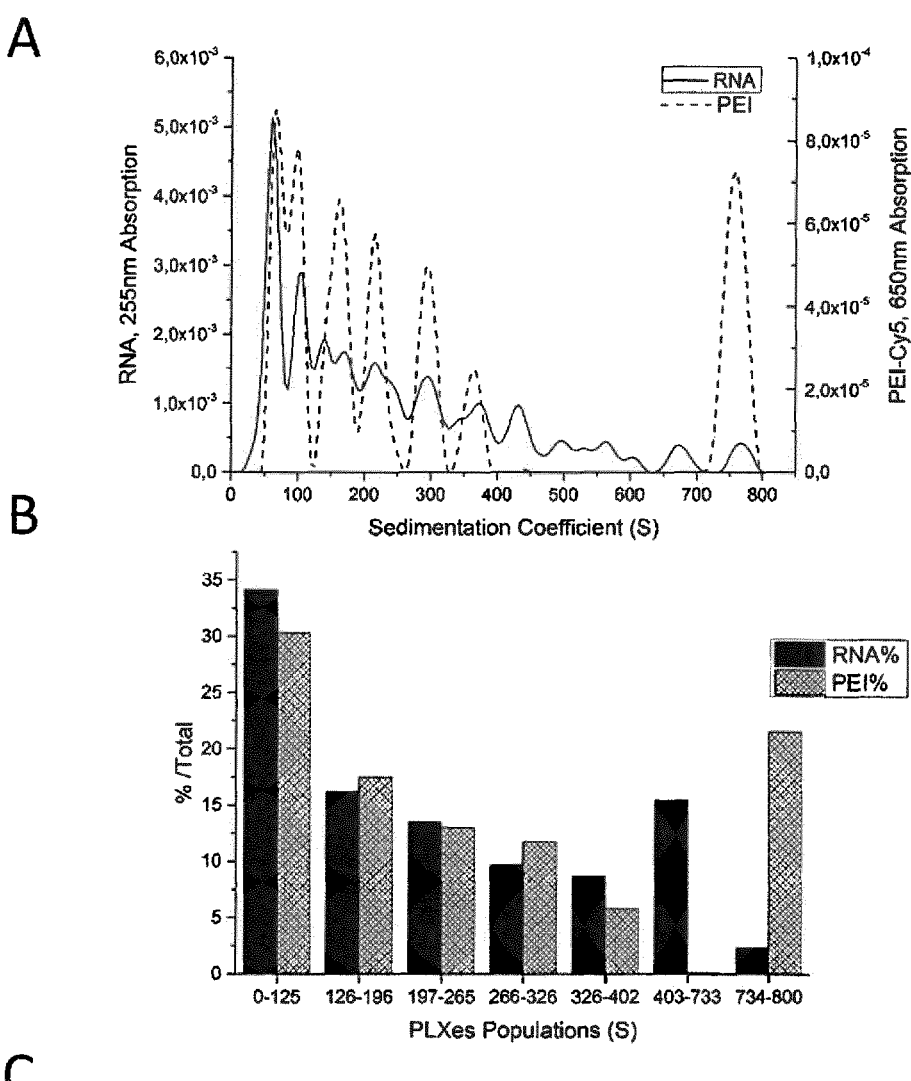
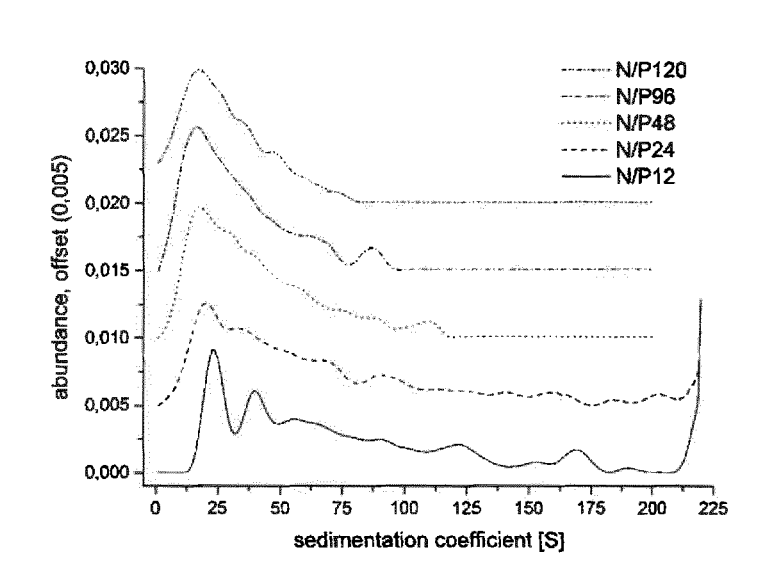

Figure 9
A
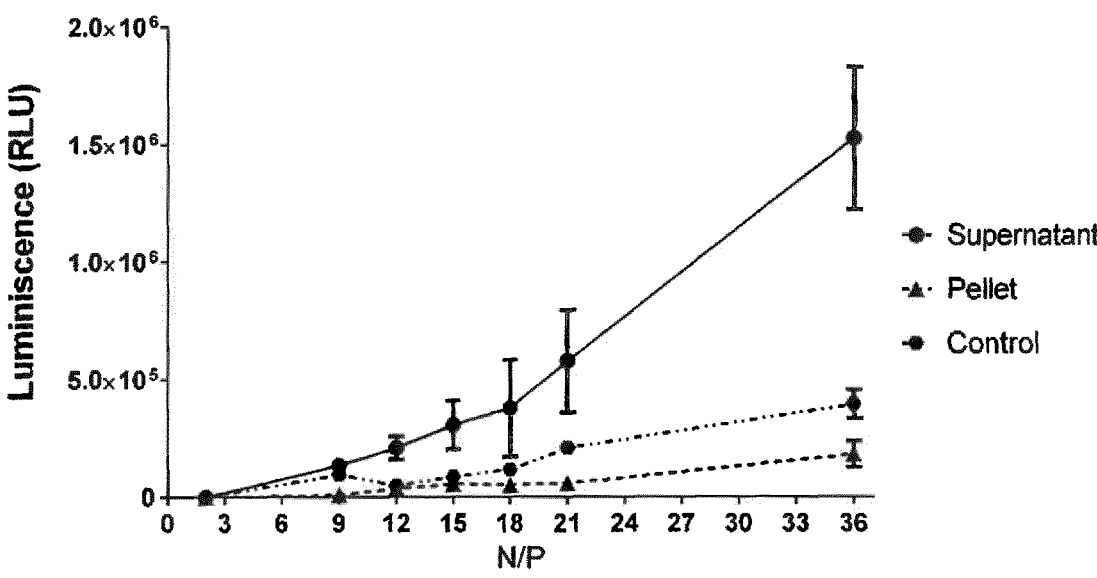
B
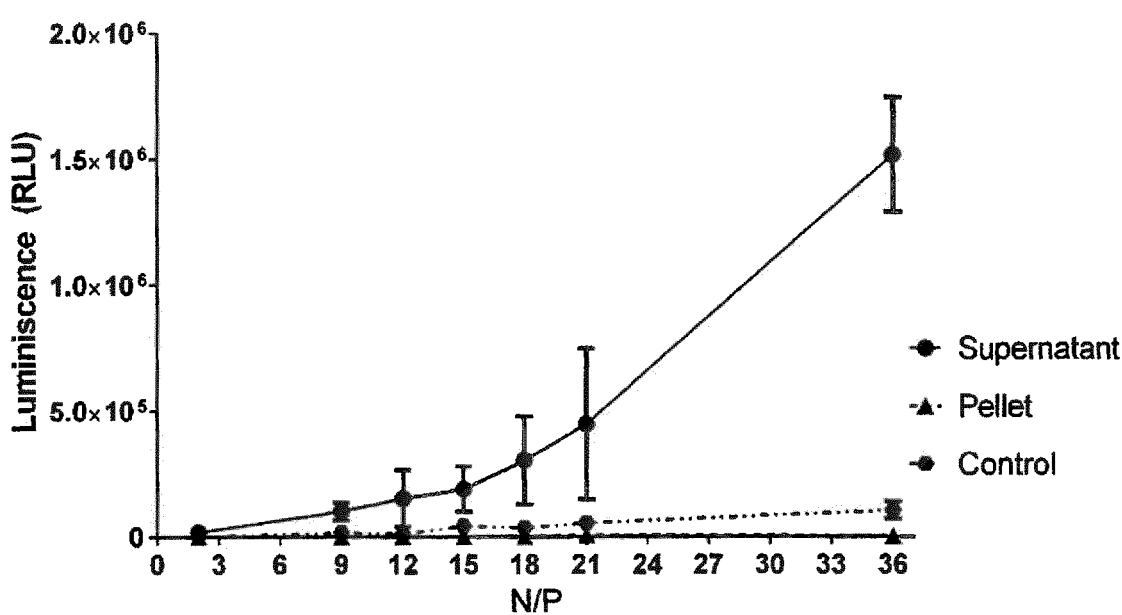

Figure 10
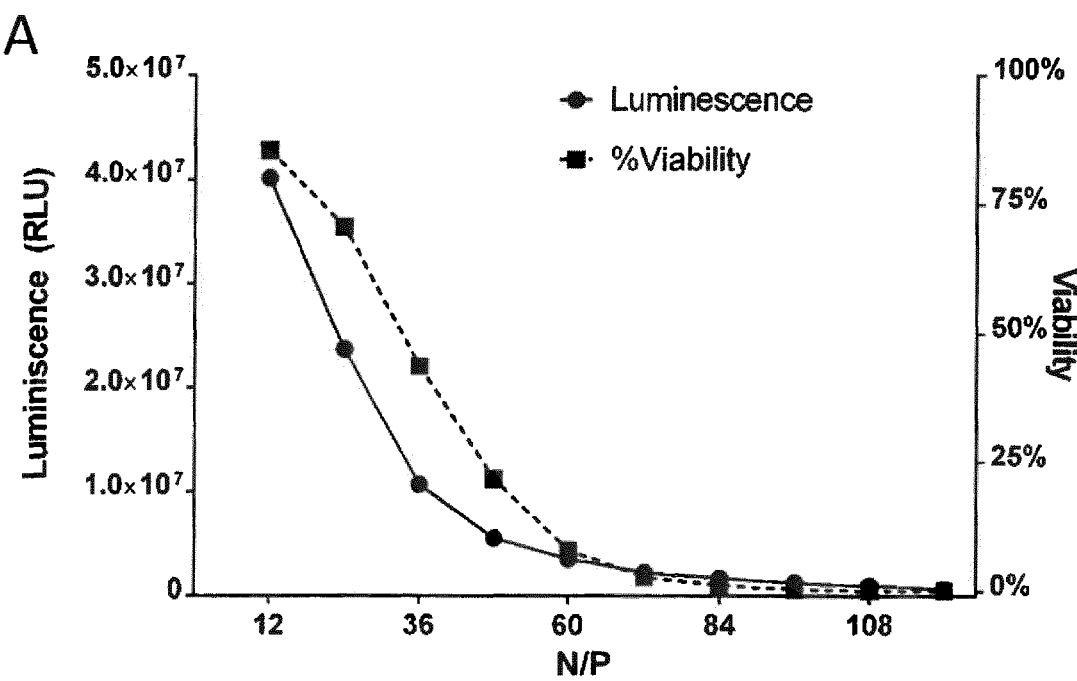
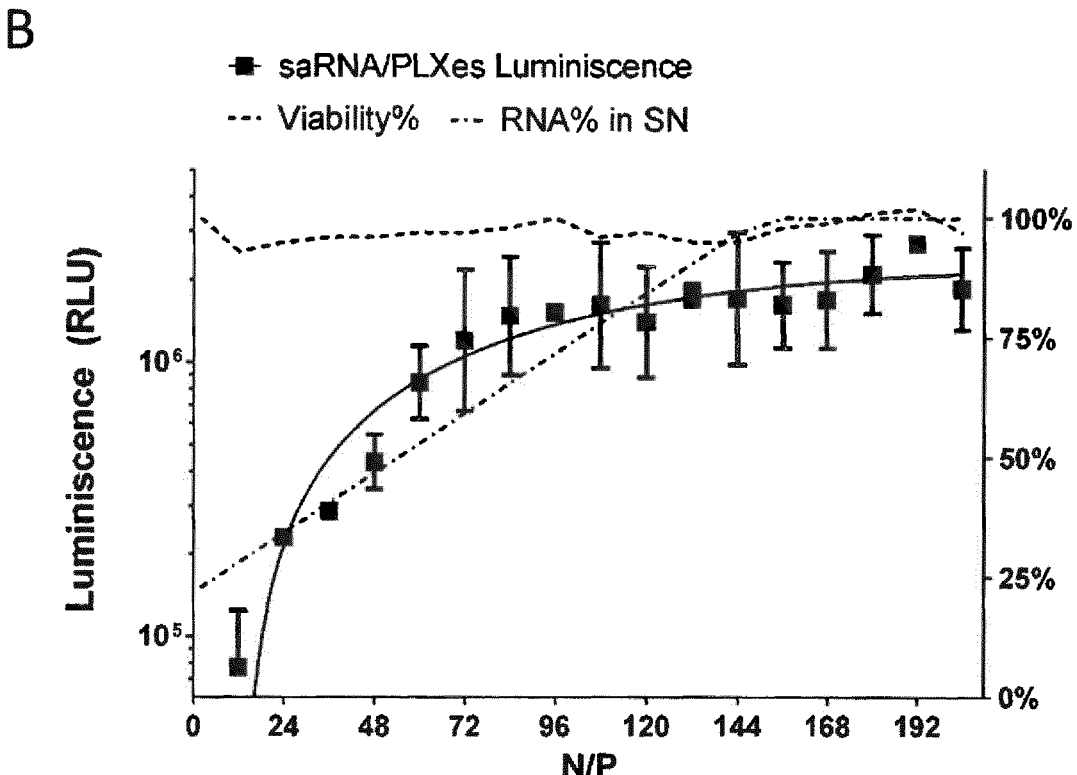

Figure 11
A
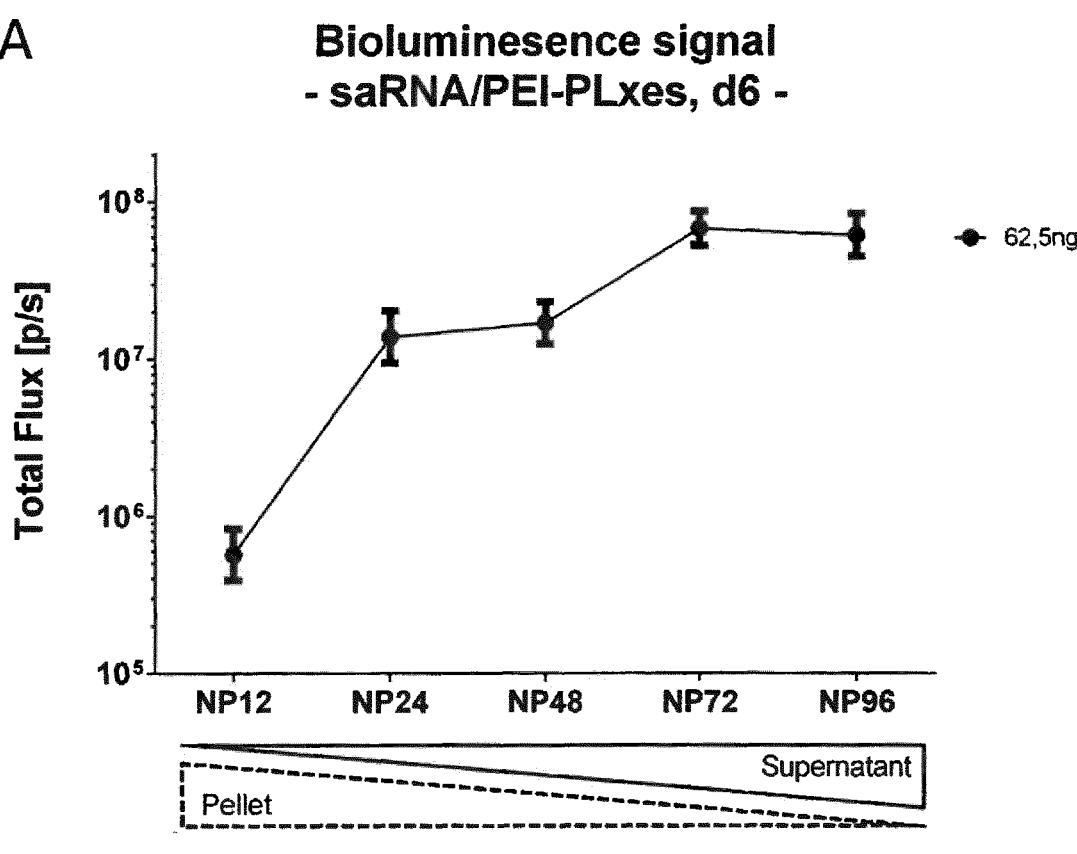
Bioluminesence signal
- saRNA/PEI-PLxes, d6 -
B
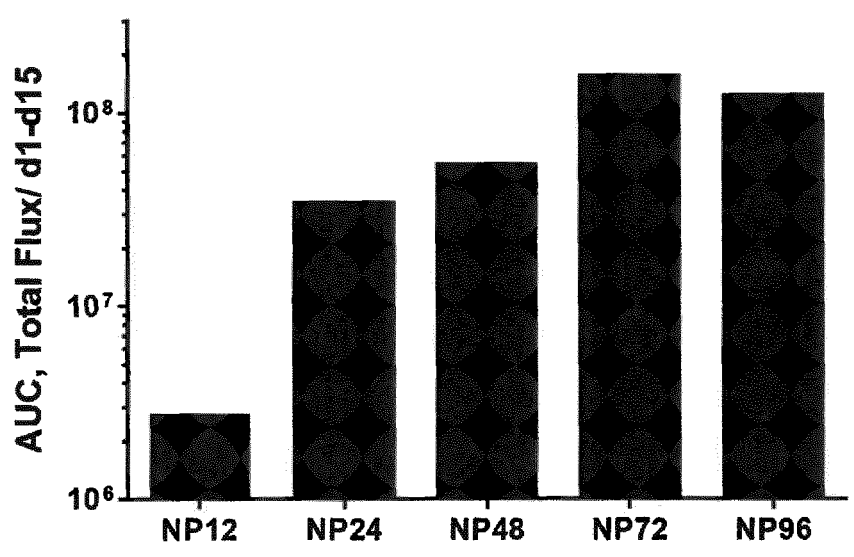
Bioluminesence signal
- saRNA/PEI-PLxes, AUC -

Figure 12
A
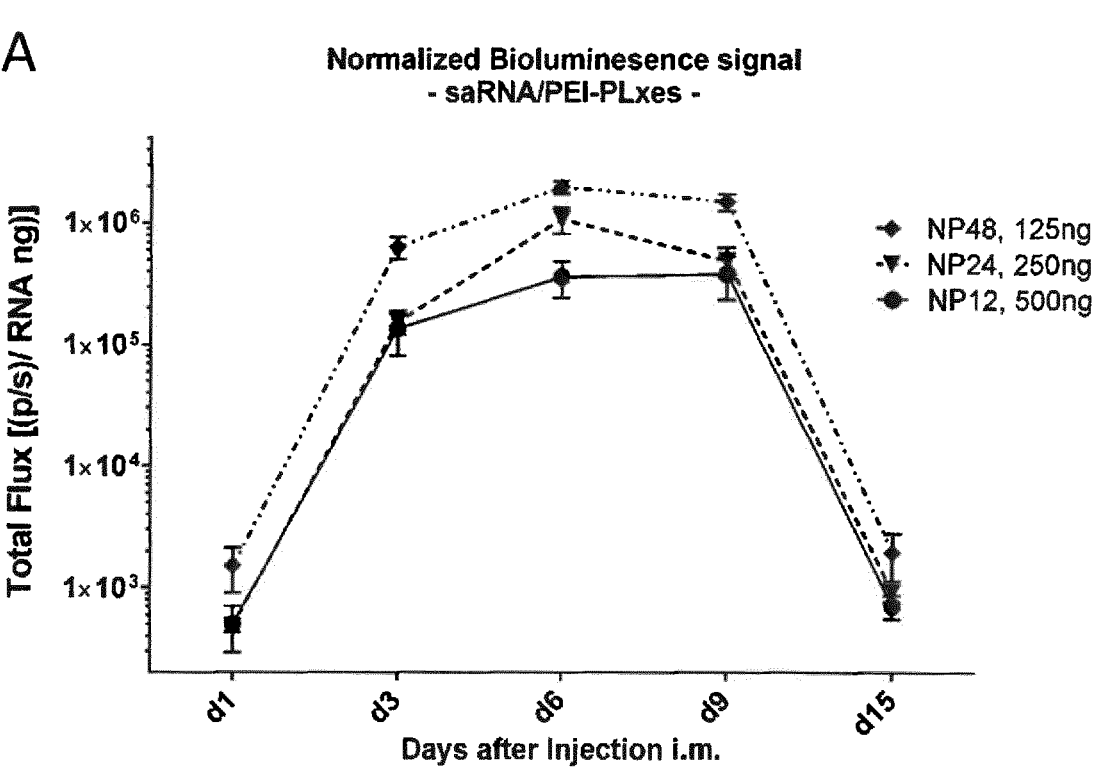
B
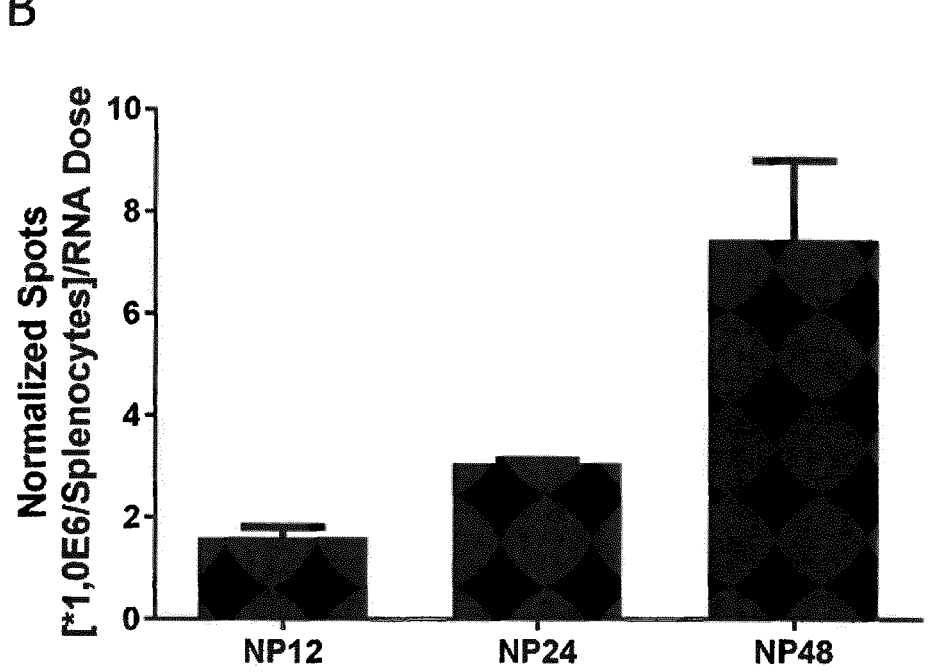

Figure 13
A
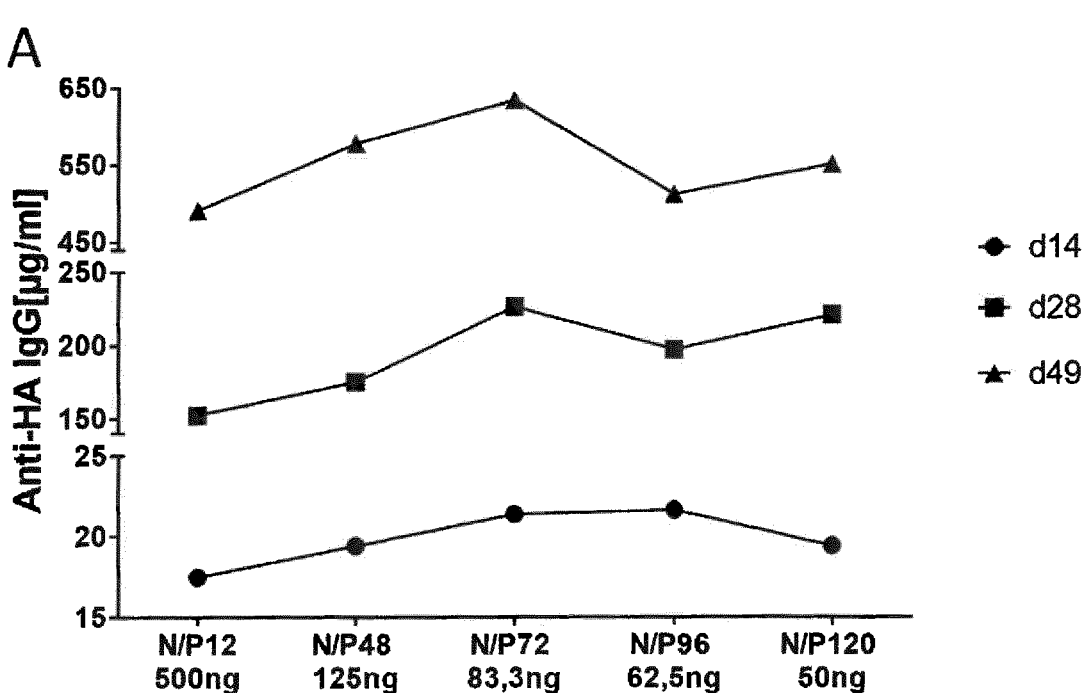
B
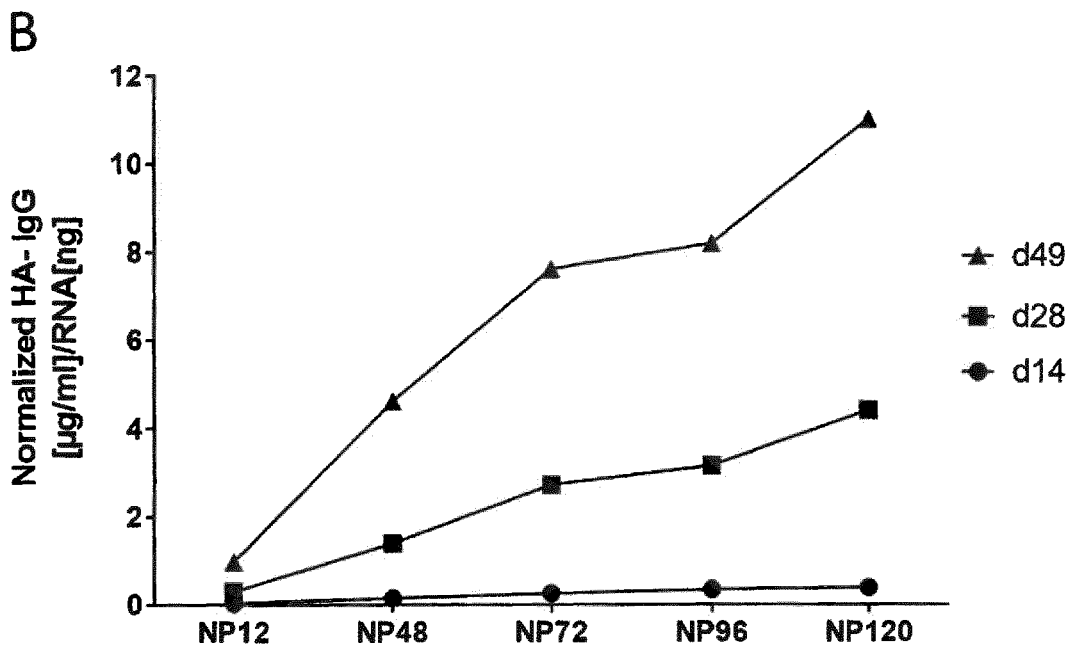

| PEI-Length (r.u) | Molecular Weight | PDI |
|---|---|---|
| 7 | 340 Da | <1,2 |
| 15 | 680 Da | <1,2 |
| 31 | 1400 Da | 1,04 |
| 62 | 2790 Da | 1,05 |
| 125 | 5630 Da | 1,09 |
| 250 | 11250 Da | 1,03 |
| 500 | 22500 Da | 1,04 |
| 1000 | 45000 Da | 1,09 |
| 1500 | 67500 Da | 1,15 |
| 2500 | 112500 Da | 1,2 |

Figure 15
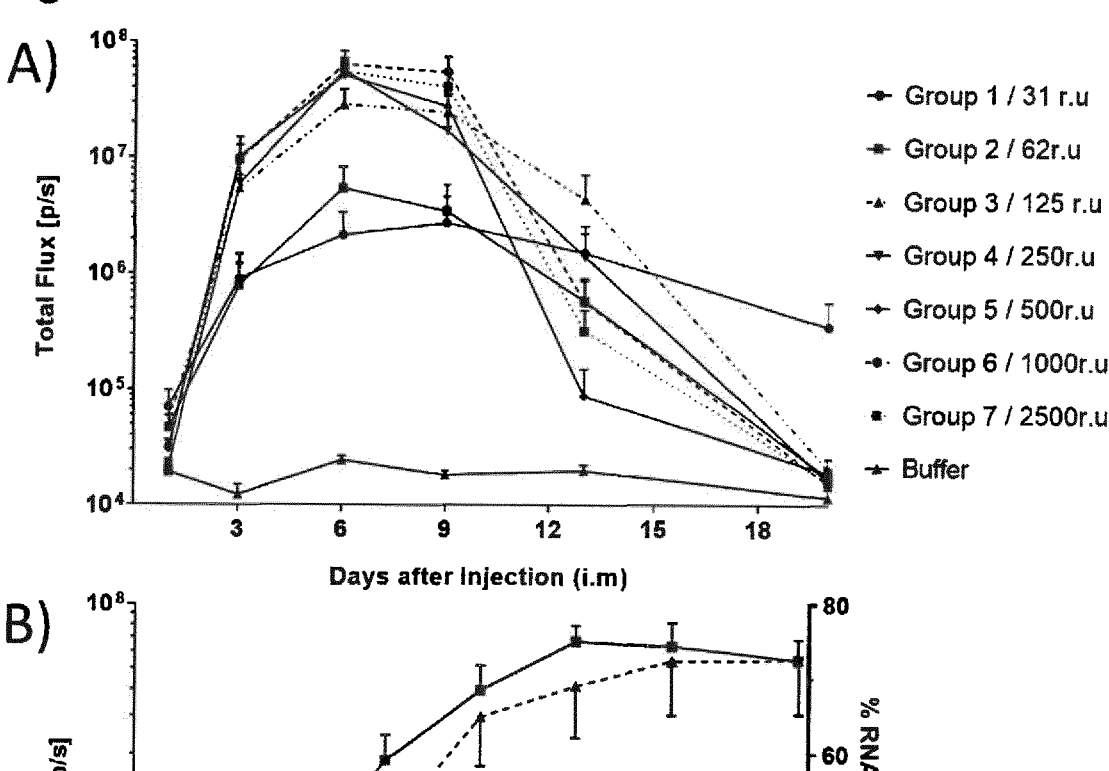
- Group 1 / 31 r.u
- Group 2 / 62r.u
- Group 3 / 125 r.u
- Group 4 / 250r.u
- Group 5 / 500r.u
- Group 6 / 1000r.u
- Group 7 / 2500r.u
- Buffer
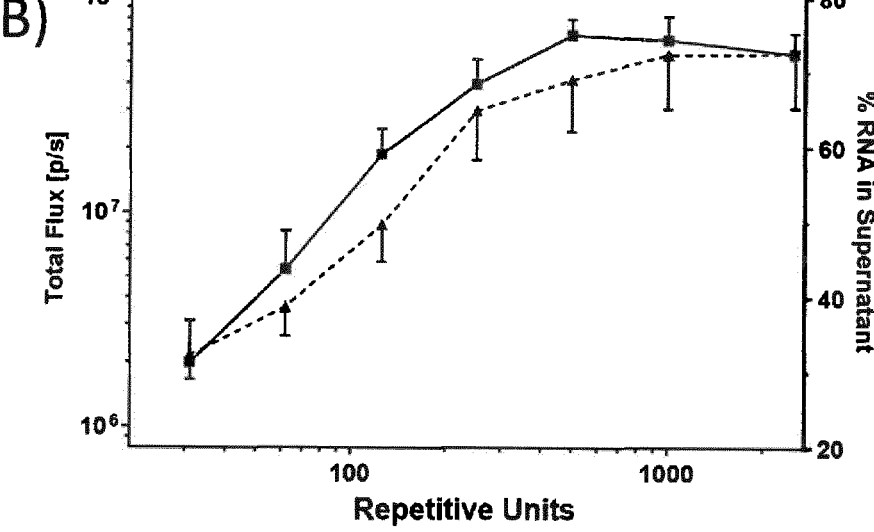
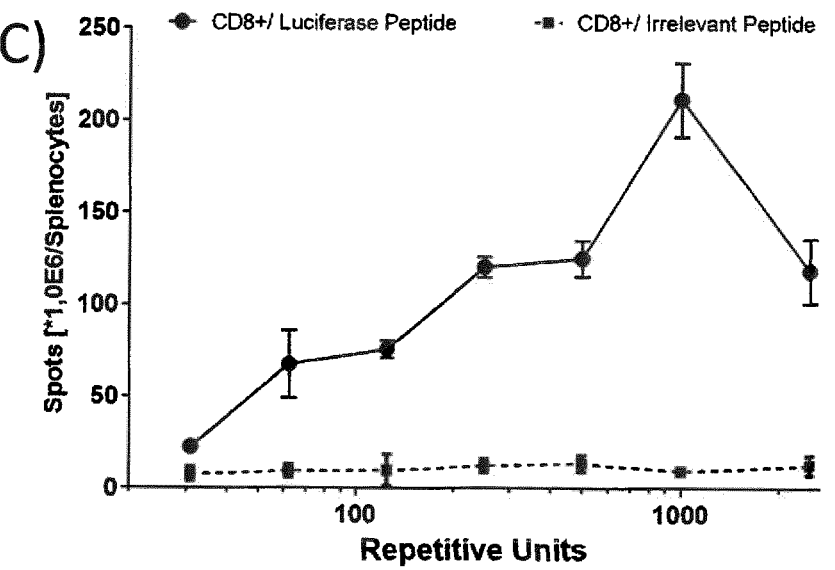
CD8+/ Luciferase Peptide        CD8+/ Irrelevant Peptide

Figure 19
A
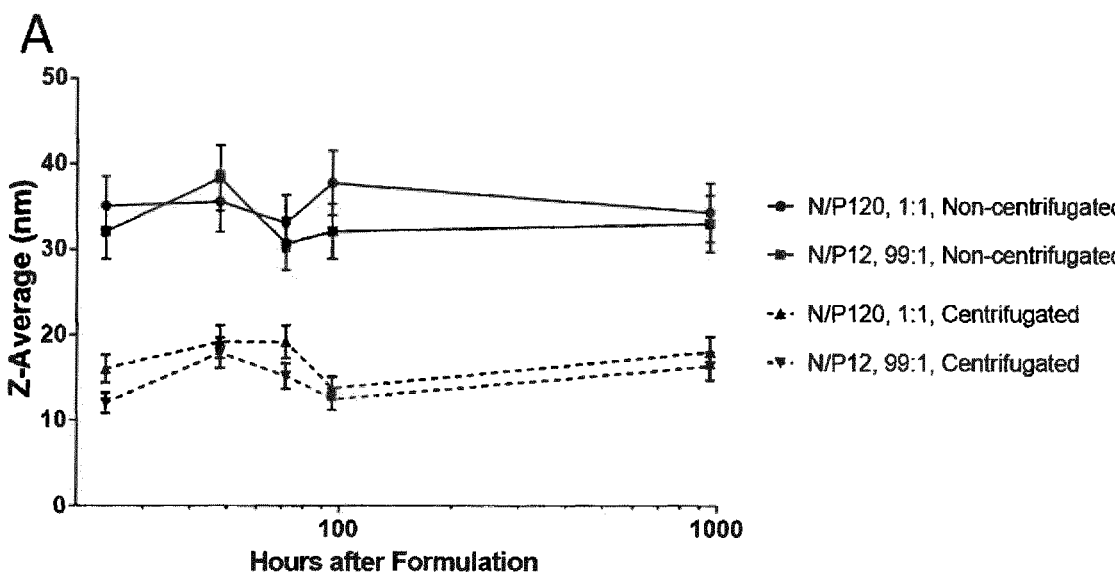
- N/P120, 1:1, Non-centrifugated
- N/P12, 99:1, Non-centrifugated
- N/P120, 1:1, Centrifugated
- N/P12, 99:1, Centrifugated
B
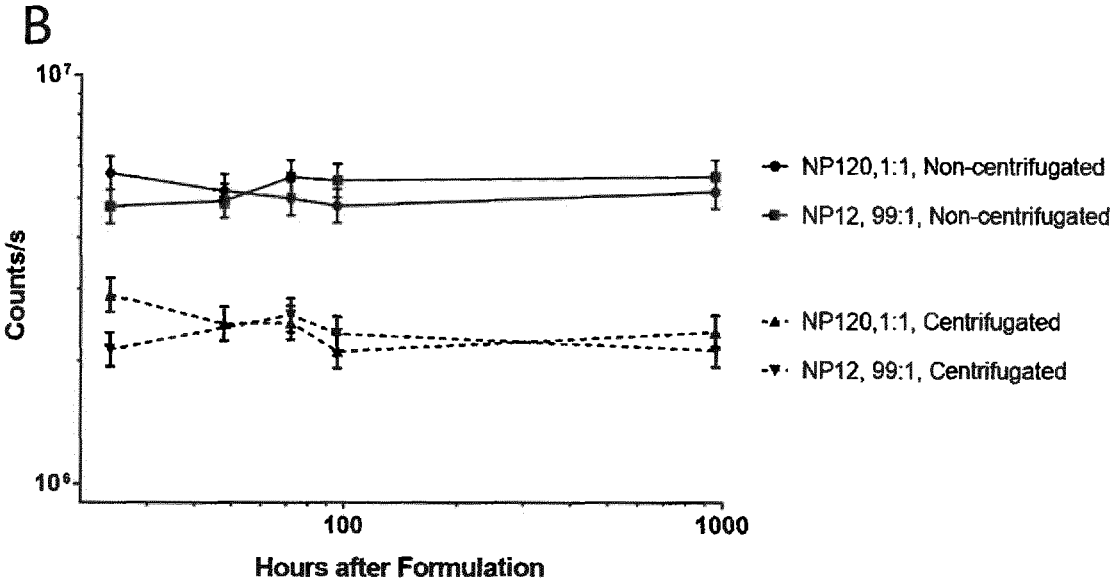
- NP120,1:1, Non-centrifugated
- NP12, 99:1, Non-centrifugated
- NP120,1:1, Centrifugated
- NP12, 99:1, Centrifugated

Figure 19
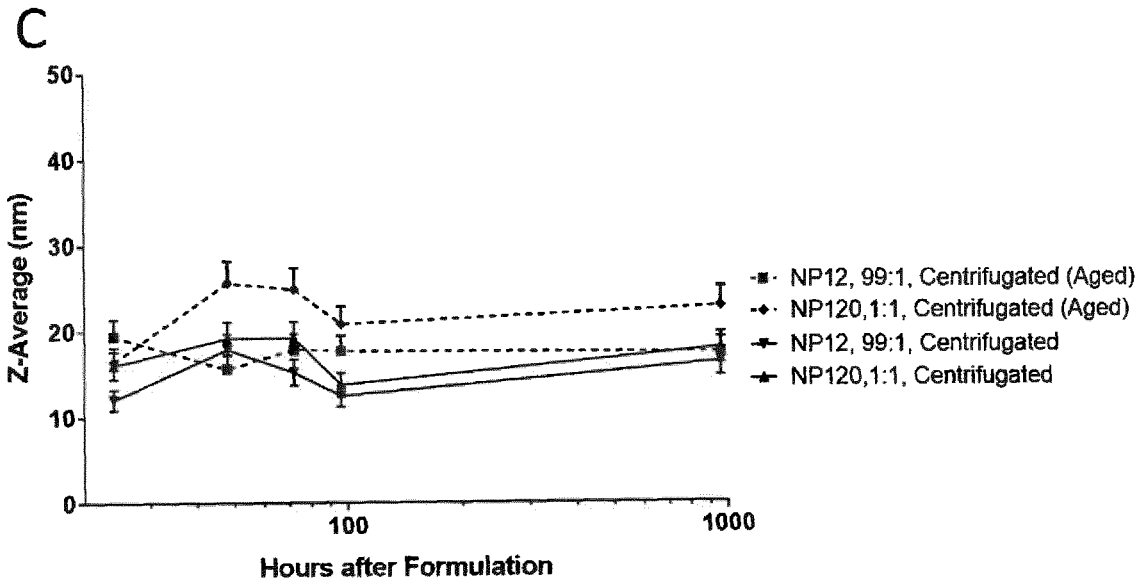
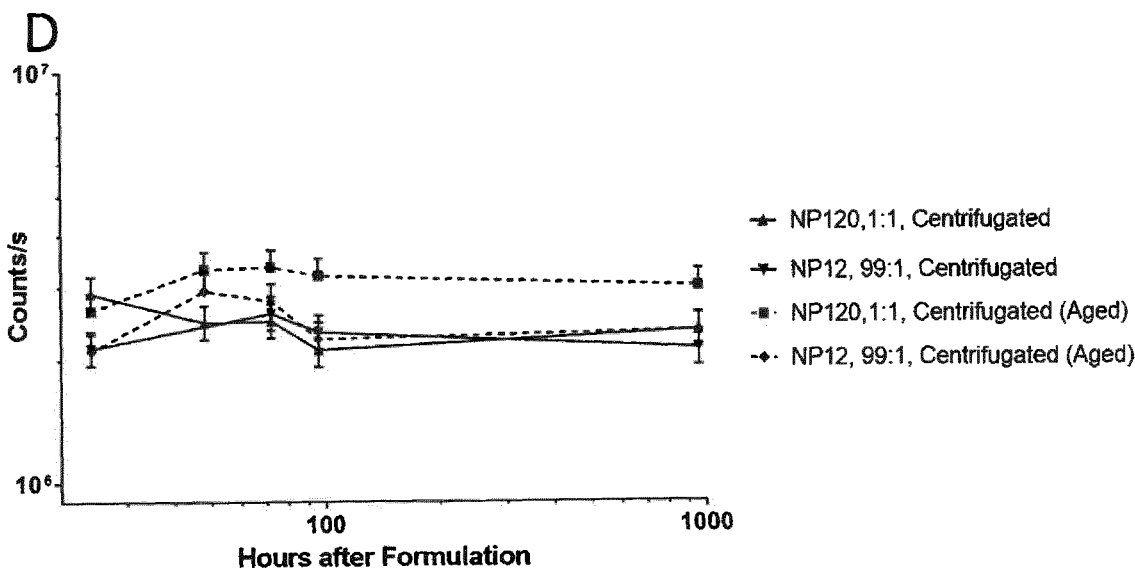

Figure 20
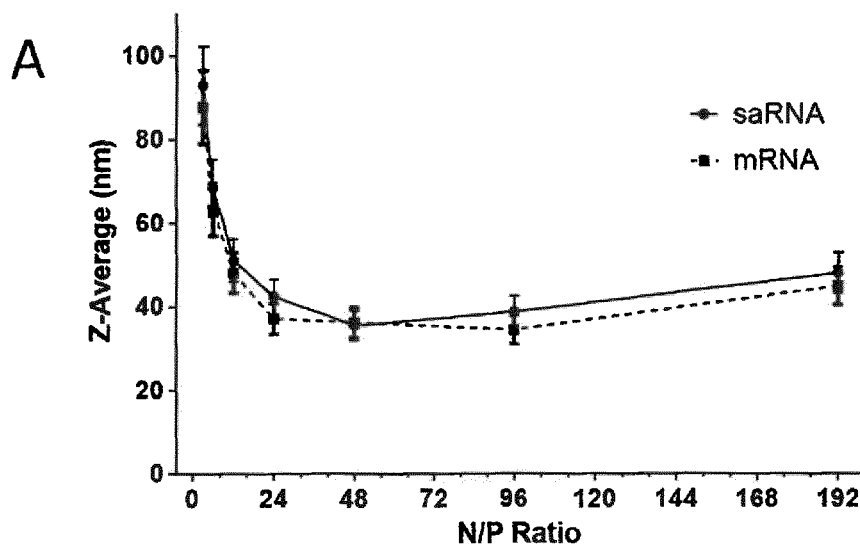
A
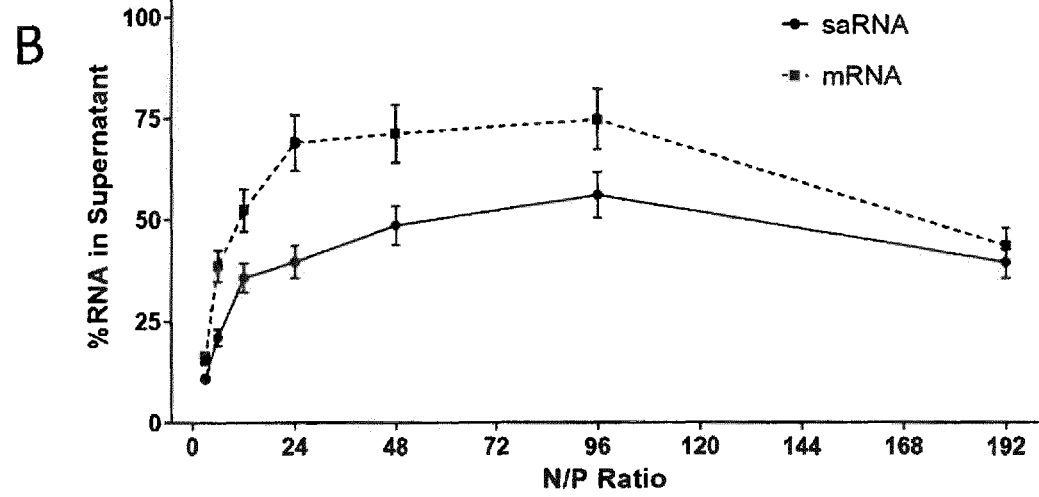
B
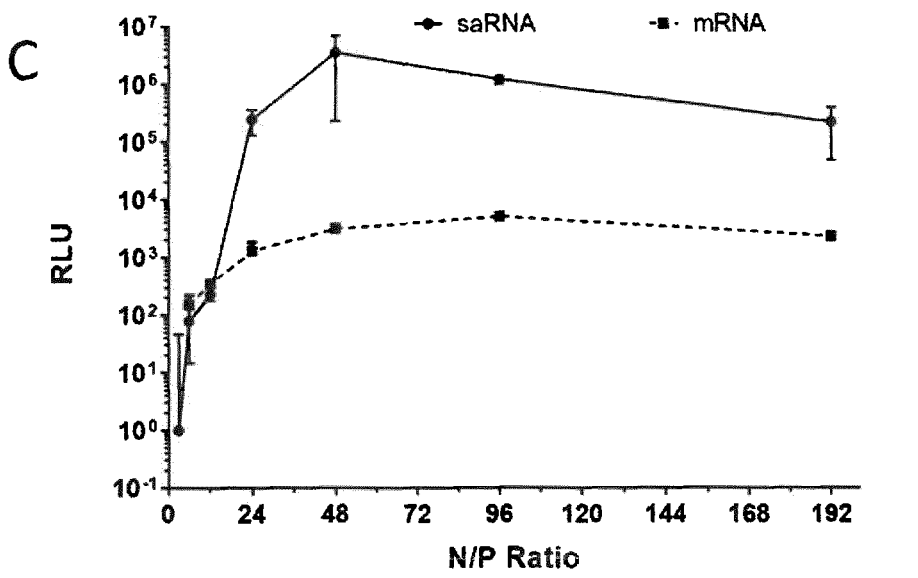
C

Figure 22
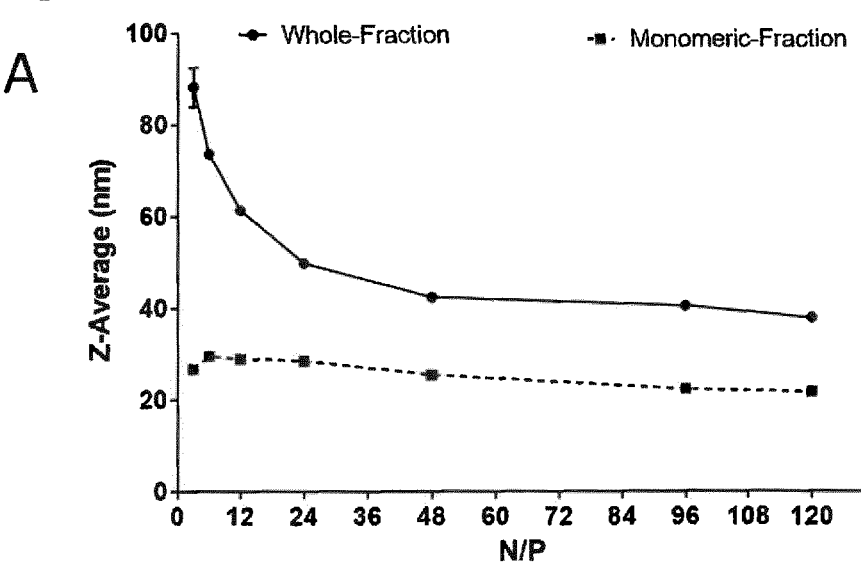
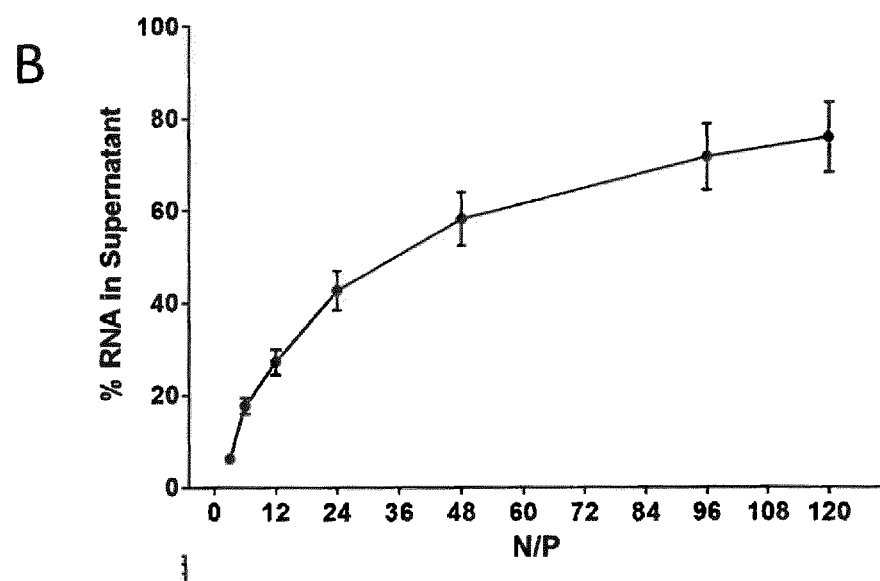
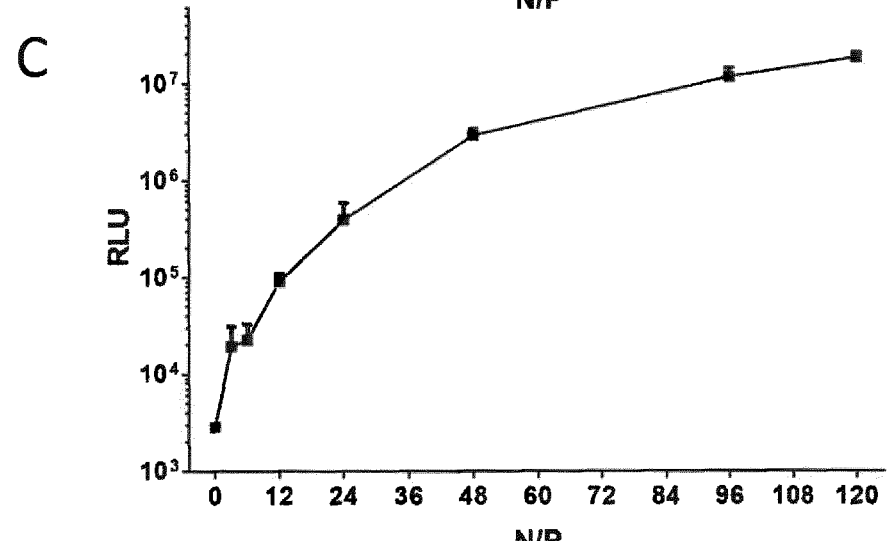

Figure 23
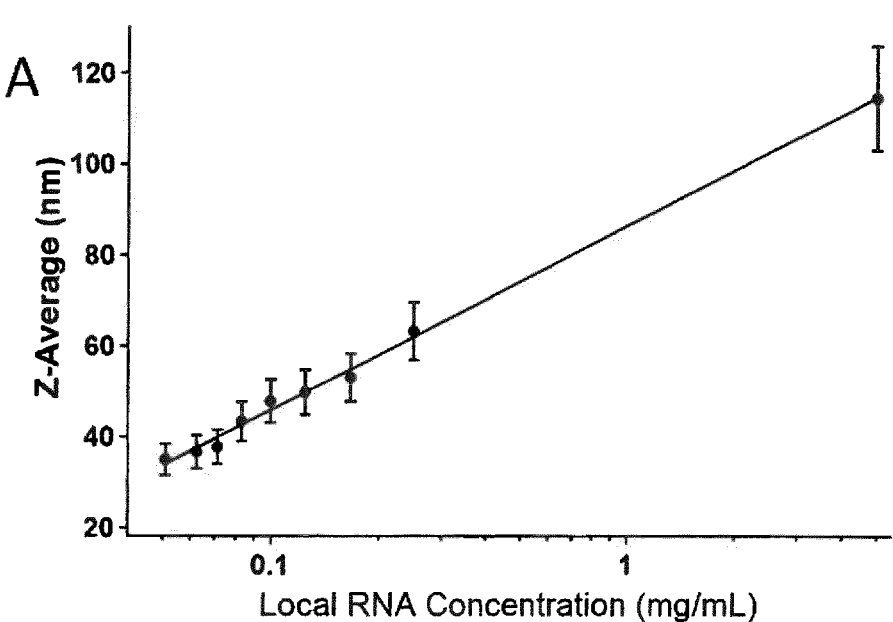
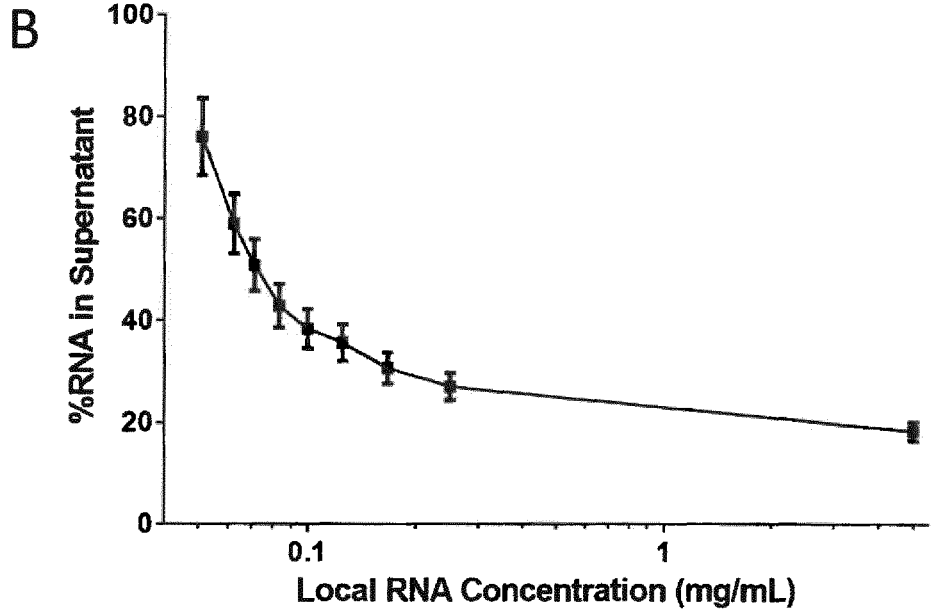

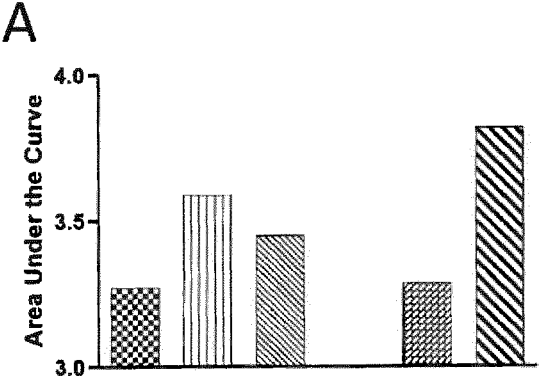

▨ Fresh- N/P12 (500ng)

▥ Fresh- N/P120 (125ng)

▨ Lyophilized Polyplexes-N/P120 (125ng)

▦ Lyophilized saRNA-ddH20 (N/P120, 125ng)

▧ Lyophilized saRNA- MBG ( N/P120,125ng)

▨ Lyophilized saRNA-MBS (N/P120, 125ng)

B

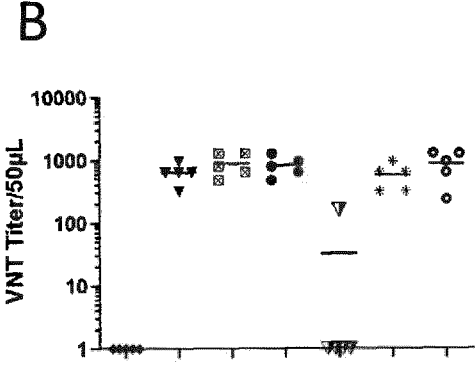

◆ MBG 5% Buffer

▼ Fresh- N/P12  500ng

▨ Fresh- N/P120  125ng

● Lyophilized Polyplexes- N/P120,125ng

▽ Lyophilized saRNA in ddH20: Reconstitution in N/P120, 125ng

✳ Lyophilized saRNA in MBG: Reconstitution in N/P120, 125ng

○ Lyophilized saRNA in MBS: Reconstitution in N/P120, 125ng

C

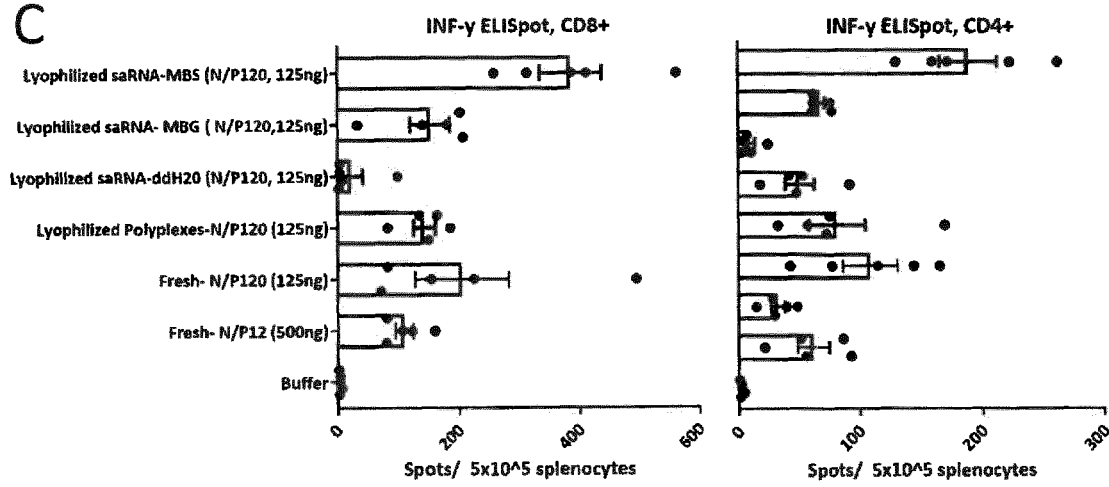

Figure 28
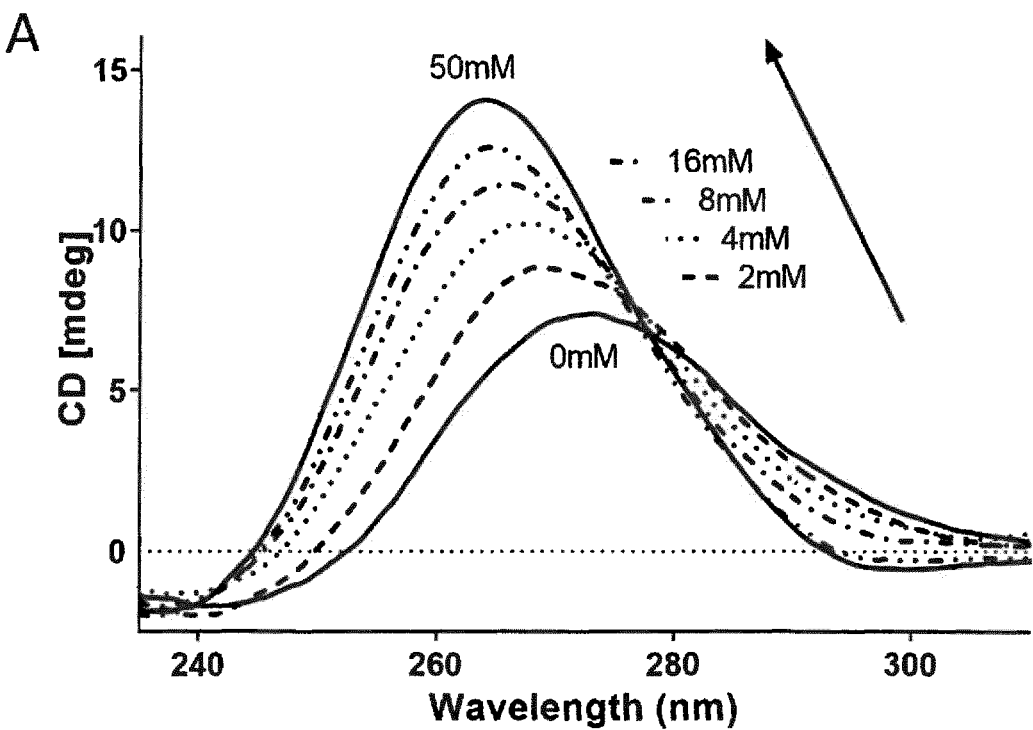
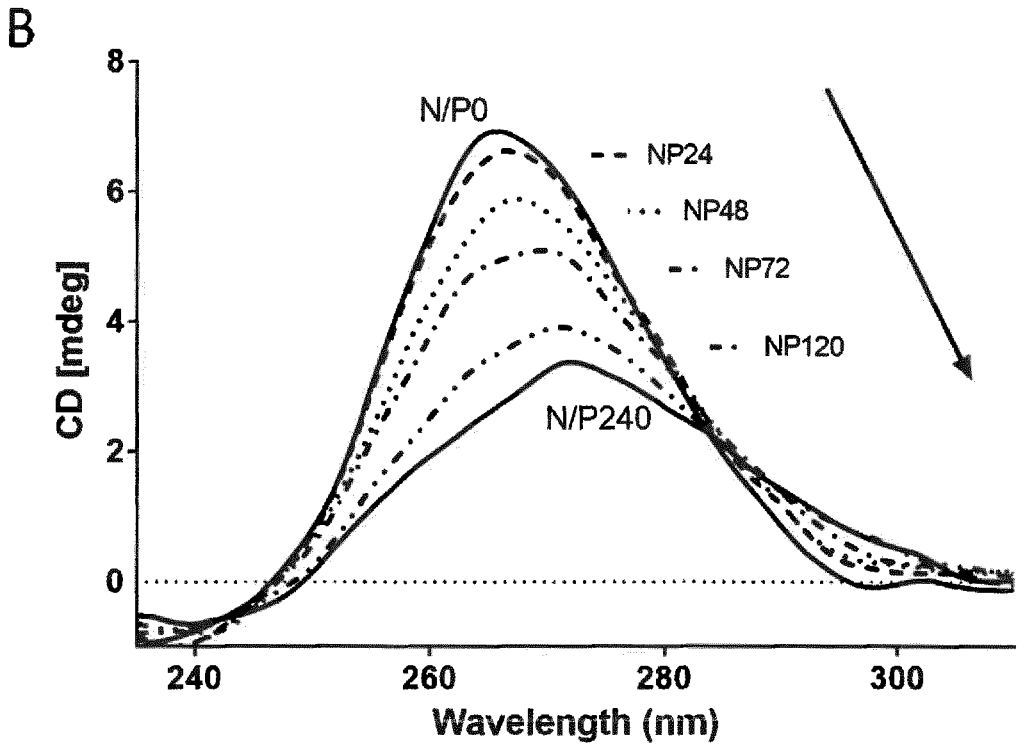

Figure 28
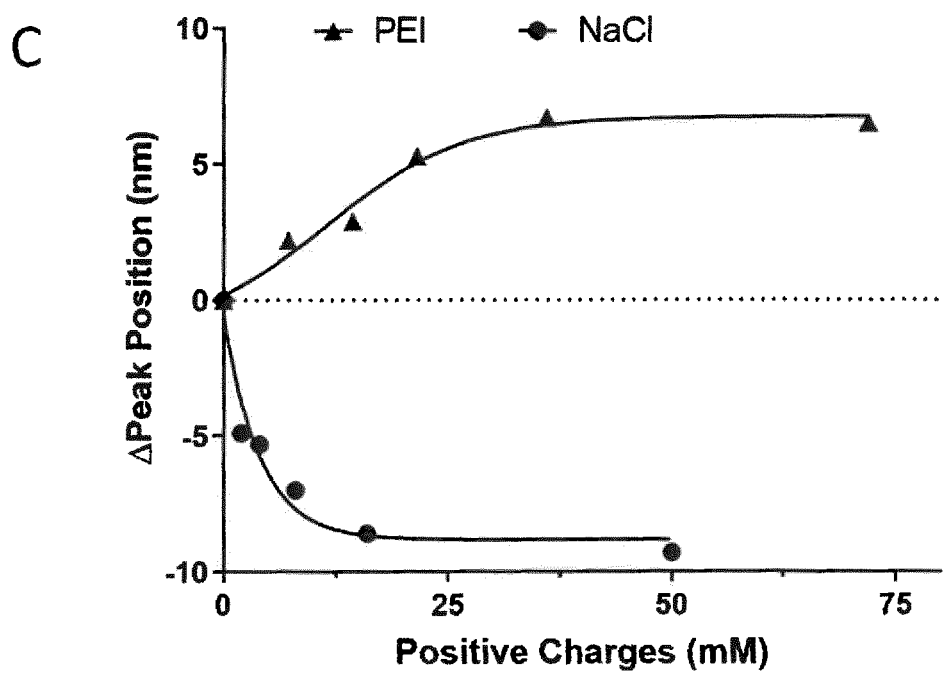
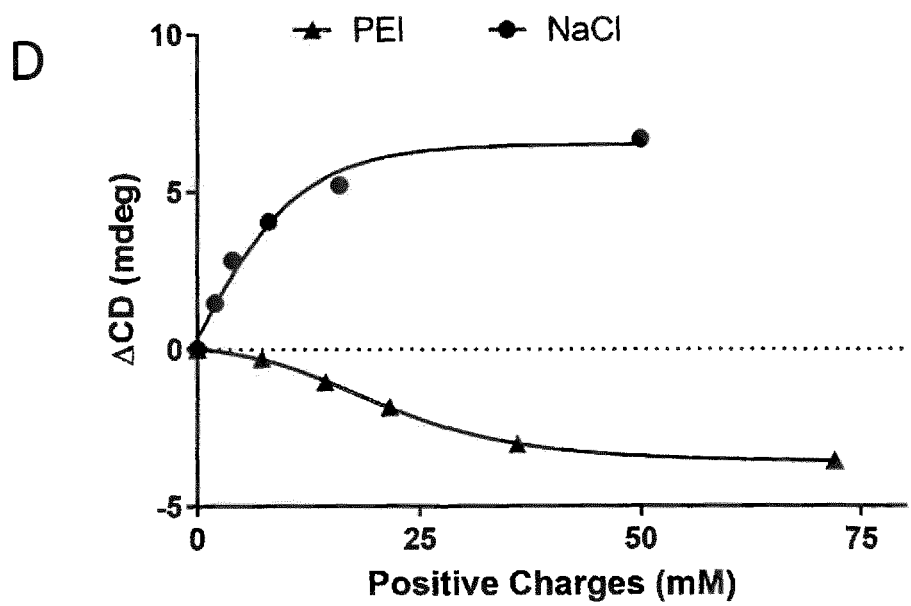

RNA FORMULATIONS SUITABLE FOR THERAPY

TECHNICAL FIELD

The present invention relates to compositions comprising RNA, preferably messenger RNA (mRNA), more preferably self-amplifying RNA (saRNA), and polymers, in particular cationic polymers, such as polyethylenimine (PEI), poly-L-Lysin (PLL), polyvinylamine (PVA) or polyallylamine (PAA), where individual RNA molecules are present in solution. In the formulations, the RNA is preferentially present in the form of monomers, dimers, trimers or oligomers, but not as aggregates comprising a large number of RNA molecules per aggregate, in particular large polyplex nanoparticles. The formulations can be formed from RNA and the polymer with a very high excess of polymer with respect to the RNA. Furthermore, the formulations can be formed at very low concentration of RNA. The formulations display improved transfection efficacy and they can be used for delivery of RNA to a subject, where they have an improved dose response relationship in comparison to formulations where large aggregates in the form of polyplex nanoparticles are present. More precisely, the present invention relates to formulations for administration of RNA, preferably messenger RNA (mRNA), more preferably self-amplifying RNA (saRNA), allowing a reduced effective dosing accompanied by a significantly reduced side effect risk. RNA-polymer formulations described herein are in particular useful for vaccination of humans or animals, e.g. against infectious diseases.

BACKGROUND

The use of RNA for delivery of foreign genetic information into target cells offers an attractive alternative to DNA. The advantages of using RNA include transient expression and a non-transforming character. RNA does not need to enter the nucleus in order to be expressed and moreover cannot integrate into the host genome, thereby eliminating the risk of oncogenesis. Therapeutic approaches based on messenger RNA (mRNA) are gaining increasing attention for application in various fields such as vaccination, tumor therapy or protein replacement (Sahin et al. (2014) Nat. rev. 13(10):759-780). Several mRNA based drugs for cancer vaccination have been brought into clinical trials. For translation of such novel therapeutic concepts into clinical practice, suitable formulations for administration to patients are necessary. The mRNA needs to be protected from rapid degradation by RNAses and cellular delivery to the target site and translation of the encoded proteins must be enabled. Traditional vehicles for nucleotide delivery are based on cationic lipids or cationic polymers, which form nanoparticle formulations with the mRNA. Regarding the polymeric delivery vehicles, polyethylenimine (PEI) and derivatives thereof are among the most established carrier systems (Neuberg, et al. (2014) Adv. in Gen. 88:263-88) and is already used in clinical trials for various applications.

Cationic polymers such as PEI are known to self-assemble with mRNA to nanoparticulate complexes with controlled transfection characteristics, and, in fact, PEI polyplex formulations are widely used for gene delivery. PEI is a cationic polymer composed of repetitive units of one amine group and a two carbon aliphatic spacer. PEI-based homopolymers can be classified according to its structure and size. A wide range of molecular weights (600 Da-400 kDa) for both the linear and branched form are available. On the structural level, the main difference between linear and branched PEI relays in the type of amines: linear PEI contains only secondary amines while branched PEI contains a ratio of 25/50/25 primary/secondary/tertiary amines. PEI is well soluble in water at RT, protonated in aqueous buffers but also soluble in organic solvents such as methanol, ethanol or chloroform.

The outstanding properties of PEI as a non-viral delivery system rest precisely upon the iminoethylene monomers, which define the high density of cationic charges. The protonated amines in the polymer can form electrostatic bonds with the anionic charges present in nucleic acids, mainly due to the phosphate back bone present in both DNA and RNA.

One important characteristic of PEI polyplex formulations is the so-called N/P ratio, which gives the ratio of the nitrogen groups in the PEI to the number of phosphate groups in the RNA. It is correlated to the charge ratio, as the nitrogen atoms (depending on the pH) are usually positively charged and the phosphate groups are negatively charged. The N/P ratio, where a charge equilibrium exists, depends on the pH. At applicable pH the charge equilibrium is achieved by use of N/P ratios between one and four. Therefore PEI formulations are frequently formed at N/P ratios larger than four up to twelve, because positively charged nanoparticles are considered favorable for transfection. In that case, RNA is considered to be completely bound to PEI nanoparticles, and further to the nanoparticles free excess PEI is considered to be present. According to some publications, free PEI is favorable for transfection by the nanoparticles potentially because the PEI can be involved in the cellular uptake mechanism and release from the endosomal compartments (Boeckle et al. (2004) J Gene Med. 6, 1102-1111; Cai et al. (2016) J Cont. Rel. 238, 71-79; Florea et al. (2002) AAPS 4, 1-11).

The development of formulations for the delivery of biologically active RNA with improved safety and efficacy is still an unmet need. Thus, there is a need of providing formulations for the efficient delivery of biologically active RNA to target cells or target tissue where the delivered RNA is translated into the peptide or protein it codes for.

SUMMARY

Formulations of RNA with cationic polymers are described herein, where the RNA is predominantly present in the form of monomers, dimers, trimers or oligomers, but not or not significantly as aggregates comprising a large number of RNA molecules per aggregate, in particular polyplex nanoparticles, which are much larger than an individual RNA molecule, and which comprise a higher number of RNA copies. Surprisingly it was found, that such phases can be formed by adding a very large excess of cationic polymer (in terms of charge ratio) to the RNA, and/or by forming the formulations at very low concentration of the RNA.

The usual understanding of formulations comprising RNA and cationic polymers is, that so-called polyplex nanoparticles are formed, which may exist in a size range from about 100 nm or below, to several hundreds of nanometers. One frequent parameter for these nanoparticles is the so called N/P ratio, which gives the charge ratio between the positively charged nitrogen groups in the polymer and the negatively charged phosphate groups of the RNA. In case of excess of polymer, the RNA is considered to be completely bound to the nanoparticles, and the excess polymer is thought to be present in the free aqueous phase. In some publications this excess free polymer is considered to be advantageous for the transfection efficacy of the polyplex nanoparticles.

Here, a new phase, further to the previously known polyplex nanoparticles, is described. It was found that, by addition of increasing excess of polymer to RNA at a concentration of about 0.1 mg/ml, a phase of individual RNA molecules, present as monomers, dimers, trimers or oligomers is formed, where the equilibrium between oligomers and monomers is shifted towards monomers by adding increasing excess of polymer. At 0.05 mg/ml or lower RNA concentration, a lower excess of PEI is required to form the new phase. For example, in case of polyethylenimine (PEI) the RNA monomers are the predominant form at N/P ratios of about 70 to 120 and above when the RNA concentration is 0.1 mg/ml. In case the RNA concentration is only 0.05 mg/ml and preferably the RNA:PEI mixing ratio is >1:1, an excess of PEI according to an N/P ratio of 4, preferentially 12 is sufficient. Without wishing to be bound by theory, it is believed that individual RNA molecules are associated in a stoichiometric manner with polyethylenimine, leading to distinct molar masses of the monomers, dimers, trimers, etc. The RNA in a composition comprising PEI can be identified by different physicochemical techniques, and it can be also physically separated from coexisting polyplex nanoparticles. Surprisingly it was found, that the RNA in the monomeric or oligomeric form in the PEI containing composition has a much higher transfection efficacy than the classically known polyplex nanoparticles. Highest transfection efficacy was found if the RNA was present completely in the monomeric form (in case of RNA PEI formulations formed at a concentration of 0.1 mg/mL and at a N/P ratio of about 70-120).

The phase of individual RNA molecules demonstrated superior transfection efficacy in vitro and in vivo, as demonstrated by observation of reporter gene expression (luciferase, green fluorescent protein). They are applicable for use as vaccine formulations, e.g. for intramuscular application, in order to obtain improved titers of antigens.

The new phase of RNA molecules in a polymer containing composition can be easily formed by adding a suitable amount of polymer to the RNA at a suitable concentration, suitable mixing ratio and suitable buffer conditions. The phases are advantageous for pharmaceutical use because they can be easily manufactured to controlled structural characteristics, and there is no risk of large particle formation or aggregation.

The new phase of RNA in a polymer containing composition can be formed by adding a solution of polymer to a solution of RNA, or by dissolving dehydrated (lyophilized) RNA with the polymer solution. Thus pharmaceutical manufacturing and control of products on this basis is greatly facilitated.

Pharmaceutical products based on the RNA phase for intramuscular, intradermal or subcutaneous application can be formed.

One aspect of the disclosure relates to a composition comprising RNA and a polymer in an aqueous phase, wherein the predominant fraction of the RNA molecules comprises individual molecules in solution. In one embodiment, the predominant fraction comprises more than 20%, more than 30%, more than 40%, more than 50%, more than 60%, more than 70%, more than 80%, more than 90%, more than 95%, more than 96%, more than 97%, more than 98%, or more than 99% of the total amount of RNA in the composition.

In one embodiment of any aspect described herein and other aspects, the disclosure relates to a composition comprising RNA and a polymer in an aqueous phase, wherein more than 20%, more than 30%, more than 40%, more than 50%, more than 60%, more than 70%, more than 80%, more than 90%, more than 95%, more than 96%, more than 97%, more than 98%, or more than 99% of the total amount of RNA in the composition is present as monomolecular species. In one embodiment of any aspect described herein and other aspects, the disclosure relates to a composition comprising RNA and a polymer in an aqueous phase, wherein more than 60%, more than 70%, more than 80%, more than 90%, more than 95%, more than 96%, more than 97%, more than 98%, or more than 99% of the total amount of RNA in the composition is RNA which is present as RNA monomers or oligomers with a number of four or less RNA molecules per oligomer unit.

In one embodiment of any aspect described herein and other aspects, the disclosure relates to a composition comprising RNA and a polymer in an aqueous phase, wherein more than 60%, more than 70%, more than 80%, more than 90%, more than 95%, more than 96%, more than 97%, more than 98%, or more than 99% of the total amount of RNA in the composition is RNA which does not precipitate when centrifuged at 20 000×g for 90 minutes.

In one embodiment of any aspect described herein and other aspects, the disclosure relates to a composition comprising RNA and a polymer in an aqueous phase, wherein less than 20%, less than 10%, less than 5%, less than 4%, less than 3%, less than 2%, less than 1%, or less than 0.5% of the total amount of RNA in the composition is RNA which is present as RNA polyplex nanoparticles of a size of more than 50 nm or 60 nm and/or present as RNA polyplex nanoparticles with a number of 10 or more, or 20 or more RNA copies per nanoparticle. In one embodiment, the composition is essentially free of RNA polyplex nanoparticles of a size of more than 50 nm or 60 nm and/or RNA polyplex nanoparticles with a number of 10 or more, or 20 or more RNA copies per nanoparticle.

In one embodiment of any aspect described herein and other aspects, the disclosure relates to a composition comprising RNA and a polymer in an aqueous phase, wherein less than 20%, less than 10%, less than 5%, less than 4%, less than 3%, less than 2%, less than 1%, or less than 0.5% of the total amount of RNA in the composition is RNA which is present as aggregates comprising a large number of RNA molecules per aggregate.

Compositions as described herein can be obtained by appropriately adjusting the amount of RNA and polymer, in particular by appropriately adjusting the NIP ratio.

In one embodiment of the compositions described herein, the majority of the RNA is present as monomolecular species. In different embodiments, more than 50%, more than 60%, more than 70%, more than 80%, more than 90%, more than 95%, more than 96%, more than 97%, more than 98%, or more than 99% of the total amount of RNA in the composition is present as monomolecular species.

In one embodiment of the compositions described herein, the polymer is a cationic polymer. In one embodiment of the compositions described herein, the polymer is a polycationic polymer. In one embodiment of the compositions described herein, the polymer comprises one or more selected from the group consisting of cationic or polycationic peptides or proteins, including protamine, spermin or spermidine, poly-lysine, poly-arginine, cationic polysaccharides, including chitosan, cationic polymers, including poly(ethyleneimine), poly(propyleneimine), polybrene, polyallylamines, and polyvinylamine. In one embodiment, the polymer comprises a polyamidoamine (PAMAM) polymer.

In one embodiment of the compositions described herein, the polymer comprises poly(ethyleneimine). In one embodiment of the compositions described herein, the poly(ethyleneimine) is a linear polymer. In one embodiment of the compositions described herein, the poly(ethyleneimine) is a branched polymer. In one embodiment of the compositions described herein, the poly(ethyleneimine) has a mean molar mass between 1000 Da and 150000 Da, between 5000 Da and 100000 Da, between 10000 Da and 50000 Da, between 15000 Da and 30000 Da, between 20000 Da and 25000 Da, or of about 22500 Da. In one embodiment of the compositions described herein, the poly(ethyleneimine) has a mean molar mass between 22500 Da and 150000 Da.

In one embodiment of the compositions described herein, the composition additionally comprising a buffering substance which may be selected from the group consisting of 4-(2-hydroxyethyl)-1-piperazineethanesulfonic acid (HEPES), 3-morpholino-2-hydroxypropanesulfonic acid (MOPSO), 2-(N-morpholino)ethanesulfonic acid (MES), Bis-tris buffering systems (e.g Bis-tris propane, Bis-tris methane), acetic acid buffering systems, other carboxylic acid buffering systems, phosphatic acid buffering systems, or citric acid buffering systems where the pH may be in the range from 4 to 8, more preferably from 5 to 7.

In one embodiment of the compositions described herein, the composition has an ionic strength of 50 mM or less, preferably wherein the concentration of positively charged monovalent ions is 25 mM or less and the concentration of free positively charged divalent ions is 20 µM or less. In one embodiment of the compositions described herein, the concentration of free positively charged divalent ions is 20 µM or less.

In one embodiment of the compositions described herein, the RNA predominantly consists of individually polymer-associated RNA molecules. In different embodiments, more than 50%, more than 60%, more than 70%, more than 80%, more than 90%, more than 95%, more than 96%, more than 97%, more than 98%, or more than 99% of the total amount of RNA in the composition is present as individually polymer-associated RNA molecules.

In one embodiment of the compositions described herein, the mass fraction of RNA present as RNA monomers or oligomers with a number of four or less RNA copies per oligomer unit is higher than 60%, higher than 70%, higher than 80%, higher than 90%, higher than 95%, higher than 96%, higher than 97%, higher than 98%, or higher than 99% of the total amount of RNA. In one embodiment of the compositions described herein, the composition essentially does not comprise RNA aggregates comprising a large number of RNA molecules per aggregate.

In one embodiment of the compositions described herein, the RNA is selected from the group consisting of mRNA, saRNA, siRNA, shRNA, miRNA, pre-miRNA, ribozyme, and antisense RNA.

In one embodiment of the compositions described herein, the composition does not comprise viral RNA particles.

In one embodiment of the compositions described herein, the composition is formed by mixing RNA and an excess of polymer.

In one embodiment of the compositions described herein, a polymer containing solution and a RNA containing solution are mixed, wherein the final concentration of RNA is 0.1 mg/ml or smaller and wherein the ratio of the number of the polymer nitrogen groups to phosphate groups of RNA (N/P) is at least about 48. In one embodiment, the number of polymer nitrogen groups to phosphate groups of RNA (N/P) ranges from about 48 to 300, about 60 to 200, or about 80 to 150.

In one embodiment of the compositions described herein, a polymer containing solution and a RNA containing solution are mixed and wherein the final concentration of RNA is 0.05 mg/ml or smaller and wherein the ratio of the number of the polymer to nitrogen groups to phosphate groups of RNA (N/P) is at least about 4. In one embodiment, the number of polymer nitrogen groups to phosphate groups of RNA (N/P) ranges from about 4 to 200, about 12 to 150, or about 24 to 120.

In one embodiment of the compositions described herein, a RNA containing solution is added to a polymer containing solution, wherein the volume of the RNA containing solution is equal to or exceeds the volume of the polymer containing solution, preferably the volume ratio of the a RNA containing solution to the polymer containing solution is between about 1:1 and 99:1.

In one embodiment of the compositions described herein, a RNA containing solution is added to a polymer containing solution, where the RNA containing solution has a concentration of RNA which is less than 2-fold of the concentration in the final composition, more preferably less than 1.5-fold of the concentration in the final composition, even more preferably less than 1.1-fold of the concentration in the final composition. In one embodiment of the compositions described herein, the RNA concentration in a mixture of the RNA containing solution added to a polymer containing solution is 0.5 mg/ml or lower, 0.4 mg/ml or lower, 0.3 mg/ml or lower, 0.2 mg/ml or lower, or 0.1 mg/ml or lower. In one embodiment of the compositions described herein, the RNA concentration in a RNA containing solution to be added to a polymer containing solution is 1 mg/ml or lower, 0.9 mg/ml or lower, 0.8 mg/ml or lower, 0.7 mg/ml or lower, 0.6 mg/ml or lower, 0.5 mg/ml or lower, 0.4 mg/ml or lower, 0.3 mg/ml or lower, 0.2 mg/ml or lower, or 0.1 mg/ml or lower.

In one embodiment of the compositions described herein, the composition is formed by mixing a solution of the RNA and a solution of the polymer.

In one embodiment of the compositions described herein, the composition is formed by mixing equal volumes of a solution of the RNA and a solution of the polymer.

In one embodiment of the composition described herein, the composition is formed by mixing a solution of the RNA and a solution of the polymer, in a volume mixing ratio of at least 4:1.

In one embodiment of the compositions described herein, the composition is formed by dissolving dehydrated RNA in a solution of the polymer.

It is demonstrated herein that RNA in a composition described herein displays a surprisingly compact organization and exhibits very high packing density.

In one embodiment of any aspect described herein and other aspects, the disclosure relates to a composition comprising RNA and a polymer in an aqueous phase, wherein the RNA is present in a highly compacted conformation, where the radius of gyration of the RNA, such as obtainable from small angle X-ray scattering measurements is smaller than the radius of gyration of the RNA in 50 mM NaCl solution.

In one embodiment of any aspect described herein and other aspects, the disclosure relates to a composition comprising RNA and a polymer in an aqueous phase, wherein the RNA is present in a highly compacted conformation, where the radius of gyration of the RNA, such as obtainable from small angle X-ray scattering measurements is not more than 80% of the radius of gyration of the RNA in 50 mM NaCl solution, preferably not more than 60% of the radius of gyration of the RNA in 50 mM NaCl solution, preferably not more than 60% of the radius of gyration of the RNA in 50 mM NaCl solution, preferably not more than 50% of the radius of gyration of the RNA in 50 mM NaCl solution, preferably not more than 40% of the radius of gyration of the RNA in 50 mM NaCl solution.

In one embodiment of any aspect described herein and other aspects, the disclosure relates to a composition comprising RNA and a polymer in an aqueous phase, wherein the RNA is present in a highly compacted conformation, where the ratio between radius of gyration, $R_g$, of the RNA (in nm), such as obtainable from small angle X-ray scattering measurements, and the cubic root of the molar mass of the RNA Mw, in Daltons, can be described by the following formula:

$$\frac{R_g}{\sqrt[3]{M_w}} \leq x,$$

wherein x s 0.17 $nm*mol^{1/3}*g^{-1/3}$, preferably 0.15 $mol*mol^{1/3}*g^{-1/3}$, more preferably 0.13 $nm*mol^{1/3}*g^{-1/3}$, more preferably 0.11 $nm*mol^{1/3}*g^{-1/3}$, more preferably 0.09 $nm*mol^{1/3}*g^{-1/3}$ or even more preferably 0.085 $nm*mol^{1/3}*g^{-1/3}$. For example, for an RNA with a molar mass of $3*10^6$ Da, having a $R_g$ of about 12 nm, the ratio would be about 0.083 $nm*mol^{1/3}*g^{-1/3}$.

One aspect of the disclosure relates to a composition comprising RNA and polymer described herein that has been lyophilized. Such lyophilized composition may be reconstituted by adding an aqueous solution to yield a composition comprising RNA and polymer described herein.

One aspect of the disclosure relates to a composition described herein for use in non-viral gene delivery. In one embodiment, gene delivery is to be effected into a cell, wherein the cell may be present in vitro, ex vivo or in vivo, e.g., in a subject.

One aspect of the disclosure relates to a method of transfecting a cell comprising contacting the cell with a composition described herein. In one embodiment, the cell may be present in vitro, ex vivo or in vivo, e.g., in a subject.

In one embodiment, the cell to which a gene is to be delivered or which is to be transfected is in a subject and the method comprises administering the composition described herein to the subject. In one embodiment, administration is by injection. In one embodiment, the composition is administered intramuscularly, intradermally or subcutaneously.

BRIEF DESCRIPTION OF THE DRAWINGS

FIG. 1: Characterization of classical mRNA/PEI and saRNA/PEI Polyplex-Populations iVT mRNA or saRNA was complexed at different N/P ratios between 0-12 in MBG buffer (final concentration 5% w/v Glucose, 10 mM MES, pH 6.1). FIG. 1A shows quantified amounts of free RNA over the total amount of RNA complexed at different N/P ratios in 3 independent experiments (n=3) with two technical duplicates for each measurements (x=2). FIG. 1B represents the average diameter of saRNA and iVT/PEI Polyplexes at different N/P Ratios measured by DLS in 3 independent experiments (n=3) with two technical duplicates for DLS measurements (x=2).

FIG. 2: Quantification of mRNA in saRNA/PEI Polyplex-Populations after centrifugation iVT mRNA or saRNA was complexed at different N/P ratios between 9-36 in MBG buffer (final concentration 5% w/v Glucose, 10 mM MES, pH 6.1). Formulation was fractionated by centrifugation (20.000 G, 4° C., 90') to purify RNA in supernatant. N/P ratio is calculated based on the PEI:RNA charge ratios. RNA concentration in each fraction is determined by UV-absorption measurement in the 260 nm wavelength, but also taking into account purity ratios 260/230 and 260/280 nm. FIG. 2A indicates RNA % over the total found in the different fractions of iVT mRNA/PEI-polyplexes upon increment of the N/P of the formulation in 5 independent experiments (n=5) with two technical duplicates for UV measurements (x=2). FIG. 2B indicates RNA % over the total found in the different fractions of saRNA/PEI-polyplexes upon increment of the N/P of the formulation in 5 independent experiments (n=5) with two technical duplicates for UV measurements (x=2).

Figure 3:
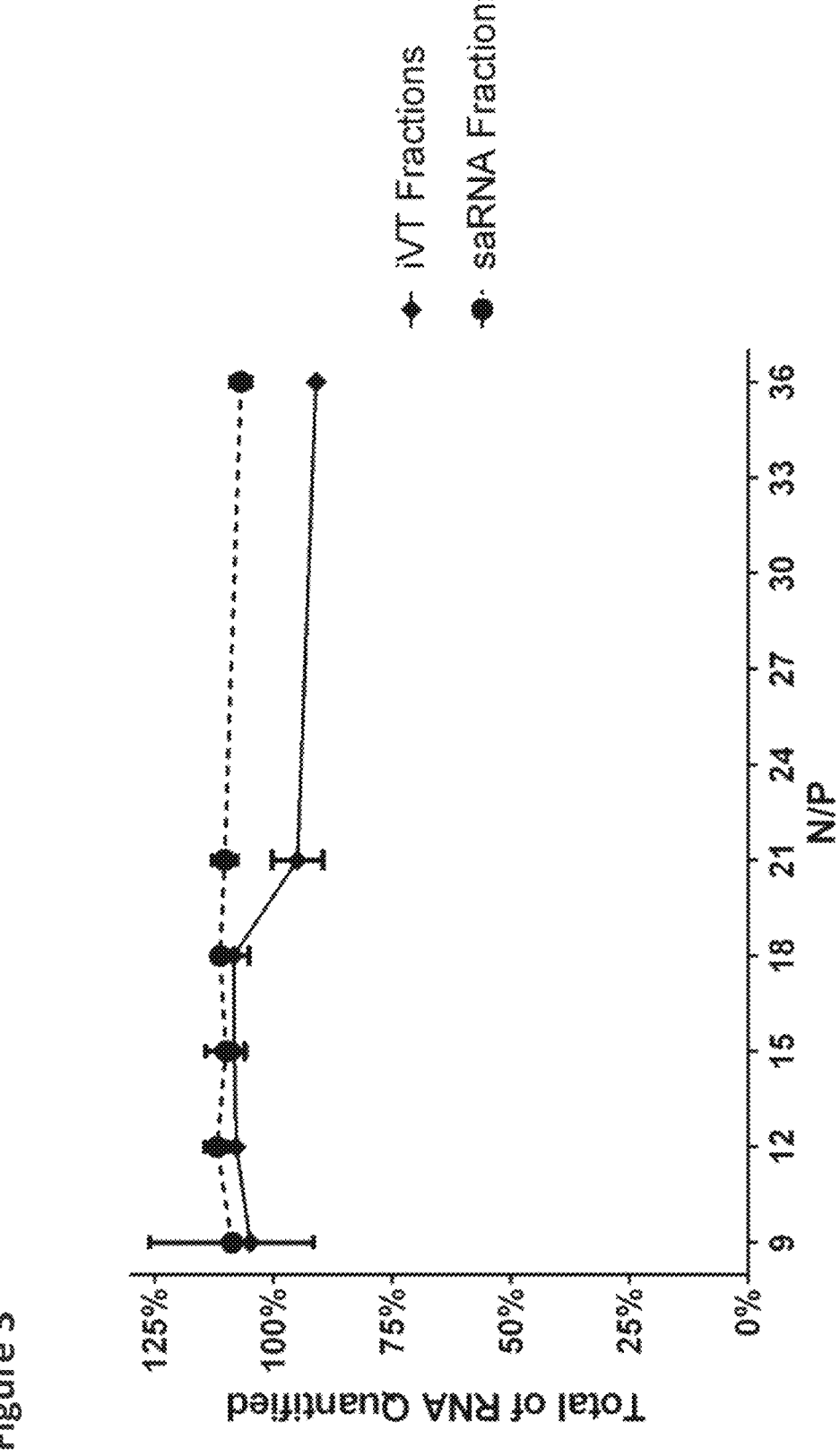

FIG. 3: Control—Total of precipitated mRNA and mRNA in the supernatant after centrifugation iVT mRNA or saRNA was complexed at different N/P ratios between 9-36 in MBG buffer (final concentration 5% w/v Glucose, 10 mM MES, pH 6.1). Formulation was fractionated by centrifugation (20.000 G, 4° C., 90') to purify RNA in supernatant. N/P ratio is calculated based on the in PEI:RNA charges ratio. RNA concentration in each fraction is determined by UV-absorption measurment in the 260 nm wavelength, but also taking into account purity ratios 260/230 and 260/280 nm. FIG. 3 indicates the sum of the quantified RNA contained in supernatant and pellet as percentage of the total concentration in the non-centrifugated control for the previous datasets in FIG. 2A and FIG. 2B.

Figure 4:
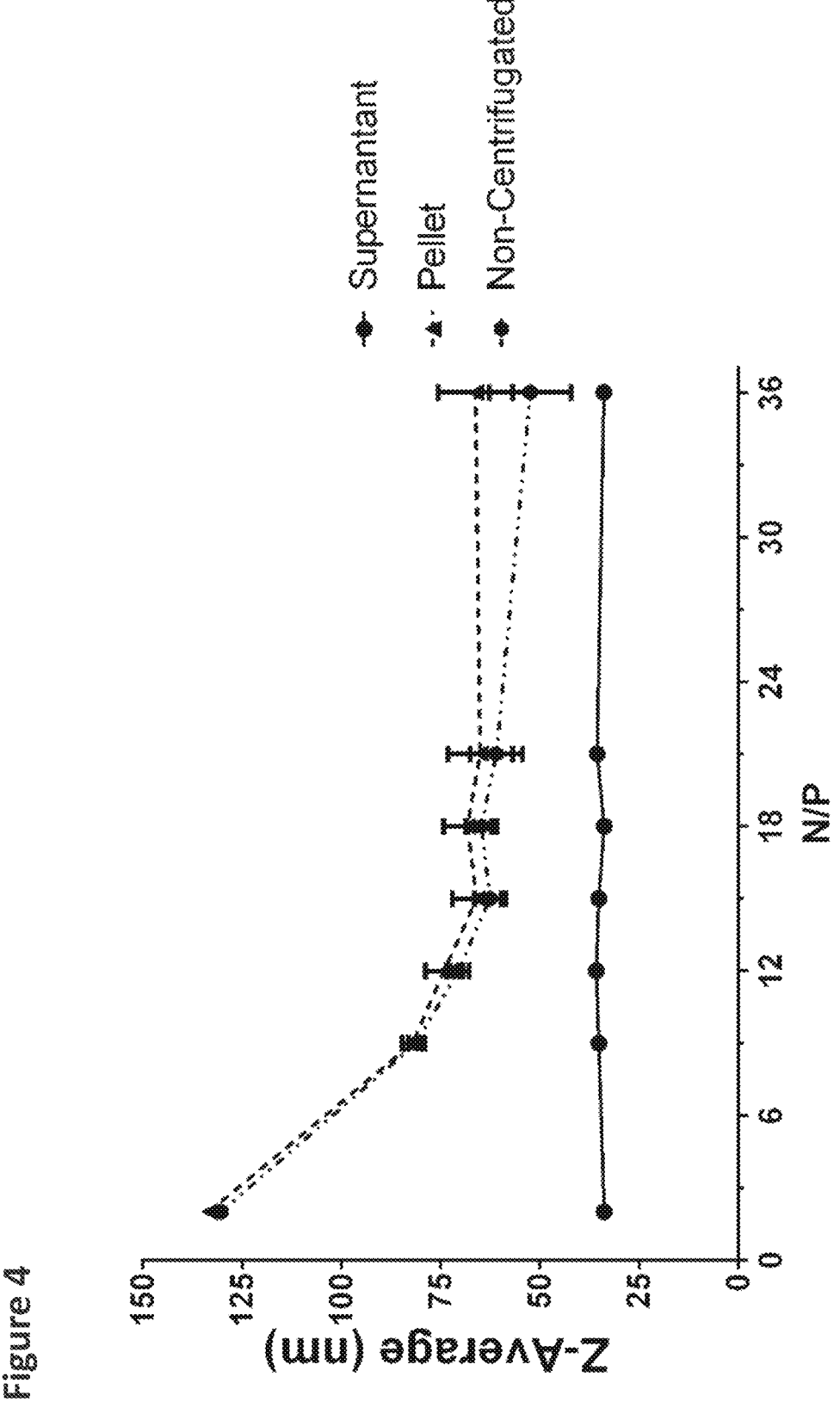

FIG. 4: Size of mRNA and saRNA/PEI Polyplex-Populations by DLS iVT mRNA or saRNA was complexed at different N/P ratios between 9-36 in MBG buffer (final concentration 5% w/v Glucose, 10 mM MES, pH 6.1). Formulation was fractionated by centrifugation (20.000 G, 4° C., 90') to purify RNA in supernatant. N/P ratio is calculated based on the PEI:RNA charges ratio. RNA concentration in each fraction is determined by UV-absorption measurement in the 260 nm wavelength, but also taking into account purity ratios 260/230 and 260/280 nm. FIG. 4 represents the average diameter of saRNA/PEI Polyplexes at different N/P Ratios measured by DLS after fractionation by centrifugation of the sample in 5 independent experiments (n=5) with two technical duplicates for DLS measurements (x=2).

Figure 5:
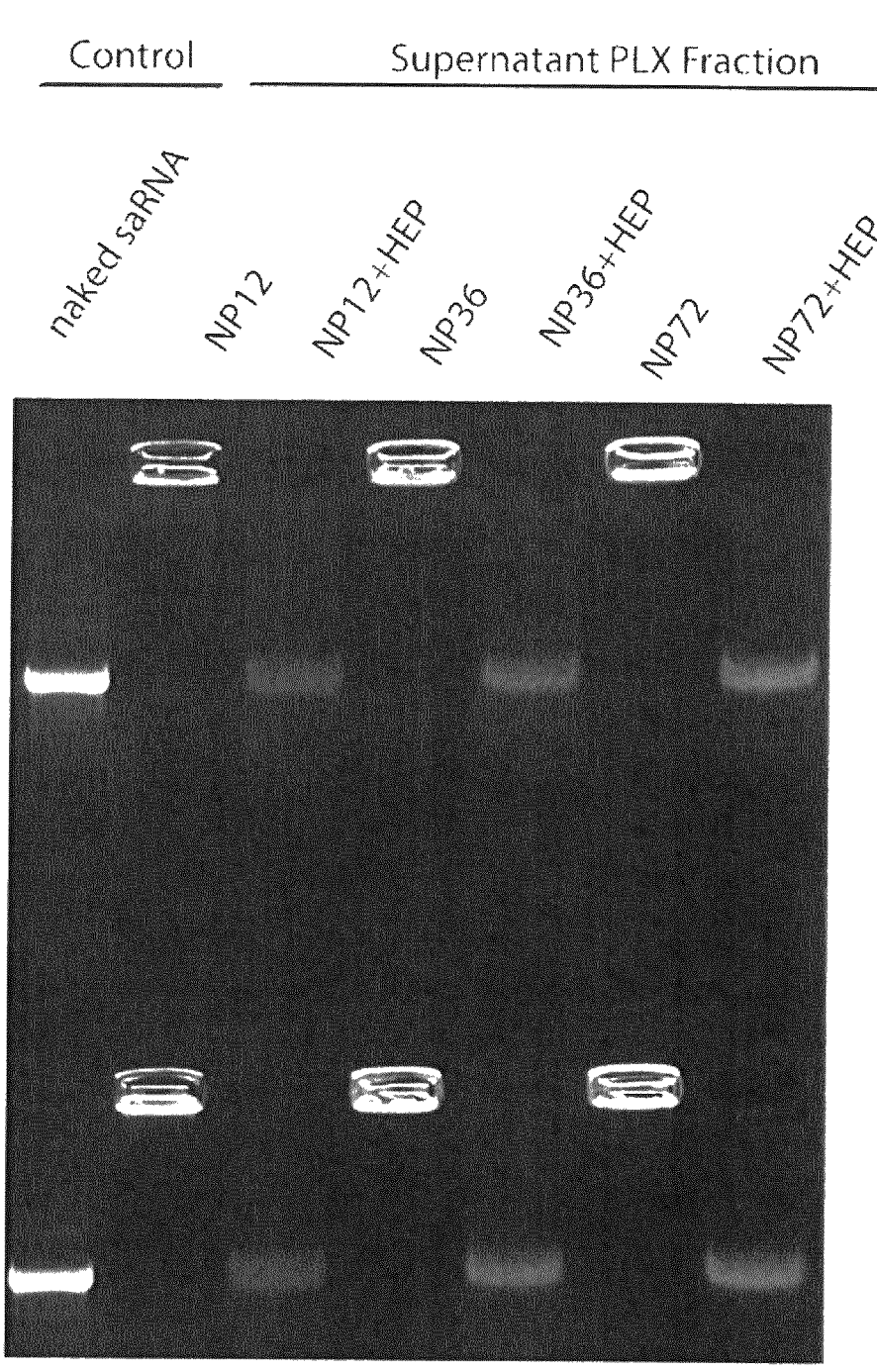

FIG. 5: Free mRNA and saRNA in PEI Polyplex-Populations after centrifugation iVT mRNA or saRNA was complexed in different N/P ratios between 9-36 in MBG buffer (final concentration 5% w/v Glucose, 10 mM MES, pH 6.1). Formulation was fractionated by centrifugation (20.000 G, 4° C., 90') to purify RNA in supernatant. N/P ratio is calculated based on the PEI:RNA charges ratio. RNA concentration in each fraction is determined by UV-absorption measurement in the 260 nm wavelength, but also taking into account purity ratios 260/230 and 260/280 nm. FIG. 5 shows a agarose gel electrophoresis of the supernatant fraction at different N/P ratios (12, 36, 72), wherein high-concentrated heparin (HEP, 100 mg/ml) was used to release the RNA in the supernatant phase after incubation at 30° C. for 20 min. Upper agarose gel lanes and lower lanes are technical replicates containing the same formulation.

Figure 6:
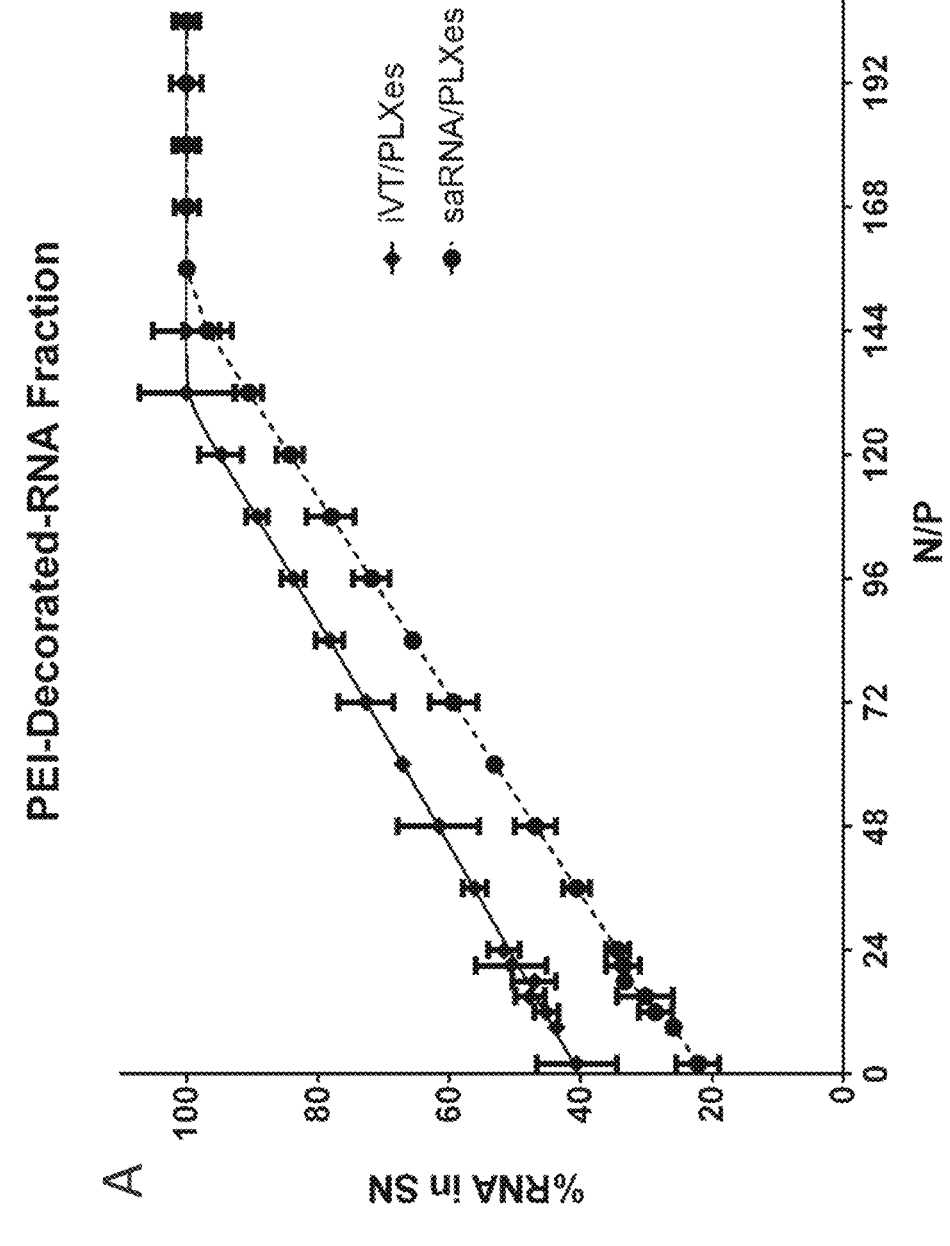

FIG. 6: Characterization of very high N/P Ratios mRNA and saRNA/PEI Polyplex-Populations by centrifugation iVT mRNA or saRNA was complexed in different N/P ratios between 9-204 in MBG buffer (final concentration 5% w/v Glucose, 10 mM MES, pH 6.1). Formulation was fractionated by centrifugation (20.000 G, 4° C., 90') to purify RNA in supernatant. N/P ratio is calculated based on the PEI:RNA charges ratio. RNA concentration in supernatant fraction is determined by UV-absorption measurement in the 260 nm wavelength, but also taking into account purity ratios 260/230 and 260/280 nm. FIG. 6 indicates the RNA % in the supernatant in relation to the total used RNA, found in the different fractions of iVT mRNA/PEI or saRNA/PEI-polyplexes formulations in 3 independent experiments (n=3) with two technical duplicates for UV measurements (x=2)

FIG. 7: Characterization of saRNA/PEI Polyplex-Populations separated by Ultracentrifugation saRNA or iVT mRNA was complexed at N/P ratios between 12-120 ratio in MBG buffer (final concentration 5% w/v Glucose, 10 mM MES, pH 6.1). N/P ratio is calculated based on the PEI-RNA charges ratio. Ultracentrifugation analysis was carried out in a Optima XL-A/XL-I (Beckman-Coultier) at 80.000 G, RT. RNA sedimentation coefficient is determined by absorption in the 255 nm wavelength, Cy5-PEI sedimentation is measured by specific absorption in the 650 nm wavelength. FIG. 7A indicates the intensity of absorption in two different wavelengths at different sedimentation coefficients (S) of saRNA complexed at N/P ratio of 12 with labeled PEI with Cy5 fluorophore. Left Y-axis in FIG. 7A represents RNA absorption at 255 nm wavelength (black continuous curve), while right Y-axis represents PEI absorption at 650 nm wavelength (black dash curve). FIG. 7B indicates the extrapolated percentages of co-sedimenting PEI and RNA in each sedimentation coefficient group over the total amount of sedimenting RNA and PEI in FIG. 7A. FIG. 7C indicates the abundance or the absorption at λ=255 nm of complexed iVT mRNA in relation to the sedimentation coefficients (S) at different N/P ratios (12-120).

Figure 8:
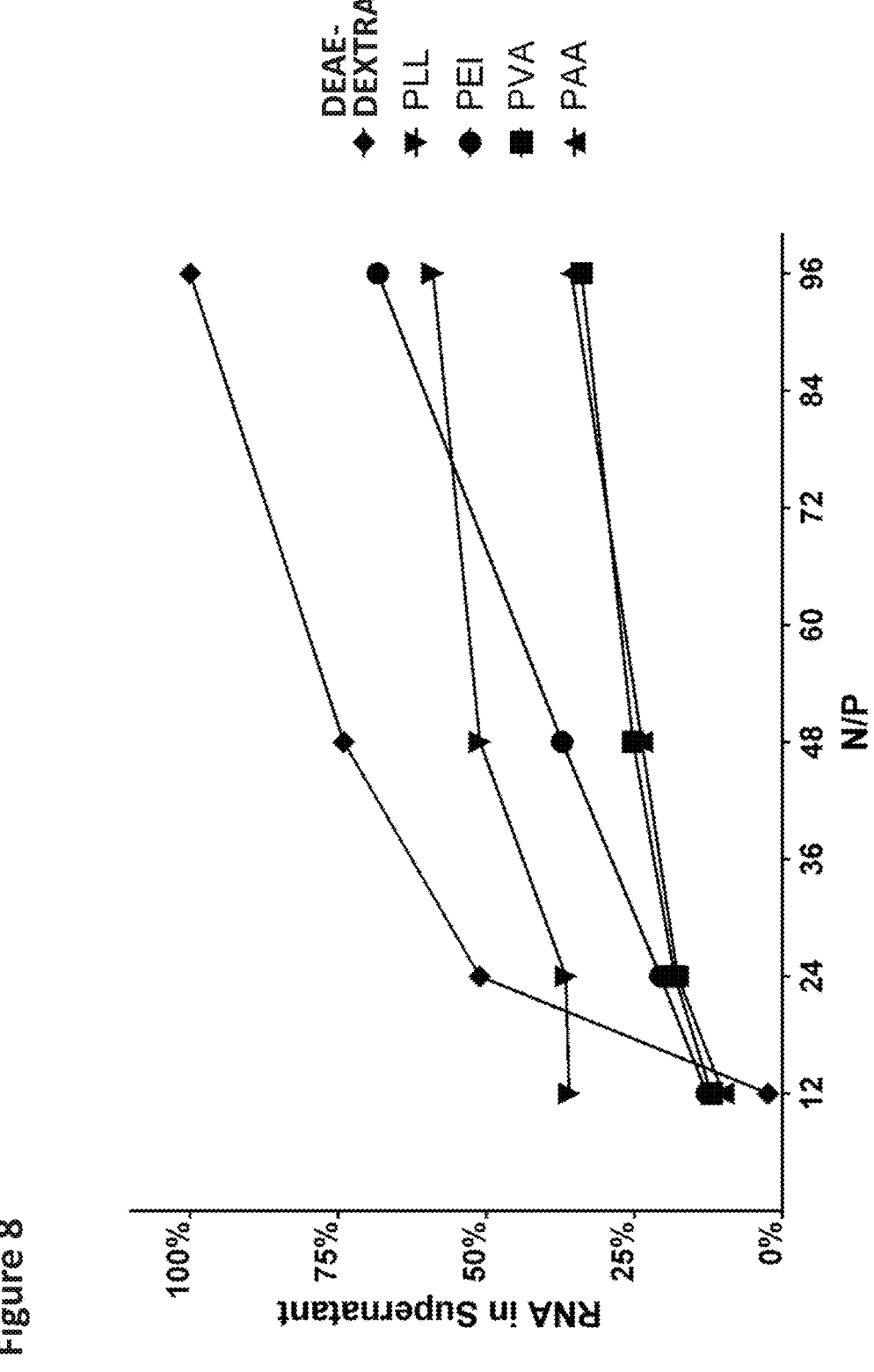

FIG. 8: Characterization of different cationic polymers derived sa A/Polyplexes-Populations separated by centrifugation The saRNA was complexed at different N/P ratios between 12-96 in MBG buffer (final concentration 5% w/v Glucose, 10 mM MES, pH 6.1). Formulation was fractionated by centrifugation (20.000 G, 4° C., 90') to purify particles in supernatant. N/P ratio is calculated based on the in cationic polymer:RNA charges ratio. Five different cationic polymers where tested (PEI=inVivo/Jet-PEI 22 kDA, DEAE-Dextran 20 kDa, PVA=polyvinylamine 25 kDa, PAA=polyallylamine 17.5 kDa, PLL=poly-1-lysine 32.5 kDa). RNA concentration in supernatant fraction is determined by UV-absorption measurement in the 260 nm wavelength, but also taking into account purity ratios 260/230 and 260/280 nm. FIG. 8 indicates RNA % in the supernatant over the total found in the different fractions of saRNA/Polyplexes formulations in 2 independent experiments (n=2) with two technical duplicates for UV measurements (x=2)

FIG. 9: Luminescence read-out after 24 hrs of transfection in C2C12 cells with fractionated formulation of polyplexes containing iVT mRNA or saRNA Secreted nano-luciferase encoding iVT mRNA or saRNA was complexed at different NP ratios between 2-36 in MBG buffer (final concentration 5% w/v Glucose, 10 mM MES, pH 6.1). Formulation was fractionated with centrifugation assay (20.000 G, 4° C., 90') to obtain RNA in supernatant. Formulations are characterized prior to transfection to confirm RNA concentration in the formulation, % of RNA in supernatant after centrifugation and size. Secreted Luciferase is measured according to manufacturer protocol (Nano-GLO, Promega, USA) after 24 of transfection of 5 ng of RNA/well in triplicates per N/P condition. N/P ratio is calculated based on the RNA charges ratio. FIG. 9A indicates transfection of PEI/iVT mRNA polyplexes at 5 ng of RNA/well in 3 independent experiments (n=3) with technical triplicates. FIG. 9B indicates transfection PEI/saRNA polyplexes at 5 ng of RNA/well in 3 independent experiments (n=3) with technical triplicates.

Figure 10:
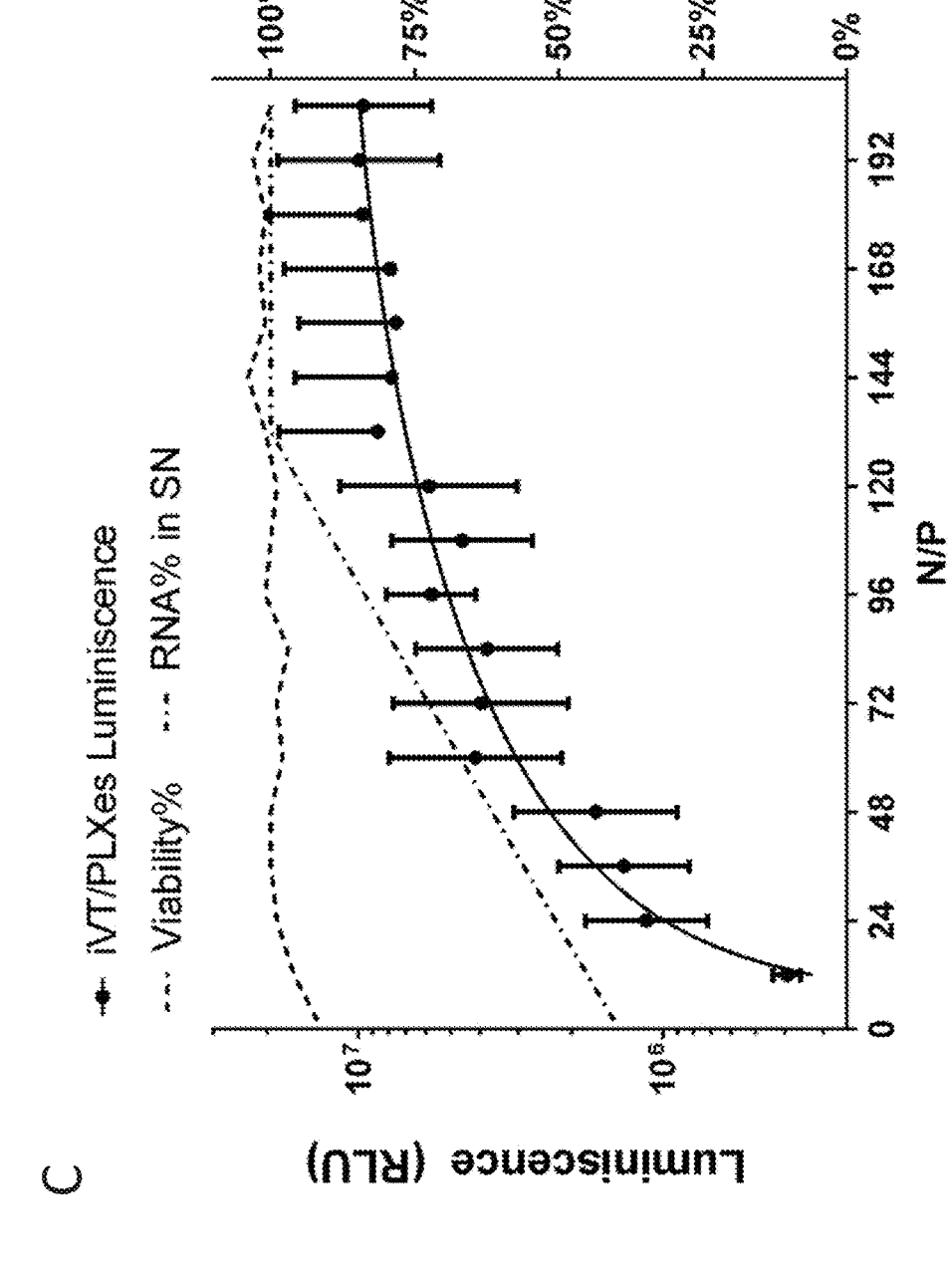

FIG. 10: Luminescence read-out after 24 hrs of transfection in C2C12 with of very high N/P Ratios iVT mRNA and saRNA/PEI Polyplex Secreted nano-luciferase encoding iVT or saRNA was complexed at different NP ratios between 2 to 204 in MBG buffer (final concentration 5% w/v Glucose, 10 mM MES, pH 6.1). Formulations are characterized prior to transfection to confirm RNA concentration in the formulation, % of RNA in Supernatant after centrifugation and size. Secreted Luciferase is measured according to manufacturer protocol (Nano-GLO, Promega, USA) after 24 hrs of transfection in triplicates per N/P condition. Cell viability after 24 hrs of transfection in triplicates per N/P condition was measured according to Cell-Titer-Glo manufacturer protocol. FIG. 10A indicates viability and transfection efficacy correlation of PEI/saRNA polyplexes at 50 ng of RNA/well in 1 independent experiments (n=1) with technical triplicates. FIG. 10B Left Y-axis indicates transfection efficacy correlation of PEI/saRNA polyplexes at 5 ng of RNA/well in 3 independent experiments (n=3) with technical triplicates (black continuous curve), Right Y-axis indicates percentage of viability after transfection (black dash curve) and percentage of RNA found in supernatant in each tested N/P ratio (black dash-dot-dash curve). FIG. 10C Left Y-axis indicates transfection efficacy correlation of PEI/iVT mRNA polyplexes at 5 ng of RNA/well in 3 independent experiments (n=3) with 3 technical triplicates (x=3) (black continuous curve), viability of transfected cells and % of RNA in the formulation in 3 independent experiments (n=3) with 3 technical triplicates (x=3), right Y-axis indicates percentage of viability after transfection (black dash curve) and percentage of RNA found in supernatant in each tested N/P ratio (black dash-dot-dash curve).

FIG. 11: In vivo read-out of luminescence

Five groups (3 Balb/c mice per group) received intramuscular (i.m.) application in the ventral side of each leg of 62.5 ng of formulated saRNA encoding Luciferase. The animals were subjected to non-invasive in vivo bioluminescence imaging over 15 days at different time points (d1, d3, d6, d9, d15). Photons deriving from Luciferase protein were collected over one minute and are shown as graphical quantification of measured photons/second (p/s) at injection site. Each group received the same amount of formulated saRNA with different amounts of PEI resulting in the N/P ratios 12, 24, 48, 72 and, 96. saRNA was complexed at desired N/P ratios in MBG buffer (final concentration 5% w/v Glucose, 10 mM MES, pH 6.1). NP ratio is calculated based on the PEI-RNA charges ratio. FIG. 11A indicates quantified bioluminescence per injected N/P ratio of formulated saRNA, six days after the injection. FIG. 11B indicates quantified bioluminescence per injected N/P ratio of formulated saRNA over the fifteen days of measurements, represented as area under the curve for each injected N/P group.

FIG. 12: In vivo read-out of luminescence and CD8 response to luciferase peptides Three groups (3 Balb/c mice per group) received intramuscular (i.m.) application in the ventral side of each leg of formulated saRNA encoding Luciferase. The animals were subjected to non-invasive in vivo bioluminescence imaging over 15 days at different time points (d1, d3, d6, d9, d15). Photons deriving from Luciferase protein were collected over one minute and are shown as graphical quantification of measured photons/second (p/s) at injection site. Each group received the same amount of PEI-Polymer but different amounts of formulated saRNA with PEI but with different N/P ratios (N/P12, 500 ng; N/P24, 250 ng; N/P48, 125 ng). saRNA was complexed at desired N/P ratios in MBG buffer (final concentration 5% w/v Glucose, 10 mM MES, pH 6.1). NP ratio is calculated based on the PEI-RNA charges ratio. FIG. 12A indicates quantified bioluminescence per injected N/P ratio of formulated saRNA over the whole experiment. FIG. 12B indicates quantified response 15 days after i.m. application of CD8 positive T cells from spleen samples of treated mice to luciferase peptides presented by murine MHC via IFN-ELISPOT, normalized to the injected amount of formulated saRNA per N/P group.

FIG. 13: In vivo read-out of Anti-Influenza HA specific IgG after vaccination with saRNA/PEI Polyplex.

Five groups (5 Balb/c mice per group) received intramuscular (i.m.) application in the ventral side of one leg of formulated saRNA encoding Hemagglutinin (HA) of the influenza strain California/7/2009. The animals were subjected to non-invasive serological surveillance over 49 days at different time points (d14, d24, d49). Anti-Influenza HA antibodies in serum were quantified by enzyme-linked immunosorbent assay. Each group received the same amount of PEI-Polymer but different proportional amounts of formulated saRNA to achieve the N/P ratio increment (N/P12, 500 ng; N/P48, 125 ng; N/P72, 83.3 ng; N/P96, 62.5 ng, N/P120, 50 ng). saRNA was complexed at desired N/P ratios in MBG buffer (final concentration 5% w/v Glucose, 10 mM MES, pH 6.1). NP ratio is calculated based on the PEI-RNA charges ratio. FIG. 13A indicates quantified absolute titer values of Anti-Influenza HA IgG found in serum per injected sample of formulated saRNA at the indicated N/P ratio over the whole experiment. FIG. 13B indicates quantified titer values of Anti-Influenza HA IgG found over the whole experiment in serum per injected N/P ratio and normalized to RNA dose of formulated saRNA in each group.

Figure 14:
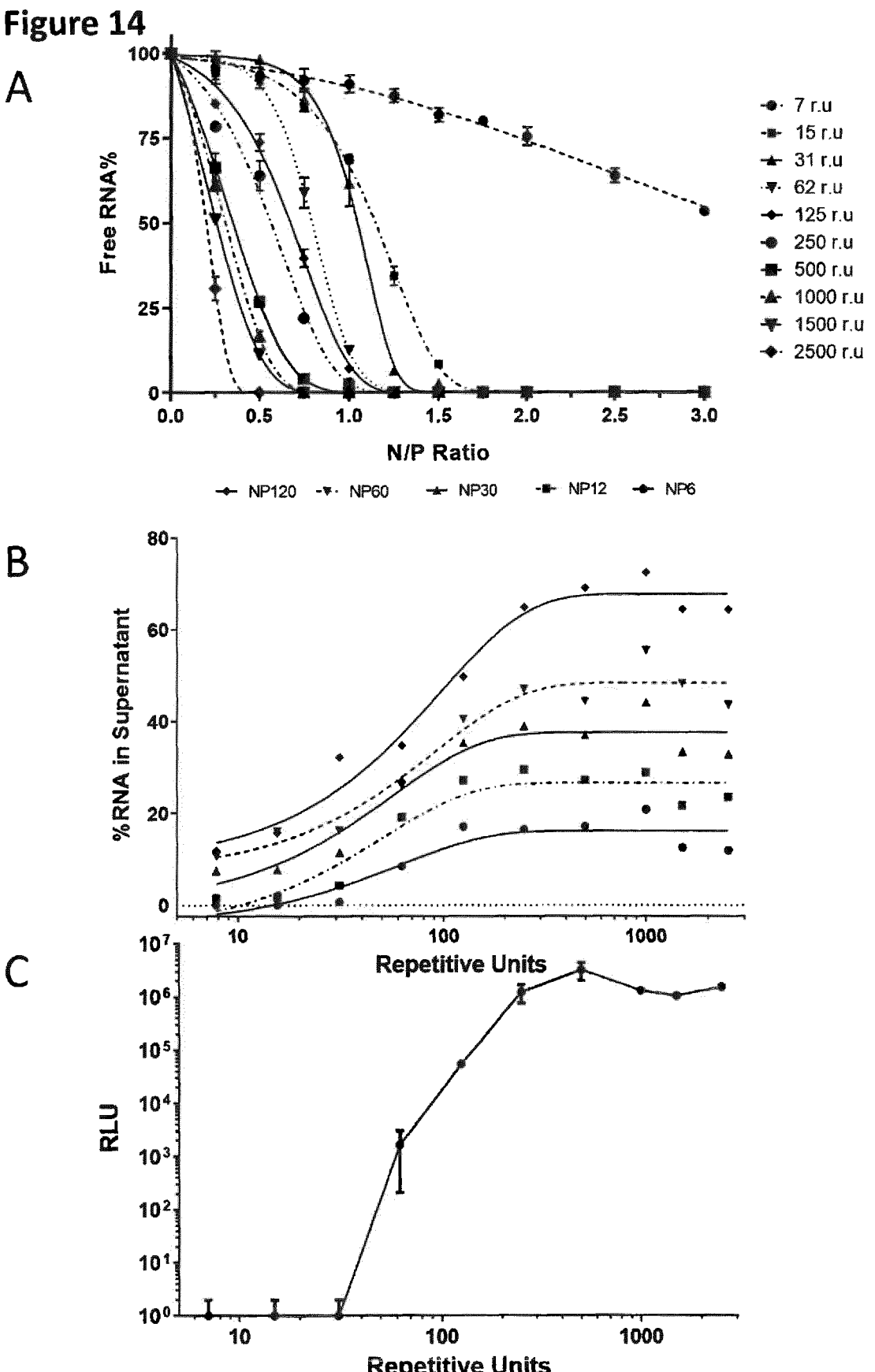

FIG. 14: Characterization of cationic polymer length impact in RNA/PEI Polyplex-Populations.

PEI-polymers of ten different lengths with increasing amount of ethyleneimine repetitive units (r.u) were used for complexing secreted nano-luciferase encoding saRNA at different NP ratios between 0-192 in MBG buffer (final concentration 5% w/v Glucose, 10 mM MES, pH 6.1). The polymer lengths tested are defined by their number of repetitive units of ethylenimine: 7 r.u (0.34 kDa), 15 r.u (0.68 kDa), 31 r.u (1.4 kDa), 62 r.u (2.79 kDa), 125 r.u (5.63 kDa), 250 r.u (11.25 kDa), 500 r.u (22.5 kDa), 1000 r.u (45 kDa), 1500 r.u (67.5 kDa), 2500 r.u (112.5 kDa). The fraction of free RNA was analysed for all formulations by standard agarose gel electrophoresis. Formulation was fractionated with centrifugation assay (20.000 G, 4° C., 90') to obtain RNA in supernatant. Formulations were characterized prior to transfection to confirm RNA concentration in the formulation, % of RNA in supernatant after centrifugation and hydrodynamic diameter (z-average). The expression of secreted luciferase is measured In-Vitro according to manufacturer protocol (Nano-GLO, Promega, USA) after 24 h of transfection of 10 ng with RNA/well in triplicates per N/P condition and Polymer Length. N/P ratio is calculated based on the PEI-RNA charges ratio. FIG. 14A indicates the free RNA content of PEI/iVT mRNA polyplex formulations at 5 ng of RNA/well dependent on N/P ratio and PEI length in 3 independent experiments (n=2) with technical triplicates. FIG. 14B indicates RNA % in the supernatant in reference to the total RNA in the different fractions of the formulations at different N/Ps and PEI-polymer lengths in 2 independent experiments (n=2) with two technical duplicates for UV measurements (x=2) FIG. 14C indicates luciferase activity after transfection with PEI/saRNA polyplexes at N/P120 for all tested PEI-polymer lengths (repetitive units) in 2 independent experiments (n=2) with technical triplicates. FIG. 14D shows the structure formula of an ethyleneimine subunit and a table indicating the tested polymer lengths defined by their number of repetitive units of ethyleneimine, the corresponding molecular weight (Da), and the obtained polymer polydispersity after synthesis.

FIG. 15: In vivo read-out of luminescence and CD8 mediated immune response to luciferase peptides as a function of polymer length Seven groups (3 Balb/c mice per group) received intramuscular (i.m.) administration of formulated saRNA encoding Luciferase in the ventral side of each leg. Formulation buffer was injected into one extra group (3 Balb/c mice) as a control. The animals were subjected to non-invasive in vivo bioluminescence imaging over 20 days at different time points (d1, d3, d6, d9, d20). Photons deriving from Luciferase protein were collected over one minute and are shown as graphical quantification of measured photons/second (p/s) at injection site. Each group received the same amount (125 ng) of formulated saRNA with PEI, formulated at the same N/P ratio (N/P 120) but using different PEI-polymer lengths (31 r.u, 62 r.u, 125 r.u, 250 r.u, 500 r.u, 1000 r.u, 2500 r.u). saRNA was complexed at desired N/P ratio in MBG buffer (final concentration 5% w/v Glucose, 10 mM MES, pH 6.1). The polymer lengths that had been tested have the indicated number of repetitive units of ethylenimine and molecular weight: 31 r.u (1.4 kDa), 62 r.u (2.79 kDa), 125 r.u (5.63 kDa), 250 r.u (11.25 kDa), 500 r.u (22.5 kDa), 1000 r.u (45 kDa), 2500 r.u (112.5 kDa). NP ratio is calculated based on the PEI-RNA charges ratio. Formulations were characterized prior to injection to confirm RNA concentration in the formulation, % of RNA in Supernatant and size. FIG. 15A indicates quantified bioluminescence per injected Polymer-length at N/P120, 125 ng of formulated saRNA, over the whole experiment. FIG. 15B indicates on the left Y-axis the measured bioluminescence at day 6 after injection, as a function of the polymer-length (repetitive units). The right Y-axis shows the % of RNA found in the supernatant of the injected formulations. FIG. 15C indicates quantified response of CD8 positive T cells from spleen samples of treated mice 20 days after i.m. application. The CD8 response to luciferase peptides presented by murine MHC is quantified via IFN release in an ELISPOT. An irrelevant peptide serves as control to show that the CD8 answer to the luciferase peptide is specific.

Figure 16:
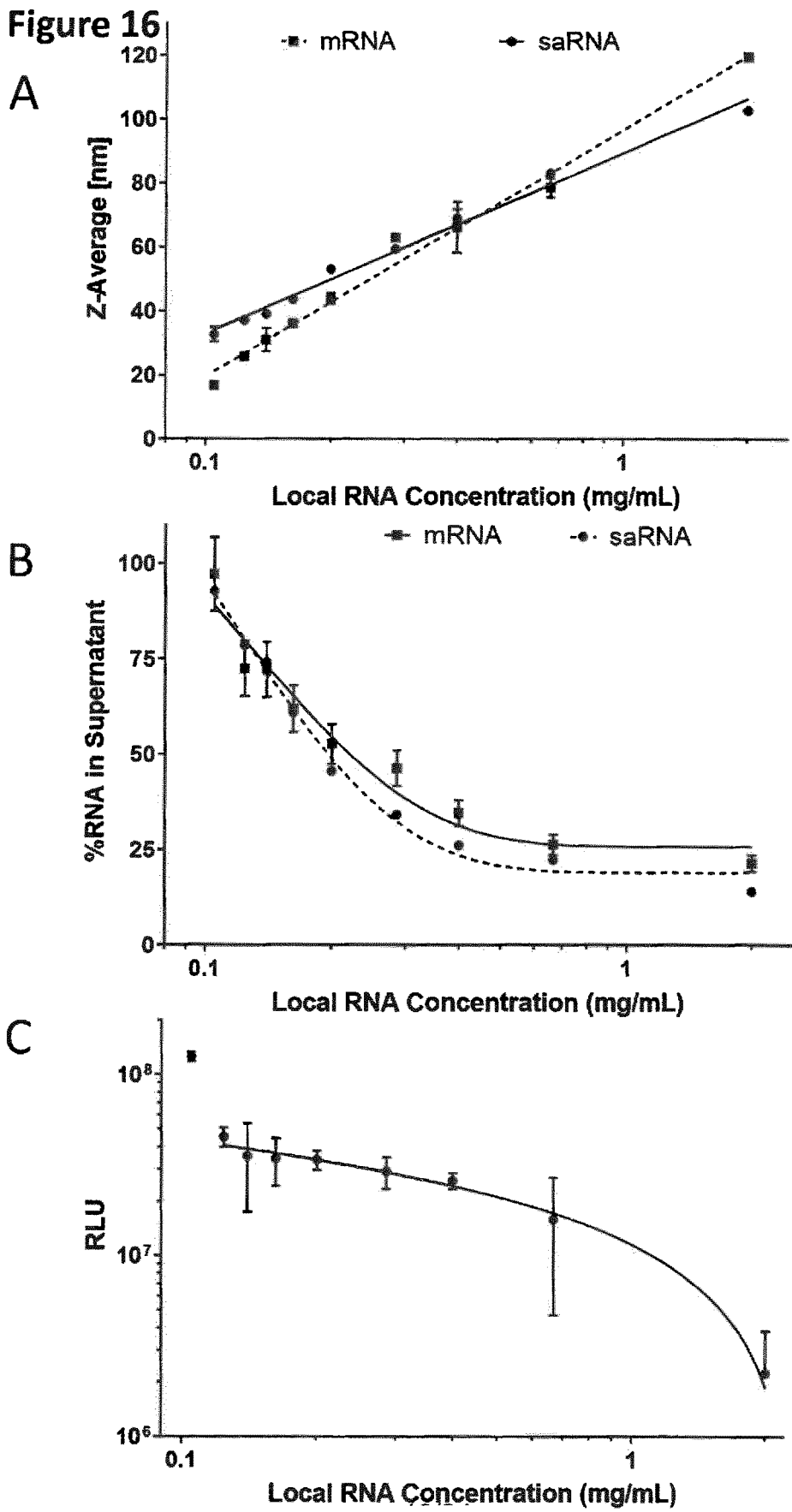

FIG. 16: Effect of local concentration of RNA on the populations of RNA/PLXes during formulation.

Nine formulations containing mRNA or saRNA encoding secreted nano-luciferase were complexed at N/P 12 with 500 r.u PEI (22.5 kDa) in MBG Buffer (final concentration 5% w/v Glucose, 10 mM MES, pH 6.1). Final concentration of RNA (0.1 mg/ml) and final formulation volume (500 μL) was kept constant between the different formulations, but the mixing ratio of the RNA containing solution and the PEI-polymer containing solution where varied in order to have different starting concentrations of RNA in the RNA containing solution. The tested starting RNA concentrations (local concentration) varied between 2.0 mg/ml and 0.105 mg/ml. Formulation was fractionated with centrifugation assay (20.000 G, 4° C., 90') to obtain RNA in supernatant. RNA concentration in the formulation and size of the complexes was measured before fractionation and after purification of RNA in supernatant. Secreted Luciferase In-Vitro expression was measured according to manufacturer protocol (Nano-GLO, Promega, USA) 24 hours after transfection with 12.5 ng of RNA/well in triplicates per formulation. N/P ratio is calculated based on the PEI-RNA charges ratio. FIG. 16A indicates hydrodynamic diameter of complexes formulated at different local concentrations of RNA, but with constant final RNA concentration (0.1 mg/ml) and N/P ratio (12). Data here represents 2 independent experiments (n=2) with technical duplicates. FIG. 16B indicates RNA % in the supernatant over the total found in the different fractions of RNA/Polyplexes formulations at different local concentrations of RNA, but with constant final RNA concentration (0.1 mg/ml) and N/P ratio (12). Data here represents 2 independent experiments (n=2) with two technical duplicates for UV measurements (x=2) FIG. 16C indicates expression of secreted luciferase after transfection PEI/saRNA formulations at different local concentrations of RNA, but with constant final RNA concentration (0.1 mg/ml) and N/P ratio (12). Formulations were in 2 independent experiments (n=2) with technical triplicates (x=3).

Figure 17:
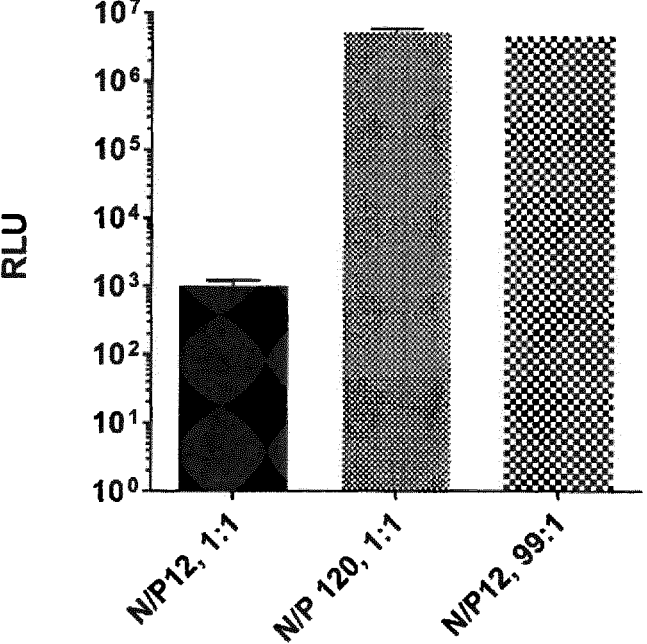

FIG. 17: Effect of local concentration of A on the populations of A/PLXes during formulation.

Three formulations containing secreted nano-luciferase encoding saRNA were complexed at either N/P 12 or N/P120 with 500 r.u PEI (22.5 kDa) in MBG Buffer (final concentration 5% w/v Glucose, 10 mM MES, pH 6.1). Final concentration of RNA (0.1 mg/ml) and final formulation volume (500 µL) was kept constant between the different formulations, but the mixing ratio of the RNA containing solution and the PEI-polymer containing solution were varied in order to have different starting concentrations of RNA in the RNA containing solution. One formulation was formulated at N/P12 and local RNA concentration of 0.2 mg/ml (1:1). One formulation was formulated at N/P120 and local RNA concentration of 0.2 mg/ml (1:1). One formulation was formulated at N/P12 and local RNA concentration of 0.105 mg/ml (99:1). Secreted Luciferase In-Vitro expression was measured according to manufacturer protocol (Nano-GLO, Promega, USA) 24 hours after transfection with 12.5 ng of RNA/well in triplicates per formulation. N/P ratio is calculated based on the PEI-RNA charges ratio. FIG. 17 indicates expression of secreted luciferase after transfection with PEI/saRNA formulations at different local concentrations of RNA and/or NIP, but with constant final RNA concentration (0.1 mg/ml) and formulation volume (500 µL). Formulations were tested in 2 independent experiments (n=2) with technical triplicates (x=3).

Figure 18:
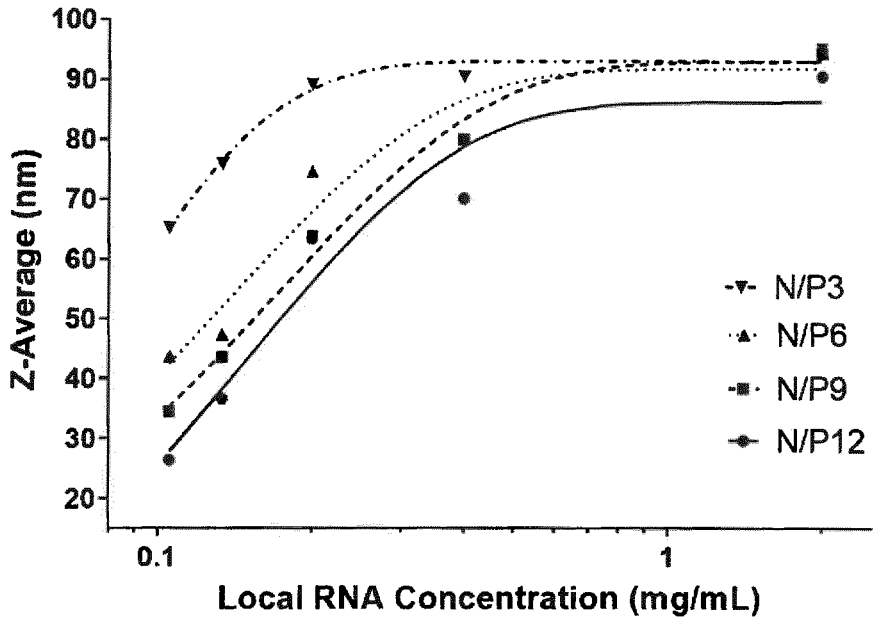

FIG. 18: Impact of the local concentration of A and N/P Ratio on the populations of RNA/PLXes during formulation.

Twenty five formulations containing secreted nano-luciferase encoding saRNA were complexed at different N/Ps (3, 6, 9 and 12) and different mixing ratios of the RNA containing solution and the PEI-polymer containing solution, in order to have five different starting concentrations of RNA (local concentration) per tested N/P ratio. For all formulations, final concentration of RNA (0.1 mg/ml) and final formulation volume (500 µL) were kept constant. All formulations were performed with 500 r.u PEI (22.5 kDa) in MBG Buffer (final concentration 5% w/v Glucose, 10 mM MES, pH 6.1). FIG. 18 indicates hydrodynamic diameter of complexes in the tested formulations at different N/P ratios and local concentrations of PEI/saRNA formulations. Data here represents 2 independent experiments (n=2) with technical duplicates (x=2).

Figure 19:
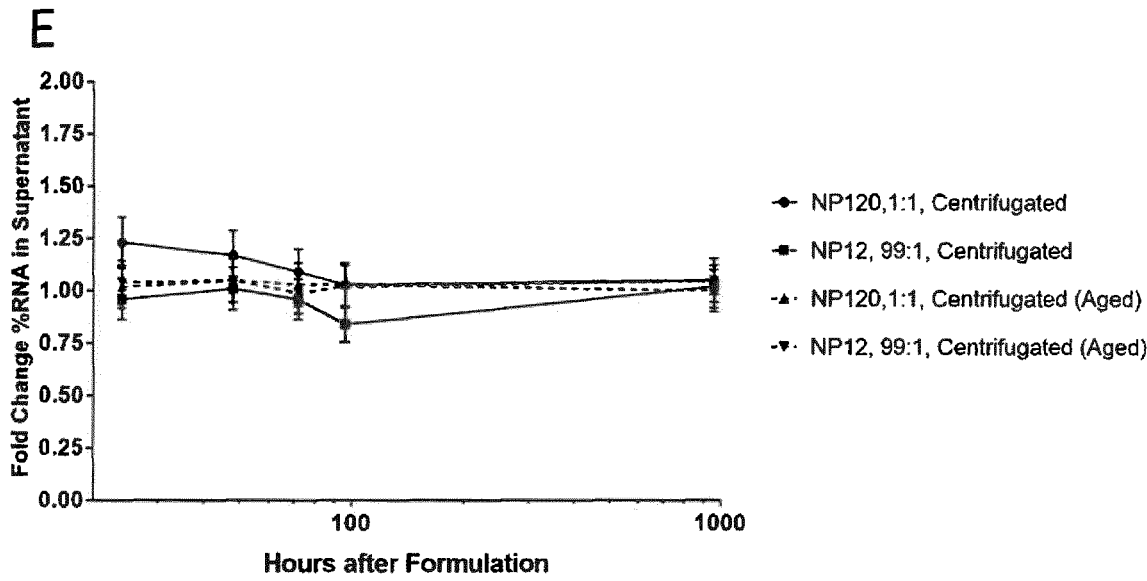

FIG. 19: Colloidal stability of RNA/PLXes populations after formulation.

Two formulations containing secreted nano-luciferase encoding saRNA were complexed at either N/P 12 or N/P120 with 500 r.u. PEI (22.5 kDa) in MBG Buffer (final concentration 5% w/v Glucose, 10 mM MES, pH 6.1). Final concentration of RNA (0.1 mg/ml) and final formulation volume (500 µL) was kept constant between the different formulations but the mixing ratio of the RNA containing solution and the PEI-polymer containing solution were varied in order to have different starting concentrations of RNA in the RNA containing solution (local concentration). One formulation was formulated at N/P12 and local RNA concentration of 0.105 mg/ml (99:1). One formulation was formulated at N/P120 and local RNA concentration of 0.2 mg/ml (1:1). Both formulations were stored at 4° C. for over 960 hours (40 days) and at different time points (0, 24, 48, 72, 96, 960 hours) physicochemical properties of the formulation such as hydrodynamic diameter, complex concentration in counts/s or % of RNA content in Supernatant over the total concentration, were monitored. Prior storage of the formulation, a fraction of the total was centrifugated and purified. RNA in supernatant was also stored over the 960 hours at 4° C. for monitoring of the previously mentioned physicochemical properties. At each specific time point the physicochemical parameters of the stock formulation, the stored (aged) supernatant fraction and freshly prepared supernatant fraction of RNA are collected. FIG. 19A indicates hydrodynamic diameter over time of complexes in formulation prior to centrifugation and from freshly prepared supernatant fractions at each time point, so that hydrodynamic diameter of RNA in supernatant can be determined. FIG. 19B indicates the amount of complexes in formulation prior to centrifugation and from freshly prepared supernatant fractions at each time point. FIG. 19C indicates hydrodynamic diameter over time of complexes in formulation from freshly prepared supernatant fractions at each time point and from aged supernatant fraction that was centrifuged at t=0 (0 hour), so that hydrodynamic diameter of RNA in supernatant can be determined between freshly prepared and aged formulation. FIG. 19D indicates the amount of complexes in formulation from freshly prepared supernatant fractions at each time point and from aged supernatant fraction that was centrifuged at t=0 (0 hour). FIG. 19E indicates changes in the fraction of RNA identified in supernatant over time from both freshly centrifugated supernatant and aged supernatant that was centrifuged at t=0 (0 hour).

FIG. 20: Characterization of G5-PLL(64) cationic dendrimer in the formation of RNA/Polyplexes-Populations A novel biodegradable cationic polymer of the poly (amidoamine)s family, which consists of a G(5)-PAMAM dendrimer functionalized with 64 arms of penta-L-Lysine polymers, was evaluated for the complexation of secreted nano-luciferase encoding mRNA or saRNA. Formulations were complexed at different N/P ratios (3-192) in MBG Buffer (final concentration 5% w/v Glucose, 10 mM MES, pH 6.1). Hydrodynamic diameter of the mRNA and saRNA containing formulations at different N/P were evaluated prior centrifugation and transfection with the complexes. RNA concentration was evaluated by UV absorption prior centrifugation. Formulations were fractionated with centrifugation assay (20.000 G, 4° C., 90') to obtain RNA in supernatant. RNA concentration in supernatant was evaluated and determined as % of RNA found in supernatant over the total RNA. Secreted Luciferase In-Vitro expression is measured according to manufacturer protocol (Nano-GLO, Promega, USA) 24 hours after transfection with 12.5 ng of RNA/well in triplicates. N/P ratio is calculated based on the G(5)PLL(64)-RNA charges ratio. FIG. 20A indicates hydrodynamic diameter of complexes prior to centrifugation, i.e. from the whole formulation. FIG. 20B indicates RNA % in the supernatant over the total found in the different fractions of RNA/G(5)-PLL(64) formulations at different N/P ratios. FIG. 20C indicates expression of secreted luciferase after transfection with G(5)-PLL(64)/RNA formulations at different N/P ratios. Formulations were tested in 3 independent experiments (n=3) with technical triplicates (x=3).

Figure 21:
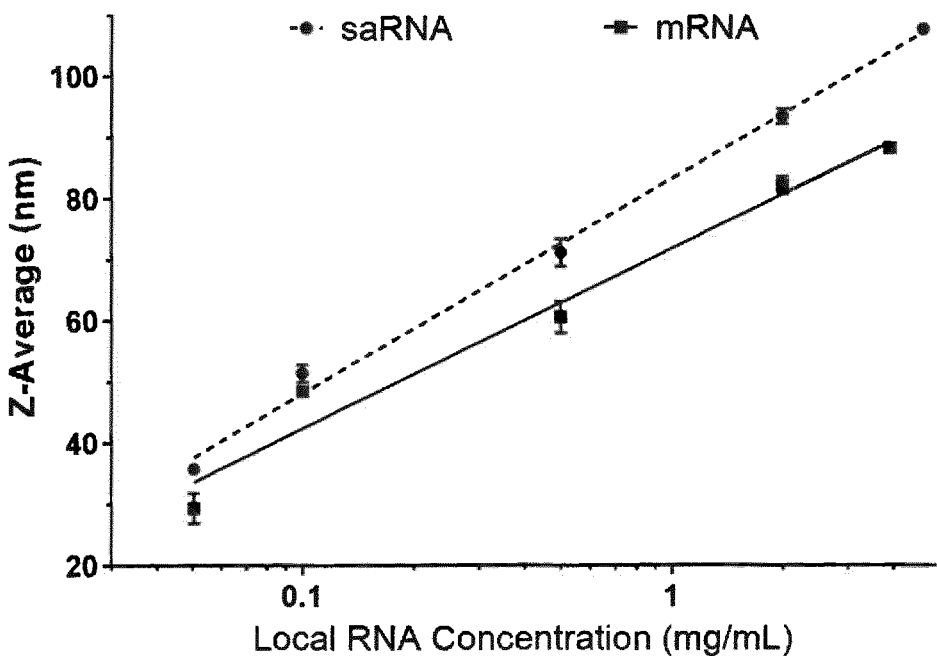

FIG. 21: Effect of local concentration of A on G(5)-PLL (64)/RNA complexes during formulation.

Five formulations containing Secreted nano-luciferase encoding mRNA or saRNA were complexed at N/P 12 with G(5)-PLL(64) (A novel cationic polymer consisting of a G(5)-PAMAM dendrimer functionalized with 64 arms of penta-L-Lysine polymers) in MBG Buffer (final concentration 5% w/v Glucose, 10 mM MES, pH 6.1). Final concentration of RNA(0.1 mg/ml) and final formulation volume (500 µL) was kept constant between the different formulations, but the mixing ratio of the RNA containing solution and the G(5)-PLL(64) dendrimer containing solution was varied in order to have different starting concentrations of RNA in the RNA containing solution. The tested starting RNA concentrations (local concentration) varied between 4.0 mg/ml and 0.0505 mg/ml. FIG. 21 indicates hydrodynamic diameter of complexes formulated at different local concentrations of RNA, but with constant final RNA concentration (0.05 mg/ml) and N/P ratio (12). Data here represents 2 independent experiments (n=2) with technical duplicates (x=2).

FIG. 22: Characterization of Viromer® in the formation of RNA/Polyplexes-Populations Viromer® is a commercially available branched-PEI heavily modified with alkyl chains and aromatic motifs. Here saRNA/Viromer polyplexes, encoding for secreted nano-luciferase, were formulated at different N/P ratios (0-120) in MBG Buffer (final concentration 5% w/v Glucose, 10 mM MES, pH 6.1). Hydrodynamic diameter of the saRNA containing formulations at different N/P was evaluated prior and after centrifugation. RNA concentration was evaluated by UV absorption prior centrifugation. Formulations were fractionated with centrifugation assay (20.000 G, 4° C., 90') to obtain RNA in supernatant. RNA concentration in supernatant phase was evaluated for quantification of the % of RNA over the total found in supernatant phase. Secreted Luciferase In-Vitro expression was measured according to manufacturer protocol (Nano-GLO, Promega, USA) after 24 of transfection with 12.5 ng of RNA/well in triplicates. Charge ratio was calculated based on the Viromer®/RNA N/P ratio. FIG. 22A indicates hydrodynamic diameter of complexes previous centrifugation, i.e. from the whole formulation (whole-fraction) and after centrifugation, i.e. supernatant fraction (monomeric-fraction). FIG. 22B indicates RNA % in the supernatant over the total found in the different fractions of Viromer®-RNA complexes at different N/P ratios. FIG. 22C indicates expression of secreted luciferase after transfection with Viromer®/RNA formulations at different N/P ratios. Formulations were tested in 3 independent experiments (n=3) with technical triplicates (x=3).

FIG. 23: Effect of concentration of RNA on Viromer®/ RNA complexes during formulation.

Nine formulations containing secreted nano-luciferase encoding saRNA were complexed at N/P 12 with Viromer® (a commercially available branched-PEI heavily modified with alkyl chains and aromatic motivs) in MBG Buffer (final concentration 5% w/v Glucose, 10 mM MES, pH 6.1). Final concentration of RNA (0.05 mg/ml) and final formulation volume (500 µL) was kept constant between the different formulations, but the mixing ratio of the RNA containing solution and the Viromer® containing solution were varied in order to have different starting concentrations of RNA in the RNA containing solution. The tested starting RNA concentrations (local concentration) varied between 4.0 mg/ml and 0.0505 mg/ml. Hydrodynamic diameter of the saRNA containing formulations at different N/P was evaluated prior. RNA concentration was evaluated by UV absorption prior centrifugation. Formulations were fractionated with centrifugation assay (20.000 G, 4° C., 90 min) to obtain RNA in supernatant. RNA concentration in supernatant phase was evaluated for quantification of the % of RNA over the total found in supernatant phase. N/P ratio was calculated based on the Viromer®-RNA charges ratio. FIG. 23A indicates hydrodynamic diameter of complexes formulated at different local concentrations of RNA, but with constant final RNA concentration (0.05 mg/ml) and N/P ratio (12). Data here represents 3 independent experiments (n=3) with technical duplicates (x=2). FIG. 23B indicates RNA % in the supernatant over the total found in the different fractions of Viromer®-RNA complexes at different local concentrations.

Figure 24:
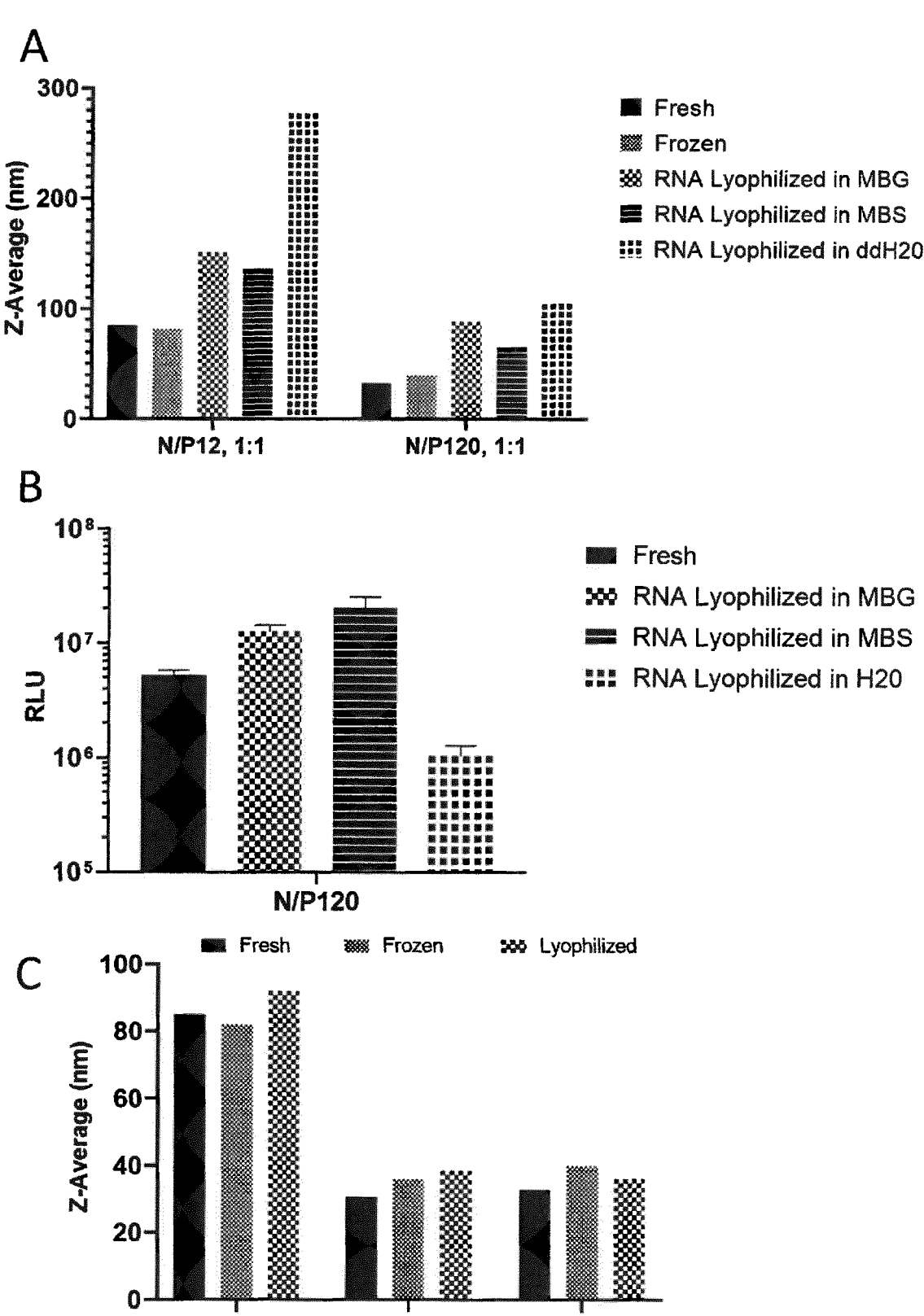
Figure 24:
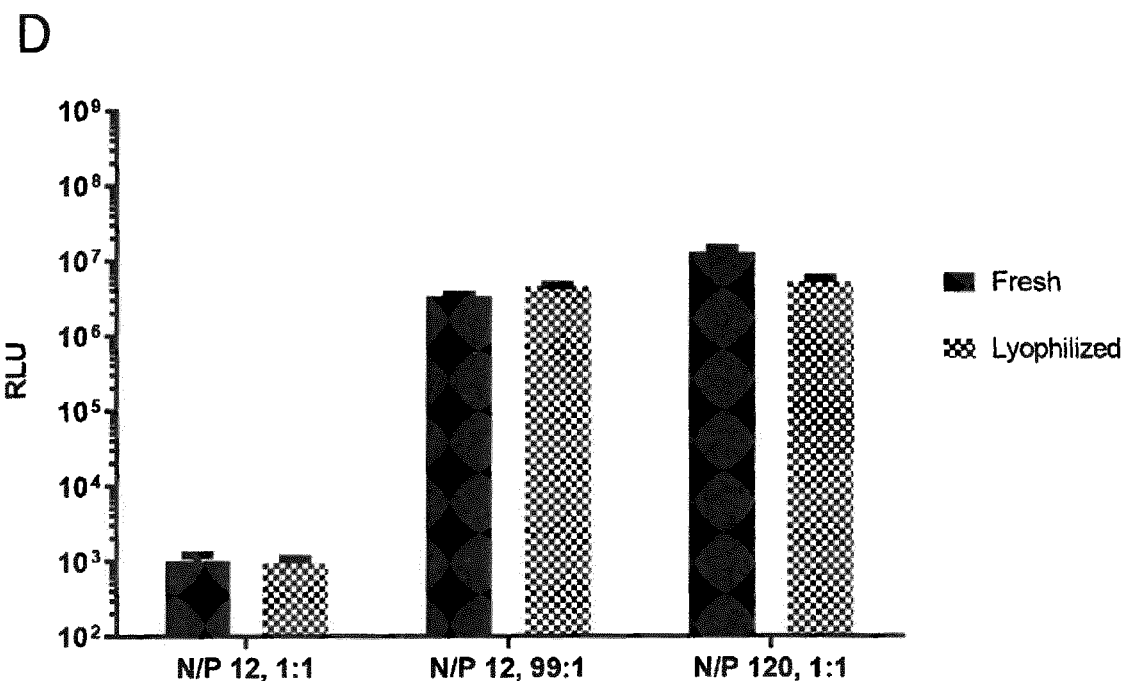

FIG. 24: Lyophilization of A or A/PEI formulations.

A total of three formulations containing secreted nano-luciferase encoding saRNA were complexed at different N/P: either N/P 12 or N/P120 with 500 r.u PEI (22.5 kDa) in MBG Buffer (final concentration 5% w/v Glucose, 10 mM MES, pH 6.1). Final concentration of RNA (0.05 mg/ml) and final formulation volume (500 µL) were kept constant between the different formulations, but the mixing ratio of the RNA containing solution and the PEI-polymer containing solution were varied in order to have different starting concentrations of RNA in the RNA containing solution (local concentration). One lyophilized or frozen sample was formulated using saRNA at N/P12 and local concentration of 0.1 mg/ml (1:1). One lyophilized or frozen sample was formulated using saRNA at N/P12 and local concentration of 0.0505 mg/ml (99:1). One lyophilized or frozen sample was formulated using saRNA at N/P120 and local concentration of 0.1 mg/ml (1:1). Further, saRNA was lyophilized in either MBG Buffer (final concentration 5% w/v Glucose, 10 mM MES, pH 6.1), MBS Buffer (final concentration 10% w/v Sucrose, 10 mM MES, pH 6.1) or ddH20. Lyophilized saRNA was then reconstituted with a PEI-polymer containing solution for a final N/P of either 12 or 120, a final volume of 500 µL and a final RNA concentration of 0.05 mg/ml. Hydrodynamic diameter of the saRNA containing formulations prior and after lyophilisation/freezing at different N/P or local concentration was evaluated. Hydrodynamic diameter was also evaluated for reconstituted lyophilized saRNA samples with PEI-containing solution. Secreted luciferase In-Vitro expression is measured according to manufacturer protocol (Nano-GLO, Promega, USA) 24 hour after transfection with 12.5 ng of RNA/well in triplicates for N/P 120. N/P ratio is calculated based on the PEI-RNA charges ratio. FIG. 24A indicates hydrodynamic diameter of complexes at different N/P Ratio (12 or 120), either from the freshly prepare sample, frozen sample and the reconstituted saRNA, that were previously lyophilized with different buffer systems. FIG. 24B indicates expression of secreted luciferase after transfection with PEI-saRNA formulations at N/P120, one freshly prepared and three saRNA samples that were reconstituted from their lyophilizated form in different buffers. Formulations were tested in 2 independent experiments (n=2) with technical triplicates (x=3). FIG. 24C indicates hydrodynamic diameter of complexes formulated at different local concentrations of RNA and N/P ratio but with constant final RNA concentration (0.05 mg/ml) and final volume (500 μL). Data here represents 3 independent experiments (n=2) with technical duplicates (x=2). FIG. 24D indicates expression of secreted luciferase after transfection with PEI-saRNA formulations formulated at different local concentrations of RNA and N/P ratio, but with constant final RNA concentration (0.05 mg/ml) and final volume (500 μL). Formulations were prepared freshly or after reconstitution of previously lyophilized saRNA/PEI complexes. Data here represents 2 independent experiments (n=2) with technical duplicates (x=2)

FIG. 25: In vivo read-out of Anti-Influenza HA specific IgG and CD4/CD8 T-Cell response after vaccination with lyophilized saRNA or RNA/PEI formulations.

Six groups (5 Balb/c mice per group) received intramuscular (i.m.) application in the ventral side of one leg of 125 ng of formulated saRNA encoding Hemagglutinin (HA) of the influenza strain California/7/2009. One extra group (5 Balb/c mice) received only formulation buffer for comparison. The animals were subjected to non-invasive serological surveillance over 49 days at different time points (d14, d24, d56) and spleen was extracted at the end of experiment for quantification of CD4/CD8 T-Cell response to Influenza HA peptides. Anti-Influenza HA antibodies in serum were quantified by enzyme-linked immunosorbent assay. Virus neutralizing titers were quantified by VNT Assay. CD4/CD8 T-Cell response was quantified by via IFN-ELISPOT of Splenocytes. A total of six formulations containing Influenza-HA encoding saRNA were complexed at different conditions, always with linear PEI (22.5 kDa). Two groups received a freshly formulated saRNA, either at N/P 12 or N/P 120 in MBG Buffer (final concentration 5% w/v Glucose, 10 mM MES, pH 6.1). One group received the reconstitution with water of previously lyophilized saRNA/PEI formulation at N/P120 in MBG Buffer (final concentration 5% w/v Glucose, 10 mM MES, pH 6.1). One group received the reconstitution of previously lyophilized Influenza-HA saRNA in water with a PEI-polymer solution to have a final N/P ratio of 120. One group received the reconstitution of previously lyophilized Influenza-HA saRNA in MBG Buffer (final concentration 5% w/v Glucose, 10 mM MES, pH 6.1) with a PEI-polymer water solution to have a final N/P ratio of 120. One group received the reconstitution of previously lyophilized Influenza-HA saRNA in MBS Buffer (final concentration 10% w/v Sucrose, 10 mM MES, pH 6.1) with a PEI-polymer water solution to have a final N/P ratio of 120. N/P ratio is calculated based on the PEI-RNA charges ratio. FIG. 25A indicates the quantified area under the curve of the absolute titer values of anti-Influenza HA IgG found in serum per injected sample of formulated saRNA over the whole experiment. FIG. 25B indicates quantified virus neutralizing titers of anti-Influenza HA IgG found at d56 of experiment in serum per injected group. FIG. 25C indicates quantified response, 56 days after i.m. application, of CD8 and CD4 positive T cells from spleen samples of treated mice to Influenza (HA) California/7/2009 peptides presented by murine MHC via IFN-ELISPOT.

Figure 26:
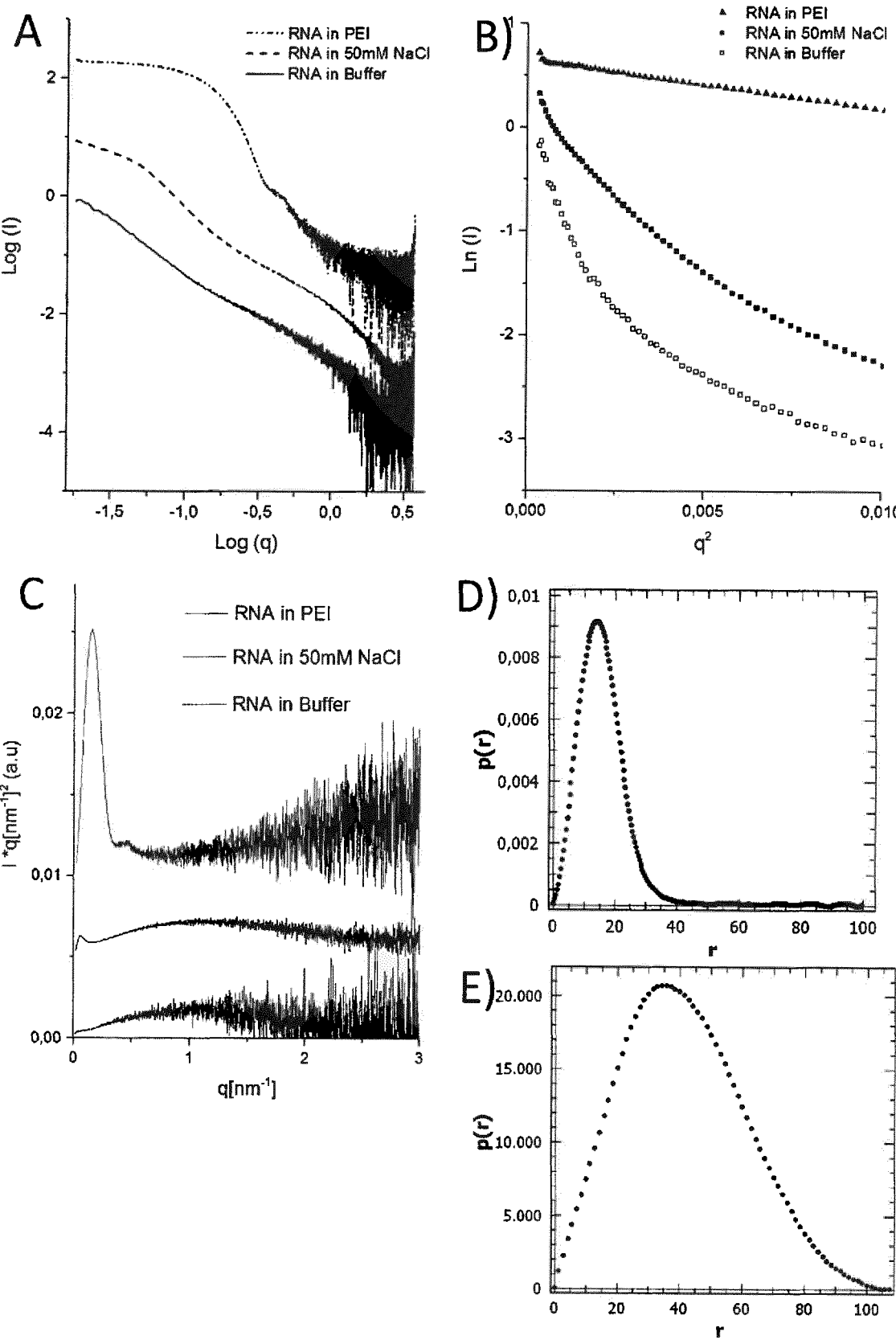

FIG. 26: Evaluation of monomeric RNA-PEI formulation by of small angle X-Ray scattering (SAXS).

Three samples containing secreted nano-luciferase encoding saRNA were prepared for SAXS evaluation. One sample contained saRNA in MBG Buffer (final concentration 5% w/v Glucose, 10 mM MES, pH 6.) at a final concentration of 0.2 mg/ml. One sample contained saRNA in 50 mM NaCl at a final concentration of 1.0 mg/ml. One sample contained saRNA/PEI at N/P12 in MBG Buffer (final concentration 5% w/v Glucose, 10 mM MES, pH 6.) at a final concentration of 0.2 mg/ml. The different concentrations were required in order to obtain sufficient scattering intensity from the RNA in the different media, as determined in previous feasibility experiments. This last sample was prepared at a mixing volume ratio (RNA:PEI Phase) of 99:1 and starting local RNA concentration of 0.105 mg/ml. It was purified with centrifugation assay (20.000 G, 4° C., 90') to obtain exclusively saRNA in supernatant and was reconcentrated with a 10 kDa cut-off Amicon® Ultra Centrifugal Filters in the centrifuge (~3000 G, 4C, 45 min) to reach a final concentration of 0.2 mg/ml. RNA concentration in the formulation and size of the complexes were measured before fractionation and after purification of RNA in supernatant. Data here was obtained during industrial beamtime at the synchrotron in Hamburg, Germany (P12, PETRAIII, EMBL). FIG. 26A scattering data presented as logarithmic intensity (y-axis) vs logarithmic q-space (x-axis). FIG. 26B scattering data presented as Guinier plot, with natural logarithmic intensity (y-axis) vs squared q-space (x-axis). FIG. 26C scattering data presented as Kratky plot, with natural intensity multiplied by squared q-space (y-axis) vs q-space (x-axis). FIG. 26D indicates distance pair distribution function (p(r)) derived from scattering data of saRNA/PEI sample, where p(r) (y-axis) vs radius (x-axis). FIG. 26E indicates distance pair distribution function (p(r)) derived from scattering data of saRNA in 50 mM NaCl sample, where p(r) (y-axis) vs radius (nm) (x-axis).

Figure 27:
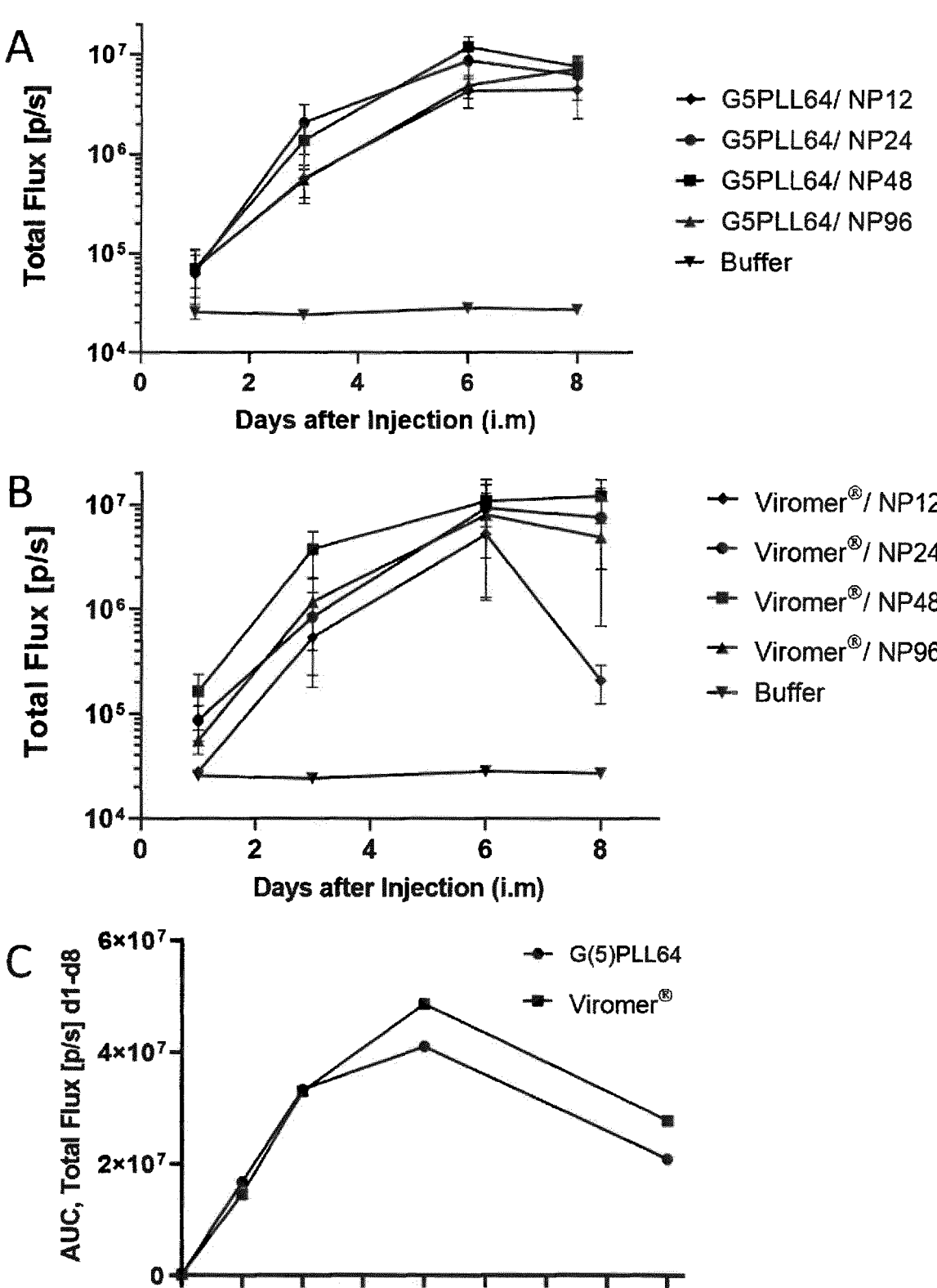

FIG. 27: In-Vivo effect of the increment in the fraction of monomeric-RNA in G(5)-PLL(64)/RNA or Viromer®/RNA formulations.

Eight groups (3 Balb/c mice per group) received intramuscular (i.m.) application in the ventral side of each leg of formulated saRNA encoding Luciferase. One extra group (3 Balb/c mice) was injected with formulation buffer as a control. The animals were subjected to non-invasive in vivo bioluminescence imaging over 8 days at different time points (d1, d3, d6, d8). Photons deriving from Luciferase protein were collected over one minute and are shown as graphical quantification of measured photons/second (p/s) at injection site. Each group received the same amount (125 ng) of formulated saRNA with either G(5)PLL(64) poly (amindoamine) polymer or Viromer®, formulated at different N/P ratio (N/P 12-24-48-96). saRNA was complexed at desired N/P ratio in MBG buffer (final concentration 5% w/v Glucose, 10 mM MES, pH 6.1). NP ratio was calculated based on the Polymer-RNA charges ratio. Formulations were characterized prior to injection to confirm RNA concentration in the formulation, % of RNA in Supernatant and size. FIG. 27A indicates quantified bioluminescence per injected N/P ratio of G(5)PLL(64) at different time points after i.m. application. FIG. 27B indicates quantified bioluminescence per injected N/P ratio of Viromer® at different time points after i.m. application. FIG. 27C indicates quantified bioluminescence per injected N/P ratio of formulated saRNA over the eight days of measurements, represented as area under the curve for each injected N/P group.

FIG. 28: Evaluation of RNA secondary-tertiary structure evaluation in RNA/PEI or RNA/NaCl formulation by Circular Dichroism.

Twelve samples containing secreted nano-luciferase encoding saRNA were prepared for circular dichroism (CD) spectroscopy. The first six RNA/PEI formulations were complexed at different N/P ratio (NT 0-24-48-72-120-240). saRNA was complexed at desired N/P ratio in MBG buffer (final concentration 5% w/v Glucose, 10 mM MES, pH 6.1). NP ratio was calculated based on the Polymer-RNA charges ratio. The second group of six samples of RNA/NaCl formulations were prepared by mixing the RNA containing solution and NaCl containing solution at equivoluminar ratio for a final concentration of 0.1 mg/ml of RNA and different NaCl concentrations (0-2-4-8-16-50 mM). To prepare the RNA containing solution, an appropriate mixture of volumes from the RNA Stock (0.2 m/mL in ddH20) and ddH20 is used. To prepare the NaCl containing solution, an appropriate mixture of volumes from the NaCl Stock (100 mM) and ddH20 is used. FIG. 28A indicates the CD spectrum as function of the measured wavelength(nm) between 235-310 nm with the circular dichroism signal as ellipticity (mdeg) at different NaCl concentrations in the RNA/NaCl formulations. FIG. 28B indicates the CD spectrum as function of the measured wavelength (nm) between 235-310 nm with the circular dichroism signal as ellipticity (mdeg) at different N/P ratios in the RNA/PEI formulations. FIG. 28C indicates the shift in the peak position (nm) observed in the formulated RNA, as a function of the positive charge concentration (mM) in either PEI or NaCl formulations. The shift in the peak position is calculated with the respective control group (either 0 mM NaCl for the RNA/NaCl formulations or N/P=0 for the RNA/PEI formulations (pure RNA, no PEI)). FIG. 28D indicates the shift in circular dichroism signal as ellipticity (mdeg) at the peak position observed in the formulated RNA, as a function of the positive charges concentration (mM) in either PEI or NaCl formulations. The shift in CD(mdeg) at peak position is calculated with the respective control group (either 0 mM NaCl for the RNA/NaCl formulations or N/P=0 for the RNA/PEI formulations (pure RNA, no PEI)).

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

An aqueous phase consisting of cationic polymer and RNA is described herein, where, instead of RNA-polyplex nanoparticles individual RNA molecules are present in the aqueous phase. The formulation of RNA, solubilized in the polymer-containing solution has favorable transfection characteristics for delivery of the RNA in vitro and in vivo. They are advantageous for pharmaceutical application where RNA needs to be delivered to target cells for various therapeutic approaches. The new phases have been discovered by thorough investigation of the colloidal nature of RNA/polymer systems.

According to the classical understanding of polyplex formulations, increasing the amount of cationic polymer reduces the amount of free RNA, until, close to charge equilibrium and above, no more free RNA is present. The RNA is considered to be completely inserted into the poly-plex nanoparticles, which can have different sizes and typi-cally comprise several RNA and polymer molecule copies.

Thorough investigation of the PEI/RNA system revealed, that, surprisingly, with PEI excess, RNA present as indi-vidually dissolved molecules could be found. Furthermore, even more surprisingly, it was found that the fraction of RNA which was present in the form of such individually dissolved molecules increased with increasing polymer excess. The RNA in the polyplex nanoparticles and the individually dissolved RNA could be separated from each other by centrifugation. FIG. 2 shows results from centrifu-gation experiments, where the RNA content in the superna-tant and the pellet was quantified by UV measurements, Experiments were performed with messenger RNA (mRNA) consisting of about 2000 nucleotides, and self-amplifying RNA (saRNA), consisting of about 9000 nucleotides. For both types of RNA, mRNA and saRNA, a fraction of them was not precipitated under the applied centrifugation con-ditions. The figure demonstrates, that the RNA fraction in the supernatant increased with increasing PEI excess. In FIG. 3, the amounts of precipitated RNA and RNA in the supernatant were summarized for the respective N/P ratios. Values close to 100% of the theoretical concentration were obtained, indicating that the finding were not due to any artifacts, but really correlated to the true RNA concentra-tions.

Particle size measurements from the different fractions as a function of N/P ratio were performed, shown in FIG. 4. Sizes for the unmodified systems after mixing the two components, and after centrifugation, from the re-suspended precipitate and the supernatant are shown. The re-suspended pellets yielded values close to those for the system before centrifugation. Notably, also from the supernatants measure-ments were possible, where the size was between 25 and 50 nm. Although for the size measurements a certain error has to be taken into account, the data indicate in any case, that some particulate fraction was present in the supernatants.

The composition of supernatant fraction was further investigated by agarose gel measurements. FIG. 5 shows agarose gel traces for naked RNA in comparison to super-natants at N/P 12, 36 and 72. The supernatants were mea-sured either untreated, or after incubation with heparin, in order to release eventually PEI-complexed RNA. While for the untreated supernatants no RNA band is visible, it can be detected after the heparin treatment, where the intensity of the bands increases with N/P ratio. This confirms, that, in fact, RNA is present in the supernatants, but not in a free form, rather one may assume that it is present in a PEI-associated state, from which it can be released by the heparin treatment.

More systematic investigation of the supernatant fraction revealed quantitative insight into the shift of the RNA from the nanoparticle to the supernatant phase. In FIG. 6 mea-surements of the supernatant fraction as shown in FIG. 2 were extended to much higher N/P values. The supernatant fraction monotonously increased until all RNA was trans-formed into the non-precipitating state at N/P values of about 130 to 150 (at N/P=120 the supernatant contains depending on the RNA sample 85 to 95% of the RNA). Therefore, at this N/P value the RNA can be considered to be completely transformed into the supernatant state.

Analytical ultracentrifugation (AUC) measurements were used to reveal insight into the molecular coherencies of the RNA in the supernatant state. In FIG. 7A results from AUC measurements at N/P 12 are shown. A large peak at high sedimentation coefficient corresponding to the nanoparticles was determined, and in addition, a sequence of peaks at lower sedimantaion coefficient which are similar to fractions of molecular moieties as a monomer, dimer, trimer, and so on. RNA and PEI peaks can be revealed independently and coincide. Therefore, the RNA in the supernatant is consid-ered to be present in form of RNA monomers, dimers, trimers, and so on, which are solvated with PEI in a quasi-stoiciometric manner. As observed in FIG. 7C, further AUC analysis of N/P increment of PEI-Polyplexes contain-ing iVT mRNA demonstrated that higher N/P ratios shift the system towards individual, monomeric RNA molecules. At N/P=120 all the iVT mRNA is found in a monomeric molecular arrangement.

The observations as outlined here with PEI as an example can be made as well with other cationic polymers, as demonstrated in FIG. 8 or FIG. 20B or FIG. 22B, where RNA phases with a number of alternative cationic polymers as a function of N/P ratio were regarded. In all cases, after centrifugation an increasing solubilized RNA fraction was found with increasing N/P. This demonstrates that the obser-vations and conclusions with PEI as a model molecule are in principle as well applicable for other cationic polymers.

The new PEI/RNA phase at high N/P ratio demonstrated superior transfection efficacy in comparison to the classical polyplex nanoparticle systems. This is demonstrated in FIG. 9, where the results from in vitro transfection experiments are shown. RNA/PEI polyplex systems from luciferase coding RNA were assembled at different N/P ratios, and the luc expression was measured for the complete systems, or after separation of pellet and supernatant by centrifugation. The activity of the supernatant phases increased much more with increasing N/P ration than the total system or the pelleted nanoparticles, which were very low in activity. Thus, apparently, the supernatant phase provided the key contribution to the activity of the systems, while the nan-oparticles seem to be very low in activity or even detrimen-tal. The activity increased monotonously with the N/P ratio up to about a value of 120, above which is seemed to level off. This coincides with the range, where the RNA was quantitatively transferred into the monomeric form (FIG. 10B, 10C). Thus the pure, monomeric RNA as present at N/P 120 and above appears to be most favorable for best trans-fection efficacy.

The observation made in vitro can be as well confirmed in vivo, as shown in FIG. 11-13. Coherently an increase of the transfection efficacy with increasing N/P up to 120 was found. Higher luciferase expression as well as higher titers from immunization experiments were obtained. At the same time, the doses could be reduced, thus allowing to reduce potentially toxic effects of the vehicle. Furthermore, the previous observations at high N/P ratio for superior trans-fection efficacy could be observed for substantially different cationic polymers in FIG. 20C or FIG. 22C, where the activity increased monotonously with the N/P ratio and level off in the range which coincide where the RNA was quan-titatively transferred in the highest possible amount of monomeric form (FIG. 20B or FIG. 22B). This highlights the universal application of the enhanced biological activity of such RNA/PEI systems for other cationic polymers.

Definitions

In the following, definitions will be provided which apply to all aspects of the present disclosure. The following terms have the following meanings unless otherwise indicated. Any undefined terms have their art recognized meanings.

Terms such as "reduce" or "inhibit" as used herein means the ability to cause an overall decrease, for example, of about 5% or greater, about 10% or greater, about 20% or greater, about 50% or greater, or about 75% or greater, in the level. The term "inhibit" or similar phrases includes a complete or essentially complete inhibition, i.e. a reduction to zero or essentially to zero.

Terms such as "increase" or "enhance" in one embodiment relate to an increase or enhancement by at least about 10%, at least about 20%, at least about 30%, at least about 40%, at least about 50%, at least about 80%, or at least about 100%.

As used herein, the t "aqueous phase" refers to a composition comprising in whole, or in part, water.

"Physiological pH" as used herein refers to a pH of about 7.5.

As used in the present disclosure, "% w/v" refers to weight by volume percent, which is a unit of concentration measuring the amount of solute in grams (g) expressed as a percent of the total volume of solution in milliliters (mL).

As used in the present disclosure, "mol %" is defined as the ratio of the number of moles of one component to the total number of moles of all components, multiplied by 100.

Some percentages are given in weight percent, i.e., in "wt %". The term "wt %" denotes a weight percent based on the total weight of a compound or composition.

The term "mass fraction," as used herein, refers to the mass ratio of a component to the total mass. Here, the mass fraction is typically expressed as percent (%) (often called percentage by weight, abbreviated wt %). For example, a mass fraction of RNA present in a certain molecularity of higher than 60% means that more than 60% of the RNA (on a mass basis) of the total amount of RNA in a composition is present in this certain molecularity.

The term "ionic strength" refers to the mathematical relationship between the number of different kinds of ionic species in a particular solution and their respective charges. Thus, ionic strength I is represented mathematically by the formula $$I = \frac{1}{2} \cdot \sum_i z_i^2 \cdot c_i$$

in which c is the molar concentration of a particular ionic species and z the absolute value of its charge. The sum $\Sigma$ is taken over all the different kinds of ions (i) in solution.

According to the disclosure, the term "ionic strength" in one embodiment relates to the presence of monovalent ions. Regarding the presence of divalent ions, in particular divalent cations, their concentration or effective concentration (presence of free ions) due to the presence of chelating agents is in one embodiment sufficiently low so as to prevent degradation of the RNA. In one embodiment, the concentration or effective concentration of divalent ions is below the catalytic level for hydrolysis of the phosphodiester bonds between RNA nucleotides. In one embodiment, the concentration of free divalent ions is 20 µM or less. In one embodiment, there are no or essentially no free divalent ions.

"Osmolality" refers to the concentration of solutes expressed as the number of osmoles of solute per kilogram of solvent.

The term "freezing" relates to the solidification of a liquid, usually with the removal of heat. The term "lyophilizing" or "lyophilization" refers to the freeze-drying of a substance by freezing it and then reducing the surrounding pressure to allow the frozen medium in the substance to sublimate directly from the solid phase to the gas phase.

The term "spray-drying" refers to spray-drying a substance by mixing (heated) gas with a fluid that is atomized (sprayed) within a vessel (spray dryer), where the solvent from the formed droplets evaporates, leading to a dry powder.

The term "cryoprotectant" relates to a substance that is added to a formulation in order to protect the active ingredients during the freezing stages.

The term "lyoprotectant" relates to a substance that is added to a formulation in order to protect the active ingredients during the drying stages.

The term "reconstitute" relates to adding a solvent such as water to a dried product to return it to a liquid state such as its original liquid state.

The term "recombinant" in the context of the present disclosure means "made through genetic engineering". In one embodiment, a "recombinant object" in the context of the present disclosure is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

In the context of the present disclosure, the term "particle" relates to a structured entity formed by molecules or molecule complexes. In one embodiment, the term "particle" relates to a micro- or nano-sized structure, such as a micro- or nano-sized compact structure.

In the context of the present disclosure, the term "RNA particle" relates to a particle that contains RNA. In one embodiment, a RNA particle is a nanoparticle.

As used in the present disclosure, "nanoparticle" refers to a particle preferably having an average diameter of at least about 50 nm.

The term "average diameter" refers to the mean hydrodynamic diameter of particles as measured by dynamic laser light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The "polydispersity index" is preferably calculated based on dynamic light scattering measurements by the so-called cumulant analysis as mentioned in the definition of the "average diameter". Under certain prerequisites, it can be taken as a measure of the size distribution of an ensemble of nanoparticles.

The term "aggregate" or "complex" as used herein means a plurality of (at least two) molecules which form larger unities, e.g., particles, comprising said plurality of molecules. Therein, the individual molecules are no longer present independently. Aggregation is a process whereby individual molecules associate non-covalently to form aggregates. Electrostatic interactions between positively charged molecules such as polymers and negatively charged RNA may be involved in aggregate formation. This results in complexation and spontaneous formation of RNA aggregates or RNA particles.

The term "RNA aggregate" as used herein means an aggregate or unit comprising a plurality of (at least two) RNA molecules. This term thus excludes polyplexes of one RNA molecule and one or more polymer molecules, which polyplexes are also included herein by the term "individual", "monomolecular", "unimolecular" or "monomer" when used in respect of RNA. The term "aggregate comprising a large number of RNA molecules" or simply "large RNA aggregate" or "large aggregate" as used herein means a RNA aggregate comprising 6 or more, 7 or more, 8 or more, 9 or more, 10 or more, 15 or more, 20 or more, 25 or more, or 50 or more RNA molecules, or even more RNA molecules.

The term "polyplex" as used herein refers to an association of a polymer and a nucleic acid such as RNA formed via electrostatic interactions. In cases where the polyplex comprises RNA, the term also may be referred to as "RNA polyplex".

The term "individual molecule", "monomolecular", "unimolecular", or "monomer" as used herein means that a molecule is not present as a plurality of (at least two) molecules of the same type and does not form larger unities with other molecules of the same type by physical interactions. In particular, the term "individual molecule", "monomolecular", "unimolecular", or "monomer" as used herein shall refer to a unit only containing one RNA molecule. Said unit may comprise any number of molecules of compounds other than the RNA, e.g., polymer. Multimolecular RNA units (the latter each contain more than one RNA molecule) may be distinguished by the different size of each of the units. Typically, the term "individual molecule", "monomolecular", "unimolecular", or "monomer" as used herein includes RNA associated with polymer, wherein the polymer and the RNA do not form units with more than one RNA molecule per unit but rather monomolecular RNA units. In one embodiment, a single RNA molecule is associated with cationic polymer without intermolecular aggregation of the RNA.

In the present context the term "fraction" relates to a portion, e.g., a portion of RNA, which may be separated from other fractions by a fractionation process, such as filtration, centrifugation, or chromatography. In one embodiment, a fraction may relate to units (e.g., RNA molecule-polymer complexes) having a defined number of RNA molecules, e.g., one, two, three, four, five etc. RNA molecules, per unit. For example, different fractions may relate to the unimolecular RNA fraction, bimolecular RNA fraction, trimolecular RNA fraction, tetramolecular RNA fraction, pentamolecular RNA fraction etc., containing one, two, three, four, five etc. RNA molecules, per unit. Such different numbers of RNA molecules per unit is also designated as "molecularity" herein.

The term "predominant fraction" as used herein means the fraction of RNA of a certain molecularity, e.g., unimolecular RNA fraction, bimolecular RNA fraction, trimolecular RNA fraction, tetramolecular RNA fraction, pentamolecular RNA fraction etc., which contains the most RNA (on a mass basis). For example, if in a composition comprising 30 ng RNA, 10 ng of the RNA are in the unimolecular RNA fraction, 8 ng of the RNA are in the bimolecular RNA fraction, 6 ng of the RNA are in the trimolecular RNA fraction, 4 ng of the RNA are in the tetramolecular RNA fraction, and 2 ng of the RNA are in the pentamolecular RNA fraction, the unimolecular RNA fraction is the predominant fraction, despite of the fact that most of the RNA is in fractions other than the unimolecular RNA fraction. If a composition only comprises one type of RNA molecules, the predominant fraction is the fraction of RNA of a certain molecularity containing the highest number of RNA molecules of all fractions.

One of the commonly used practices to quantitate RNA is the use of spectrophotometric analysis using a spectrophotometer. Spectrophotometric analysis is based on the principles that nucleic acids absorb ultraviolet light in a specific pattern. In the case of RNA, a sample is exposed to ultraviolet light at a wavelength of about 260 nanometres (nm) and a photo-detector measures the light that passes through the sample. Some of the ultraviolet light will pass through and some will be absorbed by the RNA. The more light absorbed by the sample, the higher the RNA concentration in the sample.

According to the present invention, the terms "N/P ratio", "NP ratio", "N:P ratio", "N/P" and "NP" refer to the molar ratio of nitrogen atoms (N) in the polymer such as polyethylenimine to phosphor atoms (P) in the RNA.

RNA Compositions

The present disclosure describes compositions comprising RNA and one or more polymers wherein a large fraction of the RNA is present as individual molecules in solution. The polymer may be associated to the RNA in different forms by non-covalent interactions to the RNA. The RNA described herein is not present as viral particles, in particular infectious viral particles, i.e., it is not able to virally infect cells. A RNA composition described herein is typically formed from RNA and a cationic polymer such as poly (ethyleneimine). In some embodiments, RNA compositions comprise more than one type of RNA molecules, where the molecular parameters of the RNA molecules may be similar or different from each other, like with respect to molar mass or fundamental structural elements such as molecular architecture, capping, coding regions or other features.

Typically, cationic polymers are used which may electrostatically bind the negatively charged RNA. These positively charged groups often consist of amines that change their state of protonation in the pH range between 5.5 and 7.5, thought to lead to an ion imbalance that results in endosomal rupture. Naturally occurring polymers such as chitosan and synthesized polymers can be used herein.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties.

If more than one type of repeat unit is present within the polymer, then the polymer is said to be a "copolymer." It is to be understood that in any embodiment employing a polymer, the polymer being employed can be a copolymer in some cases. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, the polymer is biocompatible. Biocompatible polymers are polymers that typically do not result in significant cell death at moderate concentrations. In certain embodiments, the biocompatible polymer is biodegradable, i.e., the polymer is able to degrade, chemically and/or biologically, within a physiological environment, such as within the body. In the context of the present invention, a cationic or polycationic polymer is preferably selected from any cationic or polycationic polymer suitable for formulating RNA as described herein.

Particularly preferred cationic or polycationic polymers are:

cationic or polycationic peptides or proteins, in particular, nucleic acid binding peptides or proteins, which may be selected from protamine, histone, spermine, spermidine, poly-arginine, poly-lysine such as poly-L-(lysine) (PLL);

cationic polysaccharides, for example chitosan, diethylaminoethyl (DEAE) dextrans; or cationic or polycationic polymers, e.g. polyimine(s), such as polyethylenimine (PEI), poly(propyleneimine), poly(amidoamine) (PAA), polyaminoester (PAE), in particular poly (β-amino esters), poly(allylamines), polyvinylamine, poly (dimethylaminoethyl methacrylates), hexadimethrine bromide (commercial brand name Polybrene).

In certain embodiments, the polymer may be polyalkyleneimine such as polyethylenimine (PEI).

In one embodiment, the polymer comprises a polyamidoamine (PAMAM) polymer. Poly(amidoamine), or PAMAM, is a class of dendrimer which is made of repetitively branched subunits of amide and amine functionality. PAMAM dendrimers have a sphere-like shape overall, and are typified by an internal molecular architecture consisting of tree-like branching, with each outward "layer", or generation, containing exponentially more branching points. This branched architecture distinguishes PAMAMs and other dendrimers from traditional polymers, as it allows for low polydispersity and a high level of structural control during synthesis, and gives rise to a large number of surface sites relative to the total molecular volume. In one embodiment, a PAMAM is functionalized with L-lysine polymers.

Polyalkyleneimines

Polyalkyleneimines for use herein comprise linear and branched polyalkyleneimines and mixtures thereof. The average molecular weight of the polyalkyleneimine is preferably between 1000 Da and 150000 Da, between 5000 Da and 100000 Da, between 10000 Da and 50000 Da, between 15000 Da and 30000 Da, between 20000 Da and 25000 Da, or about 22500 Da. The polyalkyleneimine as used herein preferably comprises the following general formula (I):

$$\left[\begin{array}{c} N-(CH_2)_n \\ | \\ R \end{array}\right]_p ,$$

wherein

R is H, an acyl group or a group comprising the following general formula (II):

$$\left[ (CH_2)_m - \begin{array}{c} N \\ | \\ R_1 \end{array} \right]_q ,$$

wherein $R_1$ is H or a group comprising the following general formula (III):

$$\left[ (CH_2)_l - NH \right]_r ,$$

n, m, and l are independently selected from integers from 2 to 10; and p, q, and r are integers, wherein the sum of p, q, and r is preferably such that the average molecular weight of the polymer is between 1000 Da and 100000 Da, between 5000 Da and 75000 Da, between 10000 Da and 50000 Da, between 15000 Da and 30000 Da, between 20000 Da and 25000 Da, or about 20000 Da.

In one embodiment, n, m, and l are independently selected from 2, 3, 4, and 5, preferably from 2 and 3, and more preferably are 2. In one embodiment, $R_1$ is H. In one embodiment, R is H or an acyl group.

In one embodiment, the polyalkyleneimine comprises polyethylenimine and/or polypropyleneimine, preferably polyethylenimine.

A preferred polyalkyleneimine is polyethylenimine (PEI). The average molecular weight of PEI is preferably between 1000 Da and 100000 Da, between 5000 Da and 75000 Da, between 10000 Da and 50000 Da, between 15000 Da and 30000 Da, between 20000 Da and 25000 Da, or about 20000 Da. Preferred according to the invention is linear PEI. In one embodiment, linear PEI is obtained by a ring-opening isomerization polymerization of 2-ethyl-2-oxazoline to obtain poly(2-ethyl-2-oxazoline) (PEOX; N-propionyl-PEI), which is then acid-hydrolyzed to cleave off the N-propionyl groups to yield PEI.

RNA Concentration

In certain embodiments of the present disclosure, the RNA in the compositions described herein is at a concentration from about 0.0001 mg/mL to about 1 mg/mL, from about 0.0001 mg/mL to about 0.5 mg/mL, from about 0.00025 mg/mL to about 0.5 mg/mL, from about 0.0005 mg/mL to about 0.25 mg/mL, from about 0.0025 mg/mL to about 0.1 mg/mL or from about 0.005 mg/mL to about 0.1 mg/mL. In specific embodiments, the RNA is at a concentration from about 0.00025 mg/mL to about 0.1 mg/mL, from about 0.00025 mg/mL to about 0.09 mg/mL, from about 0.00025 mg/mL to about 0.08 mg/mL, from about 0.00025 mg/mL to about 0.07 mg/mL, from about 0.00025 mg/mL to about 0.06 mg/mL, or from about 0.00025 mg/mL to about 0.05 mg/mL.

RNA

In the present disclosure, the term "RNA" relates to nucleic acid molecules which include ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In certain embodiments of the present disclosure, the RNA is replicon RNA or simply "a replicon", in particular self-replicating RNA (self-amplifying RNA; saRNA). In one particularly preferred embodiment, the replicon or self-replicating RNA is derived from or comprises elements derived from a ssRNA virus, in particular a positive-stranded ssRNA virus such as an alphavirus. Alphaviruses are typical representatives of positive-stranded RNA viruses. Alphaviruses replicate in the cytoplasm of infected cells (for review of the alphaviral life cycle see José et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP 1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1. In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e., at early stages of the viral life cycle, the (+) stranded genomic RNA directly acts like a messenger RNA for the translation of the open reading frame encoding the non-structural poly-protein (nsP1234). Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase, and the other nucleic acid molecule is capable of being replicated by said replicase in trans (hence the designation trans-replication system). Trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

In one embodiment, the RNA may have modified ribonucleotides. Examples of modified ribonucleotides include, without limitation, 5-methylcytidine, pseudouridine ($\Psi$), N1-methyl-pseudouridine ($m^1\Psi$) or 5-methyl-uridine ($m^5U$).

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, the RNA according to the present disclosure comprises a 3'-poly(A) sequence. The term "poly (A) sequence" relates to a sequence of adenyl (A) residues which typically is located at the 3'-end of a RNA molecule. According to the disclosure, in one embodiment, a poly(A) sequence comprises at least about 20, at least about 40, at least about 80, or at least about 100, and up to about 500, up to about 400, up to about 300, up to about 200, or up to about 150 A nucleotides, and in particular about 120 A nucleotides. In one embodiment, the poly(A) sequence may be interrupted by one or more short sequences of e.g. between 5 and 20 nucleotides containing nucleotides other than A nucleotides.

In the context of the present disclosure, the term "transcription" relates to a process, wherein the genetic code in a DNA sequence is transcribed into RNA. Subsequently, the RNA may be translated into peptide or protein.

With respect to RNA, the term "expression" or "translation" relates to the process in the ribosomes of a cell by which a strand of mRNA directs the assembly of a sequence of amino acids to make a peptide or protein.

RNA can be coding RNA, i.e., RNA encoding a peptide or protein. Said RNA may express the encoded peptide or protein. For example, said RNA may be RNA encoding and expressing a pharmaceutically active peptide or protein. Alternatively, the RNA can be non-coding RNA such as antisense-RNA, micro RNA (miRNA) or siRNA.

RNA used herein may be pharmaceutically active RNA. A "pharmaceutically active RNA" is a RNA that encodes a pharmaceutically active peptide or protein or is pharmaceutically active in its own, e.g., it has one or more pharmaceutical activities such as those described for pharmaceutically active proteins, e.g., immunostimulatory activity. For example, the RNA may be one or more strands of RNA interference (RNAi). Such agents include short interfering RNAs (siRNAs), or short hairpin RNAs (shRNAs), or precursor of a siRNA or microRNA-like RNA, targeted to a target transcript, e.g., a transcript of an endogenous disease-related transcript of a subject.

Some aspects of the disclosure involve the targeted delivery of the RNA disclosed herein to certain cells or tissues. In one embodiment, the disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding an antigen or epitope for inducing an immune response. In one embodiment, the target cell is a spleen cell. In one embodiment, the target cell is an antigen presenting cell such as a professional antigen presenting cell in the spleen. In one embodiment, the target cell is a dendritic cell in the spleen. The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naive lymphocytes and initiate an adaptive immune response.

In one embodiment, the target organ is liver and the target tissue is liver tissue. The delivery to such target tissue is preferred, in particular, if presence of RNA or of the encoded peptide or protein in this organ or tissue is desired and/or if it is desired to express large amounts of the encoded peptide or protein and/or if systemic presence of the encoded peptide or protein, in particular in significant amounts, is desired or required.

In one embodiment, after administration of the RNA compositions described herein, at least a portion of the RNA is delivered to a target cell or target organ. In one embodiment, at least a portion of the RNA is delivered to the cytosol of the target cell. In one embodiment, the RNA is RNA encoding a peptide or protein and the RNA is translated by the target cell to produce the peptide or protein. In one embodiment, the target cell is a cell in the liver. In one embodiment, the target cell is a muscle cell. In one embodiment, the target cell is an endothelial cell. In one embodiment the target cell is a tumor cell or a cell in the tumor microenvironment. In one embodiment, the target cell is a blood cell. In one embodiment, the target cell is a cell in the lymph nodes. In one embodiment, the target cell is a cell in the lung. In one embodiment, the target cell is a cell in the skin. In one embodiment, the target cell is a spleen cell. In one embodiment, the target cell is an antigen presenting cell such as a professional antigen presenting cell in the spleen. In one embodiment, the target cell is a dendritic cell in the spleen. In one embodiment, the target cell is a T cell. In one embodiment, the target cell is a B cell. In one embodiment, the target cell is a NK cell. In one embodiment, the target cell is a monocyte. Thus, RNA compositions described herein may be used for delivering RNA to such target cell. Accordingly, the present disclosure also relates to a method for delivering RNA to a target cell in a subject comprising the administration of the RNA compositions described herein to the subject. In one embodiment, the RNA is delivered to the cytosol of the target cell. In one embodiment, the RNA is RNA encoding a peptide or protein and the RNA is translated by the target cell to produce the peptide or protein.

In an embodiment, RNA encodes a pharmaceutically active peptide or protein.

According to the disclosure, the term "RNA encodes" means that the RNA, if present in the appropriate environment, such as within cells of a target tissue, can direct the assembly of amino acids to produce the peptide or protein it encodes during the process of translation. In one embodiment, RNA is able to interact with the cellular translation machinery allowing translation of the peptide or protein. A cell may produce the encoded peptide or protein intracellularly (e.g. in the cytoplasm and/or in the nucleus), may secrete the encoded peptide or protein, or may produce it on the surface.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" refers to large peptides, in particular peptides having at least about 151 amino acids, but the terms "peptide" and "protein" are used herein usually as synonyms.

A "pharmaceutically active peptide or protein" or "therapeutic peptide or protein" has a positive or advantageous effect on a condition or disease state of a subject when provided to the subject in a therapeutically effective amount. In one embodiment, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein.

Examples of pharmaceutically active proteins include, but are not limited to, cytokines and derivatives thereof such as cytokine-fusions (like albumin-cytokine fusions) and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, chimeric antigen receptors (CARs), immuno-globulins including antibodies or bispecific antibodies, e.g., for immune stimulation or production of neutralizing antibodies in case of viral/bacterial infection, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases, lysosomal enzymes and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

The term "immunologically active compound" relates to any compound altering an immune response, for example, by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants.

In one embodiment, a pharmaceutically active peptide or protein comprises a cytokine. The term "cytokine" refers to a category of small proteins (~5-20 kDa) that are important in cell signalling. Their release has an effect on the behavior of cells around them. Cytokines are involved in autocrine signalling, paracrine signalling and endocrine signalling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways. In one embodiment, the pharmaceutically active protein according to the invention is a cytokine which is involved in regulating lymphoid homeostasis, preferably a cytokine which is involved in and preferably induces or enhances development, priming, expansion, differentiation and/or survival of T cells. In one embodiment, the cytokine is an interleukin. In one embodiment, the pharmaceutically active protein according to the invention is an interleukin selected from the group consisting of IL-2, IL-7, IL-12, IL-15, and IL-21.

In one embodiment, a pharmaceutically active peptide or protein comprises a replacement protein. In this embodiment, the present invention provides a method for treatment of a subject having a disorder requiring protein replacement (e.g., protein deficiency disorders) comprising administering to the subject RNA as described herein encoding a replacement protein. The term "protein replacement" refers to the introduction of a protein (including functional variants thereof) into a subject having a deficiency in such protein. The term also refers to the introduction of a protein into a subject otherwise requiring or benefiting from providing a protein, e.g., suffering from protein insufficiency. The term "disorder characterized by a protein deficiency" refers to any disorder that presents with a pathology caused by absent or insufficient amounts of a protein. This term encompasses protein folding disorders, i.e., conformational disorders, that result in a biologically inactive protein product. Protein insufficiency can be involved in infectious diseases, immunosuppression, organ failure, glandular problems, radiation illness, nutritional deficiency, poisoning, or other environmental or external insults. In one embodiment, a pharmaceutically active peptide or protein comprises one or more antigens or one or more epitopes, i.e., administration of the peptide or protein to a subject elicits an immune response against the one or more antigens or one or more epitopes in a subject which may be therapeutic or partially or fully protective.

The term "antigen" relates to an agent comprising an epitope against which an immune response can be generated. The term "antigen" includes, in particular, proteins and peptides. In one embodiment, an antigen is presented by cells of the immune system such as antigen presenting cells like dendritic cells or macrophages. An antigen or a processing product thereof such as a T cell epitope is in one embodiment bound by a T or B cell receptor, or by an immunoglobulin molecule such as an antibody. Accordingly, an antigen or a processing product thereof may react specifically with antibodies or T-lymphocytes (T-cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "epitope" refers to a part or fragment a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specific T cell" or similar terms relate to a T cell which recognizes the antigen to which the T cell is targeted, in particular when presented on the surface of antigen presenting cells or diseased cells such as cancer cells in the context of MHC molecules and preferably exerts effector functions of T cells. T cells are considered to be specific for antigen if the cells kill target cells expressing an antigen. T cell specificity may be evaluated using any of a variety of standard techniques, for example, within a chromium release assay or proliferation assay. Alternatively, synthesis of lymphokines (such as interferon-γ) can be measured.

In certain embodiments of the present disclosure, the RNA encodes at least one epitope. In certain embodiments, the epitope is derived from a tumor antigen. The tumor antigen may be a "standard" antigen, which is generally known to be expressed in various cancers. The tumor antigen may also be a "neo-antigen", which is specific to an individual's tumor and has not been previously recognized by the immune system. A neo-antigen or neo-epitope may result from one or more cancer-specific mutations in the genome of cancer cells resulting in amino acid changes. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUD IN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, GE-A2, MAGE-A3, MAGE-A4, MAGE-A5, MAGE-A6, MAGE-A7, MAGE-A8, MAGE-A9, MAGE-A 10, MAGE-A 11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pm1/RaRa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a "pentatope") and RNA that encodes at least ten epitopes (termed a "decatope").

A. Salt and Ionic Strength

According to the present disclosure, the compositions described herein may comprise salts such as organic or inorganic salts, including, but not limited to, sodium chloride, potassium chloride, dipotassium phosphate, monopotassium phosphate, potassium acetate, potassium bicarbonate, potassium sulfate, potassium acetate, disodium phosphate, monosodium phosphate, sodium acetate, sodium bicarbonate, sodium sulfate, sodium acetate, lithium chloride, magnesium chloride, magnesium phosphate, calcium chloride, and sodium salts of ethylenediaminetetraacetic acid (EDTA) and amino acids.

Generally, compositions described herein comprise salts at a concentration that preferably ranges from 0 mM to about 100 mM, from about 5 mM to about 50 mM, or from about 5 mM to about 20 mM. In one embodiment, compositions comprise an ionic strength corresponding to such salt concentrations.

In one embodiment, positively charged monovalent ions such as sodium chloride are at a concentration from 0 mM to about 50 mM, from 0 mM to about 40 mM, or from about 10 mM to about 20 mM.

In one embodiment, positively charged divalent ions are at a concentration (or an effective concentration) from 0 mM to about 20 μM, from 0 mM to about 10 μM, or from about 0 mM to about 5 μM.

B. Stabilizer

Compositions described herein may also comprise a stabilizer to avoid substantial loss of the product quality and, in particular, substantial loss of RNA activity during storage, freezing, lyophilization and/or spray-drying, for example to reduce or prevent aggregation, RNA degradation and/or other types of damage.

In an embodiment, the stabilizer is a cryoprotectant or lyoprotectant.

In an embodiment the stabilizer is a carbohydrate. The term "carbohydrate", as used herein refers to and encompasses monosaccharides, disaccharides, trisaccharides, oligosaccharides and polysaccharides. In an embodiment, the stabilizer is sucrose and/or trehalose.

In an embodiment, the stabilizer is an amino acid or a surfactant (e.g. poloxamer)

C. pH and Buffer

According to the present disclosure, the compositions described herein have a pH suitable for the stability of the compositions and, in particular, for the stability of the RNA. In one embodiment, the compositions described herein have a pH from about 4 to about 8, from about 5 to about 7, or from about 5.5 to about 6.5.

Without wishing to be bound by theory, the use of buffer maintains the pH of the composition during manufacturing, storage and use of the composition. In certain embodiments of the present disclosure, the buffer may be sodium bicarbonate, monosodium phosphate, disodium phosphate, monopotassium phosphate, dipotassium phosphate, [tris(hydroxymethyl)methylamino]propanesulfonic acid (TAPS), 2-(Bis(2-hydroxyethyl)amino)acetic acid (Bicine), 2-Amino-2-(hydroxymethyl)propane-1,3-diol (Tris), N-(2-Hydroxy-1,1-bis(hydroxymethyl)ethyl)glycine (Tricine), 3-[[1,3-dihydroxy-2-(hydroxymethyl) propan-2-yl]amino]-2-hydroxypropane-1-sulfonic acid (TAPSO), 2-[4-(2-hydroxyethyl)piperazin-1-yl]ethanesulfonic acid (HEPES), 2-[[1,3-dihydroxy-2-(hydroxymethyl)propan-2-yl]amino] ethanesulfonic acid (TES), 1,4-piperazinediethanesulfonic acid (PIPES), dimethylarsinic acid, 2-morpholin-4-ylethanesulfonic acid (MES), 3-morpholino-2-hydroxypropanesulfonic acid (MOPSO), or phosphate buffered saline (PBS). Other suitable buffering systems may be acetic acid alone or in a salt, citric acid alone or in a salt, boric acid alone or in a salt and phosphoric acid alone or in a salt, or amino acids and amino acid derivatives.

In certain embodiments, the buffer has a concentration from about 2.5 mM to about 20 mM or about 2.5 mM to about 10 mM.

D. Chelating Agent

Certain embodiments of the present disclosure contemplate the use of a chelating agent in a composition described herein. Chelating agents refer to chemical compounds that are capable of forming at least two coordinate covalent bonds with a metal ion, thereby generating a stable, water-soluble complex. Without wishing to be bound by theory, chelating agents reduce the concentration of free divalent ions, which may otherwise induce accelerated RNA degradation in the present disclosure. Examples of suitable chelating agents include, without limitation, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid (DTPA), bis(aminoethyl)glycolether-N,N,N',N'-tetraacetic acid, iminodiacetic acid, citric acid, tartaric acid, fumaric acid, or a salt thereof. In certain embodiments, the chelating agent is EDTA or a salt of EDTA. In an exemplary embodiment, the chelating agent is EDTA disodium dihydrate.

In some embodiments, the EDTA is at a concentration from about 0.05 mM to about 5 mM, from about 0.1 mM to about 2.5 mM or from about 0.25 mM to about 1 mM.

E. Physical State of Compositions

In embodiments, the composition of the present disclosure is a liquid or a solid. Non-limiting examples of a solid include a frozen form, or a dehydrated form such as a lyophilized form or a spray-dried form. In a preferred embodiment, the composition is a liquid.

Pharmaceutical Compositions

The compositions described herein are useful as or for preparing pharmaceutical compositions or medicaments for therapeutic or prophylactic treatments.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as Bordetella pertussis toxin), or immune-stimulating complexes. Examples of adjuvants include, without limitation, LPS, GP96, CpG oligodeoxy-nucleotides, growth factors, and cyctokines, such as monokines, lymphokines, interleukins, chemokines. The chemokines may be IL-1, IL-2, IL-3, IL-4, IL-5, IL-6, IL-7, IL-8, IL-9, IL-10, IL-12, INFa, INF-γ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys, as well as lipophilic components, such as saponins, trehalose-6,6-dibehenate (TDB), monophosphoryl lipid-A (MPL), monomycoloyl glycerol (MMG), or glucopyranosyl lipid adjuvant (GLA).

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

Routes of Administration of Pharmaceutical Compositions

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intramuscular, intradermal, subcutaneous or intravenous injection. In a preferred embodiment, the pharmaceutical composition is formulated for intramuscular administration.

Use of Pharmaceutical Compositions

Compositions described herein may be used in the therapeutic or prophylactic treatment of various diseases, in particular diseases in which provision of a peptide or protein to a subject results in a therapeutic or prophylactic effect. For example, provision of an antigen or epitope which is derived from a virus may be useful in the treatment of a viral disease caused by said virus. Provision of a tumor antigen or epitope may be useful in the treatment of a cancer disease wherein cancer cells express said tumor antigen. Provision of a functional protein or enzyme may be useful in the treatment of genetic disorder characterized by a dysfunctional protein, for example in lysosomal storage diseases (e.g. Mucopolysaccharidoses) or factor deficiencies. Provision of a cytokine or a cytokine-fusion may be useful to modulate tumor microenvironment.

The term "disease" (also referred to as "disorder" herein) refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate). or any other non-mammal animal, including birds (chicken), fish or any other animal species that can be afflicted with or is susceptible to a disease or disorder (e.g., cancer, infectious diseases) but may or may not have the disease or disorder, or may have a need for prophylactic intervention such as vaccination, or may have a need for interventions such as by protein replacement. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide protection against an infectious disease by vaccination.

In one embodiment of the disclosure, the aim is to provide secreted therapeutic proteins, such as antibodies, bispecific antibodies, cytokines, cytokine fusion proteins, enzymes, to a subject, in particular a subject in need thereof.

In one embodiment of the disclosure, the aim is to provide a protein replacement therapy, such as production of erythropoietin, Factor VII, Von Willebrand factor, β-galactosidase, Alpha-N-acetylglucosaminidase, to a subject, in particular a subject in need thereof.

In one embodiment of the disclosure, the aim is to modulate/reprogram immune cells in the blood.

A pharmaceutical composition as described herein comprising RNA encoding a peptide or protein that comprises one or more antigens or one or more epitopes may be administered to a subject to elicit an immune response against the one or more antigens or one or more epitopes in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

The terms "immunization" or "vaccination" describe the process of administering an antigen to an individual with the purpose of inducing an immune response, for example, for therapeutic or prophylactic reasons.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Materials and Methods

Preparation of PEI Formulations

Linear Polyethylenimine of 20 to 25 kDa molecular weight is used (in vivo/Jet-PEI). For the calculation of the N/P ratio of the polyplex formulations the positive charges of nitrogen atoms of amines (N) in PEI and anionic charges (phosphates) of the RNA (P) are taken into consideration. The required concentration of RNA is prepared in the final injection buffer. In a separate tube, PEI for the formulation is diluted in injectable $H_2O$. Complexation of RNA will take place by mixing RNA-PEI phases of desired volume ratios. The formulations are incubated 15 min at room temperature for stabilization. The buffer used for the formulations in all experiments is MGB (MES buffered Glucose (10 mM MES, pH6.1, 5% D-Glucose))

Preparation of Formulations Using Viromer®, Aliphatic/Aromatic Substituted Polyalkylenimine Viromer® is a commercially available branched-PEI heavily modified with alkyl chains and aromatic motifs. For the calculation of the N/P ratio of the Viromer® formulations the positive charges of nitrogen atoms of amines (N) in Viromer® and anionic charges (phosphates) of the RNA (P) are taken into consideration. The required concentration of RNA is prepared in the final injection buffer. In a separate tube, Viromer® for the formulation is diluted in injectable $H_2O$. Complexation of RNA will take place by mixing RNA-Viromer phases of desired volume ratios. The formulations are incubated 15 min at room temperature for stabilization. The buffer used for the formulations in all experiments is MGB (MES buffered Glucose (10 mM MES, pH6.1, 5% D-Glucose))

Preparation of Star-Shaped Poly-L-Lysine PAMAM Dendrimer (G5-PLL64) Formulations A novel biodegradable cationic polymer of the poly(amidoamine)s family, which consists of a G(5)-PAMAM dendrimer functionalized with 64 arms of penta-L-Lysine polymers For the calculation of the N/P ratio of the polyplex formulations the positive charges of nitrogen atoms of amines (N) in G5-PLL64 and anionic charges (phosphates) of the RNA (P) are taken into consideration. The required concentration of RNA is prepared in the final injection buffer. In a separate tube, G5-PLL64 for the formulation is diluted in injectable $H_2O$. Complexation of RNA will take place by mixing RNA-G5-PLL64 phases of desired volume ratios. The formulations are incubated 15 min at room temperature for stabilization. The buffer used for the formulations in all experiments is MGB (MES buffered Glucose (10 mM MES, pH6.1, 5% D-Glucose))

Luciferase & Viability Assays

Formulated nanoparticles are diluted accordingly to reach the desired concentration in culture medium. 96-well plates are seeded with 5.000 C2C12 cells/well. After 24 hrs of seeding, medium is aspirated and 100 μl of culture medium with the diluted formulation is applied. The plates are further maintained in cell incubator till desired time point is reached. For luciferase measurement and viability measurements, Nano-Glo and Cell Titer Glo 2.0 manufacturers' protocol is strictly followed. Luminescence measurements are done in Tecan Infinite Pro200 in white bottom plates.

Size Measurement

All size measurements here are done by DynaPro PlateReader II, using dynamic light scattering (DLS) for calculating the hydrodynamic size of nanoparticles. The formulations are measured by diluting the sample to 0.01 mg/ml RNA in 120 μl of MGB5% in wells of a 96-well plate. Ten data points are recorded per well, each lasting 10 seconds.

RNA Quantification

RNA concentration is quantified with Nanodrop. The microvolume option is used for the quantification of RNA, more specifically 1.5 μl of formulated RNA are used. For the calculation of the RNA concentration, 260/280 and 260/230 nm purity radios are taken into account. Only data which fulfilled purity criteria is used in the quantification of RNA. Purity criteria is defined by 1.8-2.2 for 260/280 nm ratio and >1.8 for 260/230 nm ratio. Formulation Buffer is used as blanking solution for the RNA quantification of each sample.

Free RNA Quantification

Free RNA in the formulation is measured by agarose gel electrophoresis under denaturing conditions. 100 ml of 1% Agarose in TAE Buffer is used. 10 μl of GelRed are added prior gel solidification for RNA fluorescent labeling. A formulation sample containing 1 μg of RNA is diluted with gel loading buffer to a final volume of 12 μl. This is placed in agarose gel and the samples are run at 80V, 50 mA for 40 minutes. UV-fluorescence is measured after 0.1 seconds of exposure time.

Centrifugation Assay

Samples are centrifuged at 20.000 G for 90 min at 4° C. After centrifugation, 90% of the supernatant is transferred to a new vial. The pellet remaining after centrifugation is then resuspended with an equal volume as the 90% of supernatant previously transferred.

Ultra-Centrifugation Assay

Samples are measured with analytic ultracentrifuge and light absorption is measured at two different wavelengths:

255 nm and 650 nm. MBG sample buffer is used as blank sample for the measurements. Samples are centrifuged at 80.000 G at RT.

PEI Concentration Assay

PEI concentration is determined by the quantification of reduced copper(II) sulfate. The amount of reduced copper is proportional to the amount of secondary amines present in the solution. 1.4 mM solution of copper(II) sulfate is prepared using 0.1M of Sodium Acetate at pH 5.4. Calibration curve of a known PEI reference is prepared for a maximum of 1.55 mM. Formulated samples are diluted to 0.2 mg/ml of formulated RNA and mixed 1:1 with the copper(II) sulfate solution to a final volume of 300 μl. Absorption of reduced copper is measured at 285 nm.

RNA Release Assay

After complexation of RNA in polyplexes, release of the RNA can be triggered by using Heparin, a strong polyanion. Solution of 100 mg/ml of Heparin is prepared in 1 mM EDTA, 10 mM MES pH 6.1. Heparin solution is diluted 1:10 in 100 μl of formulated RNA sample. The Heparin and formulated RNA solution is incubated 20 min at 30° C. Samples are stored immediately after at 4° C. to avoid RNA degradation.

In Vivo Imaging

BALB/C mice are used for the in vivo testing of formulations. RNA and D-Luciferin injections are performed intramuscular at the musculus tibialis posterior of both legs in each mouse. Upon reaching each of the desired time points, luminescence is measured. Mice are anesthetized in a ventilated chamber with 2.5% isofluorane in oxygen, and imaged 5 minutes after the injection with an in vivo imaging system (IVIS, Perkin Elmer, Waltham, MA). 200 μl of D-Luciferin and 20 μL of RNA/PEI polyplex formulation are injected intramuscular. Luminescence is quantified using the Living Image software (Perkin, Elmer).

ELISpot Assay

This assay is used to measure the frequency of reactive IFNγ secreting CD4+/CD8+ T-cells after in vivo vaccination. Nitrocellulose membrane 96-well plates (Multiscreen, Millipore) are coated with anti-mouse IFNγ monoclonal antibody (1-D1K; Mabtech). One day after coating of IFNγ monoclonal antibody, the spleens of the vaccinated mice are extracted and homogenized for PBMCs extraction. $1 \times 10^6$ cells of the PBMCs solution are plated in each well and are stimulated with specific MHC1 & MHCII specific HA-peptides. Cells were incubated over 48 hrs in RMPI 1640+ GlutaMax(Gibco)+10% FCS. IFNγ secretion was detected using capture and detection antibodies as directed (Mabtech AB) and imaged using an ImmunoSpot Series Analyzer (Cellular Technology Ltd.).

ELISA Assay

Antibodies specific to HA antigen of Strain A/California/07/2009 (H1N1) are measured in sera using a standardized ELISA. Pierce Streptavidin 96-well plates (Nunc) are coated with 1 μg/mL HA-biotinylated recombinant surface protein and incubated overnight at 4° C. Plates are blocked with 1% BSA in PBS. Bound IgG is detected using horseradish peroxidase (HRP)-conjugated goat anti-mouse IgG (AbD Serotec). A dilution series of recombinant murine immunoglobulin is used as a standard to quantify specific antibodies. After 8 minutes of incubation with 3,3',5,5'-Tetramethylbenzidine (TMB), sulfuric acid (25%) is used to stop the reaction. Optical densities were read at 450 nm.

Virus Neutratilization Assay (VNT)

To determine the level of neutralizing antibodies against HA in the serum of animals, VNTs were performed in accordance with the Manual for the Laboratory Diagnosis and Virological Surveillance of Influenza (WHO Global influenza Surveillance Network). A serial dilution of serum samples starting with 1:10 was incubated for 2 hr with 100 TCID50 of infectious influenza virus. The final serum dilution of this assay was 1:1, 280 and thereby also the upper detection limit. The serum-virus mix was then applied to confluent Madin-Darby canine kidney (MDCK) monolayer in 96-well plates and incubated for another 3 days. 50 mL of supernatant was thereafter incubated with 50 mL of 0.5% chicken red blood cells (Lohmann Tierzucht, Cuxhaven, Germany), and red blood cell agglutination was evaluated. The VNT titer was recorded as the inverse of the lowest dilution that inhibited agglutination (VNT/50 mL).

Small Angle X-Ray Scattering (SAXS)

SAXS measurements were conducted at the EMBL P12 bioSAXS beamline at PETRAR III, DESY (German Electron Synchrotron, Hamburg, Germany). The measurements were conducted at an X-ray energy of 10 keV and a flux of $5\times10^{12}$ ph/s; the beam size at the sample position was $0.2\times0.3$ mm$^2$ (v×h, full width half maximum, FWHM) and with the help of the BioSAXS Sample Changer. Low volumes (30 µL) of the sample were transferred to a in vacuum-mounted quartz capillary and a PILATUS 6M detector was used to collect images. Images of the scattering signal were processed by the SASFLOW pipeline: all image were radially averaged and the frames were compared for radiation damage, the frames not affected by radiation damage were averaged and imported into Origin 9.1. Blank references were used to subtract the background scattering.

Automated High-Throughput Circular Dichroism (CD) Spectroscopy

CD spectrum measurements were conducted with a J-1500 CD Spectrometer (JASCO, Inc.). 175 µL of the sample were transferred to a 96-PCR Platte. Standard measurement parameters in a 2 mm cell path length: 200-310 nm wavelength range, 0.1 nm data acquisition interval, 4 sec response, continuous scanning mode with 50 nm/min scan speed and 1 nm bandwidth. The HT Module parameters were set for acquisition of 150 µl sample volume and injection of 575 µL air to deliver the sample to the cell. Flushing between samples was done sequentially with 2×200 µL water, 2×200 µL EtOh:water (1:1) and 2×200 µL EtOH (96%). The drying of the tubing is set to 200 sec. Blank references were used to subtract the background. Data analysis was performed with SpectraManager Software (JASCO, Inc).

Example 1: Characterization of Particle Fractions

In order to investigate the colloidal nature of PEI/RNA polyplex formulation, binding studies were performed, where various amounts of RNA were added to PEI, and the fraction of free RNA was quantified by agarose gel electrophoresis. Measurements were performed for two RNA species: a messenger RNA (mRNA) and a self-amplifying messenger RNA (saRNA). As shown in FIG. 1A, in both cases, binding of the RNA to the PEI could be monitored, as the fraction of residual free RNA decreased with increasing fractions of added PEI. Apparently, the binding characteristics also depended on the individual nucleic acid differing e.g. in sequence and length. So 50% binding of saRNA required an N/P ratio of 0.8 (excess of RNA), while the compared mRNA requires an N/P ratio of 1.4 (excess of PEI). At the N/P ratio of 2 and above, no more free RNA was measured, the RNA was quantitatively bound to the polyplex nanoparticles.

Although, the RNA was completely bound above N/P 2, there were some indications that the particle characteristics further changed towards higher N/P ratios. In FIG. 1B, particle sizes as determined by dynamic light scattering measurements are shown. Particle size decreases up to an N/P value of about 6, above this value the size changes are much smaller.

To elucidate the role of polymer excess given in the formulation, a centrifugation assay is performed separating the two main phases given in the formulation. The size of RNA polyplexes is known to vary between 60-100 nm. The molecular weight of the free polymer is 22 kDa, while the free iVT mRNA is ~500 kDa and saRNA is ~2900 kDa. Knowing these specifications, the centrifugation time can be calculated for a given specific rotor diameter and centrifugation force (20.000 G).

The diagram in FIG. 2A/2B shows that at low N/P ratios the RNA is enriched in the pellet, while increasing the overall PEI concentrations gradually shifts the RNA enriched fraction into the supernatant. As demonstrated in FIG. 3, after recovering the different fractions of RNA in the supernatant phase and in the pellet phase, almost 100% of the initial RNA amount in the formulation can be recovered, supporting that the assay enables an accurate quantitative analysis of RNA/PEI polyplexes in the different populations.

In further experiments (FIG. 6), formulations with larger N/P ration are tested. The RNA content in the supernatant fraction increases correlating to the N/P increment till all the RNA is found exclusively in the supernatant fraction. This N/P ratio at which no further RNA can be found in the pellet fraction, is specific for each type of RNA.

Analysis of the size of polyplexes detected in both fractionated phases of RNA polyplexes (FIG. 4) revealed that a significantly smaller sized population of polyplexes is found in the supernatant, almost 30-40 nm smaller than the particles found in the pellet fraction. The absolute size measured for the supernatant population is not fully accurate, due to a high polydispersity found in this phase, especially at lower N/Ps (N/P<72). The size of these particles suggests a different molecular arrangement of the PEI-RNA formulations.

To confirm that the RNA in the supernatant is bound to PEI and does not exist in form of free RNA, an agarose gel electrophoresis is used. By use of an endogenous polyanion (heparin), the cationic groups of PEI can be countered and the RNA within the nanoparticles could be released and detected as free RNA (FIG. 5). The data confirmed that no free RNA can be detected in the supernatant phase after fractionation but bound to PEI, wherein the bound RNA can be released by heparin incubation.

FIG. 7A shows a clear co-sedimentation of PEI and RNA in different populations indicating different RNA-PEI polyplexes in the formulation. When focusing on polyplexes population sedimenting at 50-400 S, the molecular weight distribution strongly reassembles that of complexed RNA monomers, dimers, trimers, tetramers and pentamers. Analytical ultracentrifuge of same but naked RNA in formulation buffer showed a clear defined peak, where 90% of the RNA could be found sedimenting at 23.56 S. The amount of RNA and PEI showed in FIG. 7B in each population is quantified by integration of the data shown in FIG. 7A, i.e. determining the area under the curve of sedimented PEI and RNA. FIG. 7B shows that significant differences can be observed in the molecular arrangement of the PEI particles in the different populations. Finally, as shown in FIG. 7C, by increasing the N/P ratio of iVT mRNA PEI-Polyplexes a clear shift in the sedimentation coefficient profile of the different populations is achieved. This indicates that increasing the N/P ratio shifts the complexed RNA towards phases having a lower sedimentation coefficient, i.e. to a lower molecular weight monomeric population.

The structure of the monomeric polymer-associated RNA was further investigated by small angle x-ray scattering (SAXS) measurements. RNA was measured in a medium comprising purified monomeric RNA-PEI species, for comparison in buffer only, and in the presence of a higher ionic strength by additionally adding 50 mM NaCl to the bulk phase. In FIG. 26A the direct scattering curves in log-log scale are shown. As already can be seen by the eye, the curves are characterized by distinct, different features. While the RNA in buffer only displays a curve which shows almost no structuring at all, in the presence of NaCl a slight modulation with a minimum around 0.33 $nm^{-1}$ is visible and the curve is flattened towards low q. The curve of RNA in PEI is shows much stronger structural features, with at least two modulations already visible by the eye, at 0.32 and 0.6 $nm^{-1}$. The flattened region at low q is way more extended than it is the case in the presence of salt. The modulations of the PEI curve point towards the presence of compact, globular particles with a very low polydispersity, which are considered to be the individual PEI-dissolved RNA molecules. Also the RNA in the presence of NaCl shows some modulation, which is however less pronounced and present at higher q value. This indicates, that the RNA is also here somewhat condensed, but to a much lower extend, with a less compact packing. These qualitative observations are corroborated by analyzing the curves more thoroughly. In FIG. 26B, Guinier plots of the three data sets are given. In the Guinier approximation, the radius of gyration, $R_g$, of a particle correlates with the intensity as:

$$I(q) = I_0 * \exp\left(-\frac{(R_g)^2}{3}q^2\right)$$

Therefore, a plot of the logarithmic intensity as a function of the square of the momentum transfer q results in a straight line, where $R_g$, can be derived from the slope, $-(R_g)^2/3$. It should be noted, that the Guinier approximation is only valid up to a maximum value of q. For instance, for solid spheres the range in which the approximation is valid is usually considered as $q*R_g$, <1.3. For particles which are not hard spheres with smooth interfaces (anisotropic shapes, rough interfaces, random coil organization) this range is even lower, for example, $q*R_g$, <1. In the Guinier plot, the RNA in PEI shows linear behavior over the whole displayed range, from which the gyration radius of 12 nm can be derived. Notably, the linear behavior is observed also towards the lower q end, down to nearly the lowest measured data point, which indicates, that virtually no larger aggregates (dimers, oligomers, larger particles) are present. In case of the presence of such larger particles, the intensity would show a curved shape, where the intensity increases more than linear in the Guinier plot.

As well, the linear behavior is well maintained up to q=0.1 $nm^{-1}$ ($q^2$=0.01 $nm^{-2}$), i.e., the limit for scattering from solid spheres. Therefore, it can be concluded, that, in fact, the RNA is present in a very compact form, with low anisotropy and low surface roughness.

Also the data in NaCl show a linear range but only up to about 0.001 $nm^{-2}$ (by a factor of 10 lower than for the sample with PEI), and the slope is higher, indicating higher $R_g$. A gyration radius of about 29 nm is obtained from analyzing this curve. Data for RNA in buffer display linear behavior only in the lowest q range, here an Rg of as much as 90 nm may be estimated (there the approximation is valid only up to about 0.0001 $nm^{-2}$, which is at the edge or below the accessible $q^2$-range in this measurement).

In FIG. 26C data are given as Kratky plots, where the scattered intensity multiplied by the square of the momentum transfer, q, as a function of q is given. In the Kratky plot, unfolded (highly flexible) molecules should have a plateau at high q, while compact, globular macromolecules have a bell-shaped (Gaussian) peak. Only for the PEI data a clear peak-like pattern, indicating compact, globular organization is observed. In FIG. 26D the calculated pair distribution functions, P(r), are displayed, which give an information on the distances between scattering moieties in the particles. The peaks give the most abundant distance. Due to the extended conformation, the data did not allow to calculate the curve for RNA in buffer, therefore, here only RNA in NaCl and in PEI are shown. Here the peak for RNA in PEI is more compact and at a significantly lower distance than for RNA in NaCl, supporting the information already derived from the Guinier plots, that the RNA particles in PEI are much more compact. In summary, the RNA dissolved in excess of PEI displays a surprisingly compact organization, where a very high packing density of the RNA must be present. Taking into account the simplest possible model of a solid sphere, the radius of gyration would account for a volume of the single RNA molecule of ($V$=4*pi/3$r^3$, $R_g$=r* $(3/5)^{1/2}$) 15600 $nm^3$. This number can be compared with the volume of the RNA, with a molar mass of 3*$10^6$ Da complexed with PEI at an N/P ratio of two, resulting in the total molar mass of about 4.15*$10^6$ Da (each nucleotide with 330 Da is accompanied by two PEI units of 43 Da each (total mass is then by the factor of 330/456 higher). Together with Avogadro's number, and assuming a density of 1, one can calculate the volume of the assembly to:

$$V = \frac{4.15 * 10^6}{6.023 * 10^{23}} * 10^{21} \approx 7 * 10^3 \; nm^3$$

Although the real density of RNA is somewhat higher than 1 g/mL, his value is surprisingly close to the above calculated volume of 1.56*$10^4$ $nm^3$. No counter ions and no water molecules have been included in the calculation. Furthermore, in practice, the compacted RNA will not be strictly spherical, and a certain decay of packing density with increasing radius must be taken into account, both leading to an increase of the gyration radius of a single molecule. Therefore, these data indicate, that, with the low gyration radius measured here, a further confirmation is given, that only single RNA molecules accounts for the scattering profile. The packing density is extremely high in comparison to other conditions under which RNA is compacted, such as the high salt concentration. For example, with the $R_g$ data presented here, the volume occupied by the RNA particles in PEI is about 15 times lower that it is in NaCl solution, $((12/29)^3)$. Therefore, determination of low gyration radius can be an unequivocal measure to discriminate the PEI compacted RNA from other forms of PEI in solution.

In line with the previously discussed observations that could be derived by investigations of the monomeric-RNA species by SAXS, conformational structure of the RNA in PEI comprising solutions was investigated by circular dichroism. The RNA secondary-tertiary structure was investigated under increment of bulk N/P ratio in the RNA/PEI formulations (0-24-48-72-120-240) and under increment of NaCl concentration in RNA/NaCl formulations. This last group is used for the sake of comparison with another type of polyelectrolyte. Changes in the peak positions of the spectrum, as well as the variation of ellepticity (mdeg) at this peak positions have been correlated with 3 major features of the RNA: (1) the asymmetry of the sugar backbone and its specific rotation/spatial orientation in the so called A-B-Z forms, (2) the hydrogen bonding of the nucleotides pairs, for both Watson-Crick or non-Watson-Crick base paring, and (3) the pi-cationic-driven stacking interaction of the chain(s) (Kypr, J. et al. (2012) Comprehensive Chiroptical Spectroscopy: Applications in Stereochemical Analysis of Synthetic Compounds, Natural Products, and Biomolecules, Volume 2: 575-586) In FIG. 28A, there is a clear shift of the peak position towards lower wavelengths and an increment of the measured ellepticity at the peak position. This both effects correlate with the increment of NaCl concentration in the solution of RNA. Overall the shift of the peak position towards lower wavelength is accompanied with a proportional loss of signal between 280-300 nm, which is the UV-region where chain-stacking effects as previously mentioned can be detected. On the other side, in contrast to the described effect of NaCl in the RNA solutions, PEI induced the opposite effect in the conformational structure of RNA. In FIG. 28B, there is a clear shift of the peak position towards higher wavelengths and a decrement of the measured ellepticity. This both effects correlated with the monotonous increment of the N/P ratio in the RNA/PEI formulation. Overall, the shift of the peak position towards higher wavelengths is accompanied with a proportional gain of signal between 280-300 nm. The nature of interaction and effects in the RNA structure by PEI or NaCl can be followed in FIGS. 28C and 28D, where by converting the PEI or NaCl concentration to a common X-axis of positive charges concentration (mM), it summarizes the opposite effect of PEI and NaCl in terms of shifting the peak position and effects in the ellepticity at the peak position. Pursuant to the previously described effects by SAXS analysis, it can be remarked that the condensation nature of the PEI and NaCl differ dramatically, highlighting that the monomeric RNA structures in polycationic polymers are certainly unique. The monomeric, PEI complexed RNA species are heavily condensed structures with an intrinsic loss of secondary structure of the RNA due to the loss of hydrogen-bonding of the nucleotides, a characteristic red-shift in spectrum and pi-cationic driven interactions of cationic polymer with the nucleotides of RNA that explain the gain of signal in the 280-300 nm wavelength. In contrast to this, NaCl can induce a condensation that is physically limited by the internal RNA organization (secondary structure) and it is well characterized by an observable blue-shift in spectrum.

Example 2: Polymer-Solvated-RNA Fraction can be Detected in the Supernatant After Centrifugal Fraction of Different Cationic Polymers/RNA Polyplexes To confirm the extend of this new concept, apart from PEI-Polyplexes, further cationic polymers, that are either structurally related to PEI or have similar cationic moieties, are tested. Four different polymers beside PEI are tested (FIG. 8) including DEAE-Dextran, Poly-L-lysine, polyvinylamine and polyallylamine. In all the tested polymers, there is a general trend to observe that, when increasing the N/P ratio of the polyplexes, there is a proportional increment of the RNA content in the supernatant after centrifugation. The increment of RNA in the supernatant population of polyplexes differs for the tested polymers, being the highest increment in DEAE-Dextran and PEI RNA-Polyplexes, followed by PLL, PVA and PAA. These results suggest a strong correlation between the structural arrangement of the cationic moieties in the polymer chain to the binding properties with the RNA and the formation of mono/oligomeric RNA fractions. Further to the previously observed effect on high N/P ratio for various different polymers chemically/structurally close to polyethyleneimine, two new polymers of significant different chemical/structural nature are tested. For both PAMAM G(5)-functionalized with (64) arms of penta-L-Lysine (in short G(5)-PLL(64)) and Viromer®, in FIG. 20B and FIG. 22B, respectively, it is shown that with increasing the N/P ratio of the formulation a higher content of monomeric RNA populations is obtained. This clearly indicates that the N/P increment is a universal law applicable to a wide spectrum of cationic-polymer families not only to those closely related to polyethyleneimine.

Example 3: PEI-Solvated-RNA Fraction Observed in the Supernatant After Centrifugal Separation is the Key Driver in the Overall Biological Activity of PEI-Polyplexes Formulation The biological activity of the different fractionated populations of PEI-Polyplexes is investigated after transfection of C2C12 cells with luciferase encoding RNA at various N/P ratios (FIG. 9A, FIG. 9B). Formulated nanoparticles and fractionated populations are diluted accordingly to desired concentration in culture medium that sums a total of 5 ng of formulated saRNA/iVT mRNA per well (100 µL). The results clearly indicate that the supernatant population is the main driving force for the biological activity. In fact, these results suggested that the supernatant fraction of the formulation had even a higher biological activity than that of the parent non-centrifuged formulation.

Example 4: High N/P Ratio Promises Increased Effects, but Are Limited Due to Toxicity in High Doses in Vitro C2C12 transfected with luciferase encoding RNA at various N/P ratio are analyzed in a Luciferase & Viability Assay. Formulated nanoparticles are diluted accordingly to desired concentration in culture medium. While at doses of 50 ng of RNA per 5000 C2C12 cells/well (100 µL) the luciferase activity is high at low PEI concentration, it decreases together with the viability with increasing PEI concentrations (FIG. 10A), there is a completely different picture at ten-fold lower RNA (and PEI) dose: At the lower dose panel no toxicity is observed, the viability remains unchanged, and the measured luciferase activity increases with increasing PEI concentrations (FIG. 10B, FIG. 10C). Therefore although PEI has a toxic effect on the transfected cells, this seems to be overcompensated by an increase of transfection efficacy at low doses resulting in an equivalent overall effect. Furthermore, for both formulated RNAs (iVT mRNA or saRNA), the increment in the N/P ratio perfectly correlates with the increment of the RNA amount found in the supernatant fraction and with the increment in the luminescence. As observed in both Figures (FIG. 10B, FIG. 10C), the luminescence signal ceases to increase as soon as all the RNA is found in the supernatant fraction. Further increment of the N/P does not lead to a higher biological activity, but rather stays in a plateau. This indicates that the increment in the luminescence is only due to the increment of the small sized, monomeric PEI-solvated-RNA content in the formulation and not necessarily the excess of polymer itself. This observation is not exclusive to the biological activity of high N/P ratios with PEI-solvated-RNA but also for other cationic polymers, such as Viromer® and G(5)-PLL(64), where the biological activity (FIG. 20C, FIG. 22C) is shown to increase monotonously with the increment of the RNA amount found in the supernatant fraction (FIG. 20B, FIG. 22B). For these two polymers further increment of the N/P, above the point where the maximum amount of RNA in supernatant fraction cannot be increased, leads to a plateau in the biological activity.

Example 5: Increasing Efficacy of Bioluminescence Expression In-Vivo After Injection of High N/P Ratios at Reduced Doses Fifteen female female BALB/C mice are divided into five study groups. All the groups received the same amount of formulated luciferase encoding saRNA (62.5 ng), applied i.m to each leg. The first group receives 62.5 ng of N/P12 formulated saRNA, the second group 62.5 ng of N/P24, the third group 62.5 ng of N/P48, the fourth group 62.5 ng of N/P72 and the last group 62.5 ng of N/P96. At five time points (24 h, 72 h, 6 d, 9 d, 20 d) the mice are observed by live imaging. FIG. 11A shows the bioluminescence signal detected six days after injection of the polyplexes. There is an increment in the luminescence signal with increasing N/P ratio, reaching the maximum signal at N/P72 (An N/P ratio of 96 seems to have reached the saturation limit). The overall bioluminescence can be represented as an area under the curve (FIG. 11B), here again is clearly shown that the N/P increment leads to a higher efficacy of the injected RNA dose, wherein the efficacy can be increased by a multiple.

Example 6: Increased Efficacy at High N/P Ratios Can Be Used in Vivo for RNA Dose Reduction While Profiting From Same Absolute Biological Overall Performance Nine female BALB/C mice are divided into three study groups. To the first group 500 ng of luciferase encoding saRNA formulated with PEI at an N/P ratio of 12 will be administered. Group 2 receives 250 ng of luciferase encoding RNA formulated with PEI at an N/P ratio of 24, group 3 receives 125 ng of luciferase encoding RNA formulated with PEI at an N/P ratio of 48. At five time points (24 h, 72 h, 6 d, 9 d, 15 d) the mice are observed by live imaging. To reduce stress at 24 h and 72 h only one random half of each group of mice are examined. After 6 d half of all mice (except the control group) are sacrificed and spleen samples are taken. The remaining mice are examined on day 9 and 15 and afterwards sacrificed to gain blood and spleen samples.

After normalization of the luminescence signal to the RNA concentration it becomes visible that the smallest dose with the largest N/P ratio (smallest concentration of RNA, base concentration of PEI) shows the largest effect (FIG. 12A). Therefore, it is possible to significantly decrease the RNA concentration without any loss of effect by maintaining the PEI concentration constant while increasing the PEI to RNA ratio.

The spleen samples are used for preparation of CD8 positive T cells. The T cell preparation are brought into contact with antigen presenting cells bearing BALB/c MHC-I 1, 2 and 3 and are preincubated with the Firefly Luciferase peptides, GFQSMYTFV, VPFHHGFGM and VALPHRTAC. FIG. 12B shows that group 1, group 2 and group 3 have similarly strong CD8 response, but after normalizing the CD8 response to the RNA concentration applied in each group, it is clear to see a ~5-fold increment in the efficacy of injected RNA by increasing the N/P ratio of the formulation from 12 to 48. Therefore the relation between dose and/or N/P ratio to the response does not only apply to transfection efficacy previously observed in vitro, but also to the bioluminescence in vivo and to the immune stimulating potential.

Example 7: High N/P Ratios Lead to Higher Anti-HA IgG and T Even Under Dose-Reduction Schema Twenty-five female BALB/C mice are divided into five study groups. To the first group 500 ng of California/7/2009-HA encoding saRNA formulated with PEI at in an N/P ratio of 12 will be administered. Group 2 receives 125 ng of luciferase encoding RNA formulated with PEI at an N/P ratio of 48, group 3 receives 83.3 ng of luciferase encoding RNA formulated with PEI atn an N/P ratio of 72, group 4 receives 62.5 ng of luciferase encoding RNA formulated with PEI at an N/P ratio of 96 and group 5 receives 50 ng of luciferase encoding RNA formulated with PEI at an N/P ratio of 120. At three time points (14 d, 28 d, 49 d) serum samples are collected from each mice. In FIG. 13A, the absolute values of Anti-HA IgG for the three time points clearly show that even upon reducing the dose of injected saRNA, there is a significant increment in the amount of specific IgG when proportionally increasing the N/P ratio, being the highest value is in group 3. After normalization of the Anti-HA IgG levels in serum to the amount of RNA injected per group, it becomes obvious that with increasing N/P ratio there is a significant increment in the efficacy of the injected RNA after forty nine days, having almost a 12-fold increment for N/P120 to N/P12 (FIG. 13B).

Example 8: PEI-Polymer Length Has an Impact on the Formation of Polymer Associated, Monomeric RNA-Species and the Overall Biological Activity The effect of PEI-polymer length in the RNA formulation is investigated by systematic variation of polymer length, here represented as repetitive units (r.u) of ethyleneimine. As reference serves PEI having a molecular weight of 22500 Da equivalent to ~500 r.u of ethyleneimine. First, the binding affinity of the different PEI-polymer lengths to RNA was evaluated (FIG. 14A). There is a clear correlation between the binding affinity and the polymer length, so that longer polymers (>500 r.u) bind very strongly to RNA and even at very low N/Ps (<1.0), no free RNA can be detected. On the contrary, shorter Polymers (<62 r.u) require higher N/P ratio (>1.3-1.5) to have the RNA fully bound. In parallel to the binding affinity, the amount of RNA found in the supernatant fraction strongly correlated with the polymer-length used at a given N/P ratio (FIG. 14B). The amount of RNA quantified in the supernatant after a centrifugation assay at a given N/P ratio (either 6, 12, 30, 60 or 120) increased monotonously along with the PEI-polymer length from 7 r.u to 500 r.u. Above 500 r.u of ethyleneinimine in PEI, no increment in the fraction of monomeric RNA can be detected. This data suggests, that not only the N/P ratio plays a role in the formation of such monomeric RNA-polymer associated species, but also the length of the polymer plays a fundamental role. Finally, the in-vitro activity, expressed as luminescence measured from the transfection of C2C12 cells, for a given N/P ratio, very strongly increased with the polymer-length used (FIG. 14C). More specifically, having all polymer-lengths tested in-vitro with the same N/P (120), the biological activity increment perfectly correlates with the increment of the amount of RNA in supernatant (FIG. 14B), suggesting that the biological activity strongly depends on the amount of polymer associated, monomeric RNA—and not the excess of positive charges, that was kept constant in this experiment (FIG. 14C).

Further, twenty-four female BALB/C mice are divided into eight study groups. All of the groups received the same amount of formulated saRNA (125 ng) encoding luciferase at the same formulated N/P ratio (120) via i.m administration to each leg. The groups received formulated RNA with different PEI-polymer length: 31-62-125-250-500-1000-2500 r.u. The last group received only formulation buffer. At six time points (1 d, 3 d, 6 d, 9 d, 13 d, 20 d) the mice were observed by live imaging. FIG. 15A shows the bioluminescence signal detected over the whole experiment after the injection of the PEI formulations with the different polymer lengths. FIG. 15B shows the bioluminescence observed at the peak point of expression (6 d) for all tested polymer lengths. The data clearly indicates that the bioluminescence, i.e. biological activity, increases monotonously with the polymer length, that directly correlates with the amount of RNA in supernatant (FIG. 15B).

Example 9: Local RNA Concentration Plays an Important Role in the Formation of Polymer Associated, Monomeric RNA-Species Besides the classical equivoluminar mixing of the RNA containing solution and the PEI containing solution, further volume mixing ratios are systematically investigated to understand the formation of monomeric RNA-polymer associated species. The impact of the variation of the volume mixing ratio is evaluated by monitoring the hydrodynamic size of the formed complexes, the content of polymer associated, monomeric RNA-species by centrifugation assay and finally, by monitoring the in-vitro biological activity. The variations of the volume mixing ratios were performed so that the final concentration of RNA, final N/P ratio and final formulation volume is constant between the tested conditions but the volume mixing ratio of the RNA containing solution and the cationic-polymer containing solution were varied, in order to have different starting concentrations of RNA and cationic-polymer. Overall size of the complexes, as shown in FIG. 16A, decreases for both RNA types, down to 20-30 nm at the lowest RNA starting concentration (i.e. highest initial RNA volume, lowest initial PEI volume). Increasing the starting RNA concentration leads to a significant increment of the size of the complexes, up to 100-120 nm for the highest RNA starting concentration. This holds to be identically applicable not only to PEI-polymer but for other cationic polymers such as Viromer® or G(5)-PLL(64), as shown in FIG. 21 or FIG. 23A, where the same effect on the size of the complexes can be observed by using the lowest RNA starting concentration (i.e. highest initial RNA volume, lowest PEI volume). The evaluation of the amount of polymer associated, monomeric RNA-species, in the supernatant after centrifugation of such formulations is shown in FIGS. 16B and 23B. These figures show that a given constant N/P ratio, the highest initial volume for RNA in excess to the initial polymer volume, leads to the highest amount of RNA found as polymer associated, monomeric RNA in supernatant. Decreasing the mixing ratio of initial RNA volume to the initial polymer volume, leads to a monotonous decrement in the amount of RNA found in supernatant (FIG. 16B, FIG. 23B). Further, the biological activity of the different variations in the volume mixing ratios are evaluated by transfection of C2C12 cells. FIG. 16C shows that with increasing RNA starting concentration (decreasing initial volume), the biological activity decreases monotonously, correlating with the decrement of RNA found in supernatant in FIG. 16B. The highest biological activity in FIG. 16B is observed for the lowest RNA starting concentration in the formulation, i.e. the highest volume mixing ratio of RNA initial volume to polymer initial volume. A further comparison of the observations in FIG. 16B can be confirmed by the biological activity observed after transfection of C2C12 cells in FIG. 17A. In this figure, an equivoluminar mixture at N/P12 and a mixture with a 99:1 mixing ratio of initial RNA volume to initial PEI volume at N/P12 are compared to a equivoluminar mixture at N/P120. The data clearly demonstrates that the excess of positive charges (12 vs 120) plays little role when the RNA is exclusively found as polymer associated, monomeric RNA-species. For the tested mixing ratios in FIG. 16, different N/P ratios were tested in FIG. 18, showing that similar effects can be observed at even lower N/P ratios than 12. Nevertheless, stronger effects with the tested mixing ratios were observed at N/P12 in FIG. 18A and further experiments focuses in the N/P12.

Example 10: Polymer Associated, Monomeric RNA-Species are Colloidal Stable in Liquid Storage Over Longer Periods of Time In order to assess the colloidal stability of monomeric RNA species found in the supernatant of PEI-formulated RNA after centrifugation, two formulations were analysed, that have shown to have a great majority of the RNA (>60%) in supernatant, i.e. as polymer associated, monomeric RNA-species (FIG. 19). The hydrodynamic size of the complexes, the amount of complexes counted in suspension or the amount of RNA in supernatant were monitored over the whole experiment. In total, five different time points (0, 24, 48, 72, 96, 960 hours) were monitored. Overall, there is no significant changes in the hydrodynamic size of the complexes over a time of 960 h, neither of the stored supernatant fraction, i.e. the polymer associated, monomeric RNA-species, nor the bulk phase (FIG. 19A). To confirm these findings, the concentration of particles can be assessed by the amount of counts/s that are measured by DLS in parallel to the hydrodynamic size measurement. As shown in FIG. 19B, no significant change in the counts/s over the whole experiment can be observed, suggesting that there is no shift between the monomeric RNA and non-monomeric RNA species within the bulk formulation or the isolated RNA supernatant. This could be further confirmed in FIGS. 19C and 19D, where the "aged" samples were compared to samples freshly prepared under otherwise identical conditions. Here again, both FIGS. 19C and 19D demonstrated identical size and counts/s, confirming the indications previously given in FIGS. 19A and 19B. Finally, comparing the "aged" stored formulations and freshly prepared controls, the amount of RNA in supernatant was monitored over the whole process and presented in FIG. 19E, as fold change in the quantified amount of RNA in the supernatant, where only small variations within the error bars can be detected. The data presented in FIG. 19E confirms finally that the amount of RNA found in polymer associated, monomeric RNA-species within the formulation does not vary over a period of 960 hours.

Example 11: Lyophilisation of RNA or RNA-Polymer Formulations

Lyophilisation of RNA or RNA-Polymer formulations is an alternative to the classical liquid/frozen storage of such formulations. Therefore the use of lyophilized RNA in an appropriate matrix for direct reconstitution with an aqueous, polymer containing solution was investigated. In FIG. 24 and FIG. 25, the size, in-vitro biological activity, in-vivo generation of Anti-HA IgG, in-vivo Influenza neutralizing titers and Influenza HA-CD4/CD8+ T-Cell response were assessed. Tested lyophilized RNA-PEI formulations, in FIGS. 24C and 24D, were formulated at different N/P ratios and RNA:PEI volume mixing ratios. A fraction of this formulation is frozen or lyophilized. The lyophilized formulation was afterwards reconstituted. The size of the complexes did not change between the freshly prepared, frozen or lyophilized samples in FIG. 24C. The biological activity of such formulations was tested by transfection of C2C12. The biological activity is shown in FIG. 24D, showing that lyophilization of the RNA-PEI formulations preserves the biological activity. In FIGS. 24A and 24B the lyophilization of the RNA was tested in different buffer solutions. The reconstitution of the lyophilized RNA was done using an aqueous, polymer containing solution. The size after reconstitution of the lyophilized RNA or with freshly or frozen control formulations was evaluated in FIG. 24A, showing comparable sizes of all formulations but the formulation generated from RNA lyophilized in pure water. The biological activity of the lyophilized RNA, reconstituted with a polymer solution for a final N/P of 120 is evaluated in FIG. 24B. In accordance with FIG. 24A this experiment showed the highest biological activity using RNA lyophilized in MBS and the lowest expression was obtained from RNA lyophilized in pure water. In FIG. 25, the biological performance of the lyophilized RNA-PEI formulations or the lyophilized RNA was further evaluated in-vivo. Thirty five female BALB/C mice were divided into seven study groups. The first group received only formulation buffer. All other six groups received California/7/2009-HA encoding saRNA formulated with PEI under different conditions. The second group received 500 ng of saRNA formulated at N/P12, the third group received 125 ng of saRNA formulated at N/P120, the fourth group received 125 ng of saRNA formulated at N/P120 that was previously lyophilized and reconstituted with water prior injection to the mice in the group, the fifth group received 125 ng of saRNA lyophilized in pure water and reconstituted with a polymer solution to have a final N/P 120, the sixth group received 125 ng of saRNA lyophilized in MBG buffer and reconstituted with a polymer solution to have a final N/P 120, the final group received 125 ng of saRNA lyophilized in MBS buffer and reconstituted with a polymer solution to have a final N/P 120. At three time points (14 d, 28 d, 56 d) serum samples were collected from each mice. In FIG. 25A, the absolute values of Anti-HA IgG obtained by ELISA-method are represented for the three time points as area under the curve for each group. The Anti-HA IgG levels were highest for the group injected with saRNA lyophilized in MBS, followed by the freshly prepared benchmark N/P120 and by the lyophilized RNA-PEI formulation at N/P120. No evident IgG levels against HA could be detected in the group treated with lyophilized RNA in water (only one of five mice was responsive). The previous findings were confirmed by the virus neutralizing titers that can be obtained from the serological samples taken after 56 d (latest time point of the experiment) in FIG. 25B. The data confirms that the highest VNT is observed in the group injected with saRNA lyophilized in MBS, followed by the freshly prepared benchmark N/P120 and by the lyophilized RNA-PEI formulation at N/P120. Finally, in FIG. 25C, the CD4/CD8+ T-Cell response to influenza peptides is assessed in splenocytes of the extracted spleens at the final time point measured via IFN-ELISPOT. The highest T-Cell response (both CD4 and CD8) was obtained from the group treated with lyophilized RNA in MBS, and was 2-fold higher than the freshly prepared N/P120 or 10-fold higher (normalized to dose) than the freshly prepared N/P12. Overall, lyophilization is proven to not only to provide a longer period of stability for the use of such systems in vaccination approaches, but also offer a higher efficacy in such approach at the same dose/conditions if the lyophilization is done in the appropriate matrix.

Example 12: Increasing Efficacy of Bioluminescence Expression In-Vivo After Injection of High N/P Ratios at Reduced Doses for Other Cationic Polymers Twenty seven female female BALB/C mice were divided into nine study groups. All the groups received the same amount of formulated luciferase encoding saRNA (125 ng), applied i.m. into each leg. The first four groups received 125 ng of formulated G(5)-PLL(64)/saRNA at different N/P ratios, 12-24-48-96. The next four groups received 125 ng of formulated Viromer®/saRNA at different N/P ratios, 12-24-48-96. One last group received only formulation buffer without saRNA or polymer. At four time points (1 d, 3 d, 6 d, 8 d) the mice were observed by live imaging. FIGS. 27A and 27B shows the bioluminescence signal detected over the whole experiment after the injection of the different polymer-polyplexes. FIG. 27C shows the area under the curve for the expression of each group over the whole experiment, as a function of the tested N/P ratio and grouped into the two different tested polymers. There is clear increment in the luminescence signal with increasing N/P ratio, reaching the maximum signal at N/P48, while above this N/P ratio, there seems to be a detrimental effect that is in line with the in-vitro observations for this both cationic polymers, namely local toxicity effects that can virtually make the expression of RNA impossible, if the transfected cells are dying prior expression of the RNA. The biological activity of both polymers at higher N/P ratio in-vivo confirms the previous findings (FIG. 11) and shows the universal applicability of increasing the N/P to other cationic polymers, in order to enhance the biological activity by increasing the amount of RNA in the polymer associated, monomeric RNA-species (FIGS. 8, 20B, 22B).

The invention claimed is:

1. A composition comprising RNA and a cationic or polycationic polymer in an aqueous phase, wherein the ratio of the number of cationic or polycationic polymer nitrogen groups to phosphate groups of RNA (N/P) is at least 48 and wherein the cationic or polycationic polymer has an average molecular weight between 10000 Da and 50000 Da, wherein the predominant fraction of the RNA molecules comprises individual RNA molecules associated with the cationic or polycationic polymer in solution, wherein the predominant fraction of the RNA molecules is the fraction which contains the most RNA on a mass basis, wherein the RNA is mRNA or saRNA, and wherein the cationic or polycationic polymer is or comprises poly(ethyleneimine).

2. The composition of claim 1, wherein the majority of the RNA molecules associated with the polymer are present as RNA monomolecular species.

3. The composition of 1, wherein the poly(ethyleneimine) is a linear cationic or polycationic polymer, or wherein the poly(ethyleneimine) is a branched cationic or polycationic polymer.

4. The composition of claim 1, wherein the poly(ethyleneimine) has a mean molar mass between 15000 Da and 30000 Da, between 20000 Da and 25000 Da, or of about 22500 Da.

5. The composition of claim 1, which additionally comprises a buffering substance selected from the group consisting of 4-(2-hydroxyethyl)-1-piperazineethanesulfonic acid (HEPES), 3-morpholino-2-hydroxypropanesulfonic acid (MOPSO), 2-(N-morpholino) ethanesulfonic acid (MES), Bis-tris buffering systems, carboxylic acid buffering systems, phosphatic acid buffering systems, or citric acid buffering systems, where the pH is in the range from 4 to 8; or wherein the composition has an ionic strength of 50 mM or less; or wherein the concentration of free positively charged divalent cationic ions is 20 uM or less.

6. The composition of claim 1, wherein the RNA predominantly consists of individual cationic or polycationic polymer-associated RNA molecules.

7. The composition of claim 1, wherein the mass fraction of RNA present as RNA monomers or RNA oligomers having four or less RNA copies per oligomer unit is higher than 60%, higher than 70%, higher than 80%, higher than 90%, higher than 95%, higher than 96%, higher than 97%, higher than 98%, or higher than 99% of the total amount of RNA.

8. The composition of claim 1, wherein the composition does not comprise RNA aggregates.

9. The composition of claim 1, wherein the composition does not comprise viral RNA particles.

10. The composition of claim 1, formulated for use in non-viral gene delivery.

11. The composition of claim 1, wherein the ratio of the number of cationic or polycationic polymer nitrogen groups to phosphate groups of RNA (N/P) ranges from 48 to 300.

12. The composition of claim 1, wherein the ratio of the number of cationic or polycationic polymer nitrogen groups to phosphate groups of RNA (N/P) is at least 72.

13. The composition of claim 11, wherein the ratio of the number of cationic or polycationic polymer nitrogen groups to phosphate groups of RNA (N/P) ranges from 60 to 200, 80 to 150, or 70 to 120.

14. A method for forming a composition comprising RNA and a cationic or polycationic polymer in an aqueous phase, wherein the predominant fraction of the RNA molecules comprises individual RNA molecules associated with the cationic or polycationic polymer in solution, wherein the predominant fraction of the RNA molecules is the fraction which contains the most RNA on a mass basis, the method comprising mixing RNA and an excess of cationic or polycationic polymer, or mixing a cationic or polycationic polymer containing solution and a RNA containing solution, and wherein the ratio of the number of the cationic or polycationic polymer nitrogen groups to phosphate groups of RNA (N/P) is at least 48 and wherein the cationic or polycationic polymer has an average molecular weight between 10000 Da and 50000 Da, wherein the RNA is mRNA or saRNA, and wherein the cationic or polycationic polymer is or comprises poly(ethyleneimine).

15. The method of claim 14, wherein the ratio of the number of cationic or polycationic polymer nitrogen groups to phosphate groups of RNA (N/P) ranges from 48 to 300.

16. The method of claim 15, wherein the ratio of the number of cationic or polycationic polymer nitrogen groups to phosphate groups of RNA (N/P) ranges from 60 to 200, 80 to 150, or 70 to 120.

17. The method of claim 14, wherein the mixing of RNA and cationic or polycationic polymer comprises mixing a solution of the RNA and a solution of the cationic or polycationic polymer, or mixing equal volumes of a solution of the RNA and a solution of the cationic or polycationic polymer, or dissolving dehydrated RNA in a solution of the cationic or polycationic polymer.

\* \* \* \* \*

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Firefly Luciferase peptide

<400> SEQUENCE: 1

Gly Phe Gln Ser Met Tyr Thr Phe Val
1               5

<210> SEQ ID NO 2
<211> LENGTH: 9
<212> TYPE: PRT
<213> ORGANISM: Artificial Sequence
<220> FEATURE:
<223> OTHER INFORMATION: Firefly Luciferase peptide

<400> SEQUENCE: 2

Val Pro Phe His His Gly Phe Gly Met
1               5

<210> SEQ ID NO 3
<211> LENGTH: 9
<212> TYPE: PRT
<213> ORGANISM: Artificial Sequence
<220> FEATURE:
<223> OTHER INFORMATION: Firefly Luciferase peptide

<400> SEQUENCE: 3

Val Ala Leu Pro His Arg Thr Ala Cys
1               5
```